United States Patent [19]

Tanii et al.

[11] Patent Number: 5,469,840
[45] Date of Patent: Nov. 28, 1995

[54] ELECTROMOTIVE WARPING TYPE ENDOSCOPE WITH VELOCITY CONTROL

[75] Inventors: Yoshiyuki Tanii; Motokazu Nakamura, both of Hachioji; Yoshikatsu Nagayama, Sagamihara; Katsuaki Morita, Hachioji; Hiroki Hibino, Hachioji; Akira Suzuki, Hachioji, all of Japan

[73] Assignee: Olympus Optical, Ltd., Tokyo, Japan

[21] Appl. No.: 242,052

[22] Filed: May 10, 1994

Related U.S. Application Data

[63] Continuation of Ser. No. 880,065, May 7, 1992, abandoned.

[30] Foreign Application Priority Data

Dec. 10, 1991 [JP] Japan .................................. 3-325950
Jan. 31, 1992 [JP] Japan .................................. 4-016681
Feb. 7, 1992 [JP] Japan .................................. 4-022897

[51] Int. Cl.[6] ............................................. A61B 1/005
[52] U.S. Cl. ...................... 600/117; 600/109; 600/145; 600/118; 600/152
[58] Field of Search ................ 128/4–10; 604/95, 604/156; 388/910, 838

[56] References Cited

U.S. PATENT DOCUMENTS

| 4,499,895 | 2/1985 | Takayama . | |
| 4,503,842 | 3/1985 | Takayama | 128/4 |
| 4,559,928 | 12/1985 | Takayama | 128/6 |
| 4,941,454 | 7/1990 | Wood et al. . | |
| 4,982,725 | 1/1991 | Hibino et al. | 128/4 |
| 5,060,632 | 10/1991 | Hibino et al. | 128/6 |

FOREIGN PATENT DOCUMENTS

| 0078017 | 5/1983 | European Pat. Off. | 128/4 |
| 58-69523 | 4/1983 | Japan . | |
| 58-78635 | 5/1983 | Japan . | |
| 63-59329 | 11/1988 | Japan . | |
| 1-23450 | 2/1989 | Japan . | |
| 1-24653 | 3/1989 | Japan . | |
| 1-270119 | 10/1989 | Japan . | |
| 1-317423 | 12/1989 | Japan . | |

*Primary Examiner*—Richard J. Apley
*Assistant Examiner*—John P. Leubecker
*Attorney, Agent, or Firm*—Armstrong, Westerman, Hattori, McLeland & Naughton

[57] ABSTRACT

An endoscope apparatus according to the present invention includes a warping velocity control device which receives an angle of warp detected by an angle detection device and a value of an electric current realized at this angle of warp and detected by an electric current detection device. The control device makes comparisons between the angle of warp and the value of the electric current and data about a normal state stored in a storage device. If the result is larger than data for the normal state by a predetermined value, the warping velocity is lowered while a discrimination is made that an abnormal state (the warp-enabled portion has come in contact with the body wall) takes place. Additionally, the apparatus could include a time detecting device for detecting a time in which an electric quantity supplied to a drive means is larger than a predetermined time. The warping velocity control device controls the warping velocity according to the comparison made by the time detecting device.

2 Claims, 54 Drawing Sheets

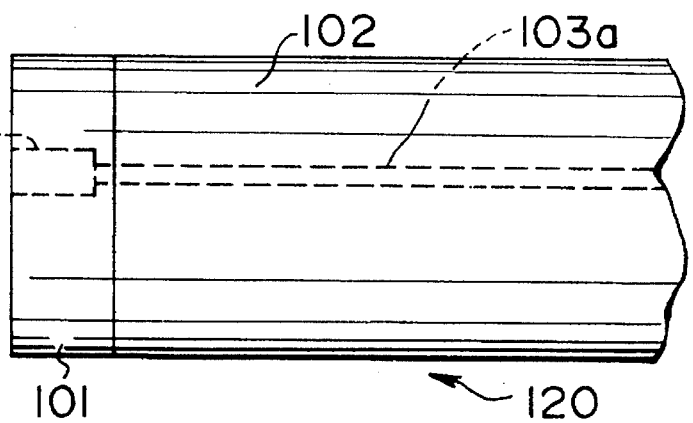
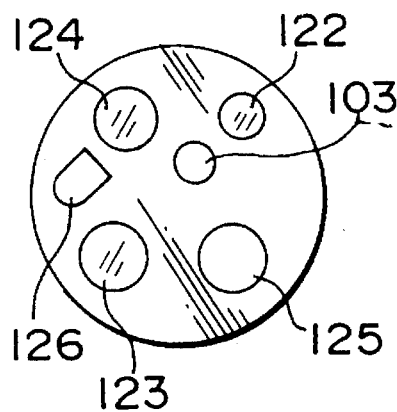
FIG. 42(b)  FIG. 42(a)
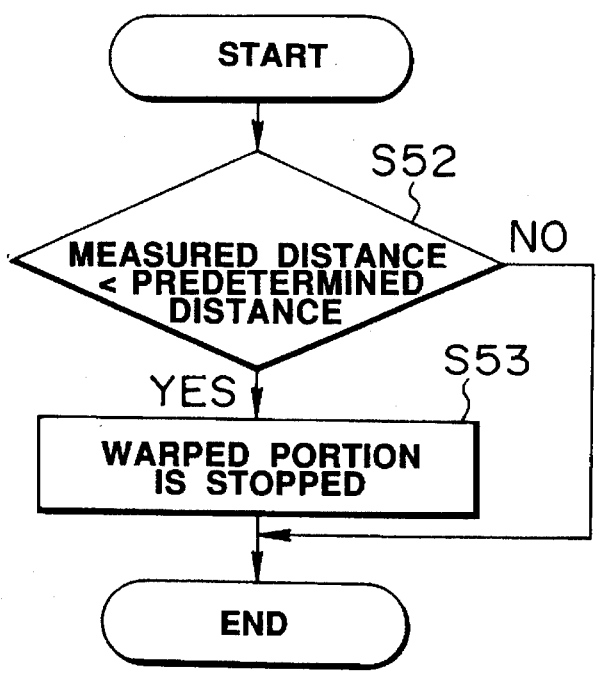
FIG. 43

|      | U | D | T2  | T3  | T4  | T5  |
|------|---|---|-----|-----|-----|-----|
| UP   | H | H | off | off | on  | on  |
| DOWN | L | L | on  | on  | off | off |
| STOP | H | L | off | off | off | off |

FIG. 74 (a)  FIG. 74 (b)
FIG. 75
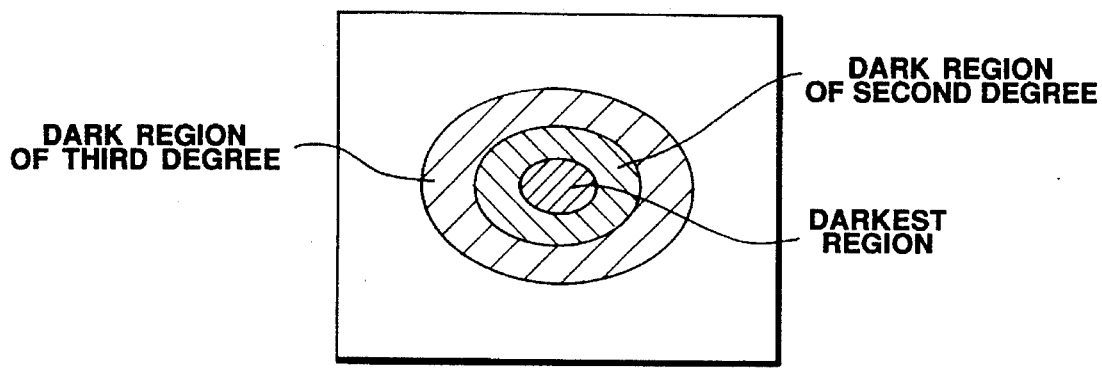
FIG. 76
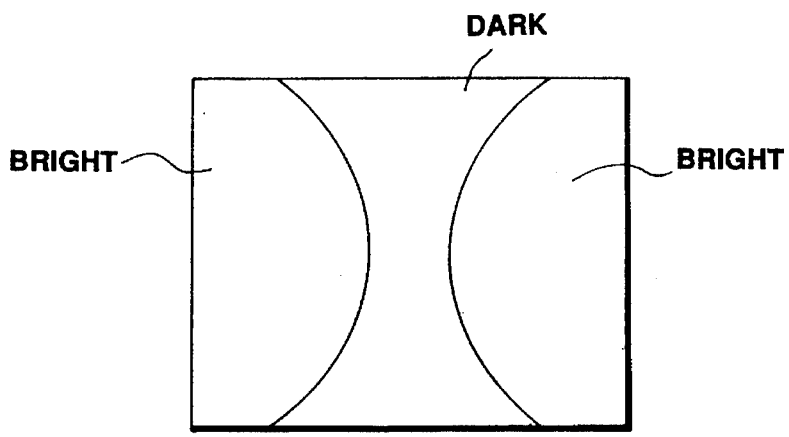

| 1 | 1 | 1 | 1 | 1 |
|---|---|---|---|---|
| 0 | 1 | 1 | 1 | 0 |
| 0 | 1 | 1 | 1 | 0 |
| 0 | 1 | 1 | 1 | 0 |
| 1 | 1 | 1 | 1 | 1 |

| 1 | 1 | 1 | 1 | 1 |
|---|---|---|---|---|
| 0 | 1 | 1 | 1 | 0 |
| 0 | 0 | 1 | 0 | 0 |
| 0 | 0 | 1 | 0 | 0 |
| 0 | 0 | 1 | 0 | 0 |

| 0 | 0 | 0 | 0 | 0 |
|---|---|---|---|---|
| 0 | 1 | 0 | 1 | 0 |
| 0 | 1 | 0 | 0 | 1 |
| 0 | 0 | 1 | 1 | 0 |
| 0 | 0 | 0 | 0 | 0 |

FIG. 80 (a)
FIG. 80 (b)
FIG. 80 (c)
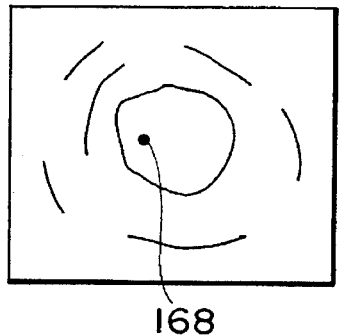
168
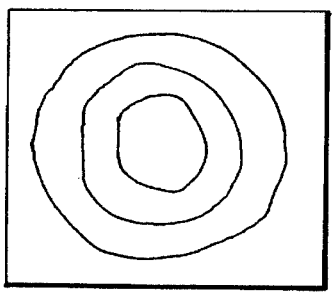
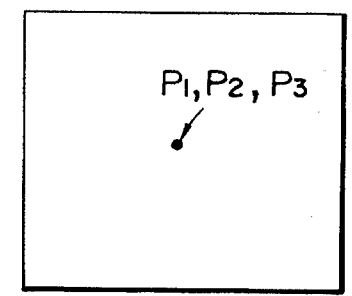
FIG. 81 (a)
FIG. 81 (b)
FIG. 81 (c)
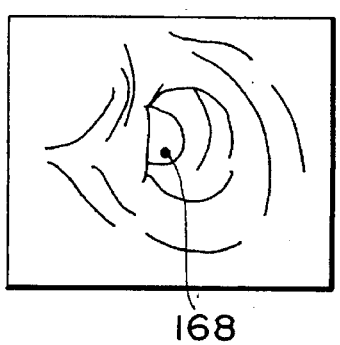
168
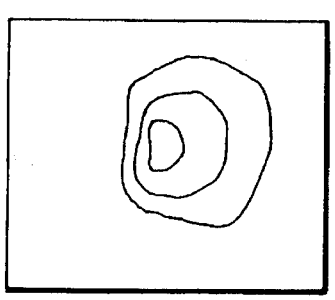
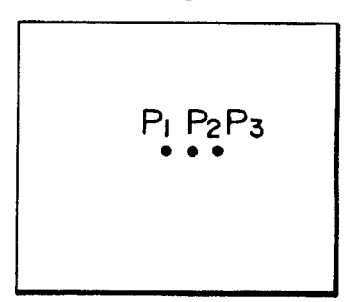

| INPUT | | | OUTPUT | |
|---|---|---|---|---|
| A | B | C | D | E |
| H | H | H | L | H |
| H | L | H | L | L |
| L | L | H | L | L |
| H | H | L | L | H |
| H | L | L | H | L |
| L | L | L | L | L |

| INPUT | | | | OUTPUT | |
|---|---|---|---|---|---|
| A | B | C | F | D | E |
| H | H | H | H | L | H |
| H | L | H | H | L | L |
| L | L | H | H | L | L |
| H | H | L | H | L | H |
| H | L | L | H | H | L |
| L | L | L | H | L | L |
| X | X | X | L | L | H |

ELECTROMOTIVE WARPING TYPE ENDOSCOPE WITH VELOCITY CONTROL

This application is a continuation of application Ser. No. 07/880,065 filed May 7, 1992, now abandoned.

BACKGROUND OF THE INVENTION

1. Field of the Invention

The present invention relates to an improvement in an electromotive warping type endoscope apparatus for electrically warping a warp-enabled portion thereof.

2. Description of the Related Art

Recently, endoscopes have been widely used each of which has an elongated insertion portion for use to be inserted into the colon so as to observe the internal organs and, if necessary, capable of performing various curing treatments by using a treatment tool inserted into a treatment-tool channel thereof.

Furthermore, industrial endoscopes have been widely used to observe or inspect internal flaws or corrosion of boilers, gas turbines, pipes of chemical plants and the bodies of automobile engines.

The endoscope of the aforesaid type usually comprises a mechanism for warping a warp-enabled portion formed adjacent to the leading portion thereof and an electric driving means such as a motor for driving the aforesaid warping mechanism. The electromotive warping type endoscope of the aforesaid type is combined with an endoscope, a warp control device for controlling the warping operation of the endoscope and a light source device and the like, so that an electromotive warping type endoscope apparatus is constituted so as to be used practically.

As disclosed in Japanese Patent Laid-Open No. 1-317423, Japanese Patent Laid-Open No. 58-78635, Japanese Patent Publication No. 63-59329 and Japanese Patent Laid-Open No. 58-69523, the electromotive warping type endoscope apparatus of a type having the warp control device provided with a control means for controlling the warping velocity by changing the time in which the warp operation switch is operated, the quantity of the operation of the switch or the power for operating the switch has been disclosed in order to improve the handling facility.

In a case where the endoscope is inserted into the tract or the like, the operator must insert the endoscope while judging the insertion direction of the endoscope and control the warp so as to make the leading portion of the insertion portion face the insertion direction.

However, considerably excellent skill and experience are required when the endoscope is inserted at the time of inspecting the colon or the like.

Accordingly, the applicant of the present invention has disclosed a method in Japanese Patent Application No. 1-23450 which is capable of detecting the direction into which the endoscope is inserted by extracting a dark region included in the endoscope image. Furthermore, in Japanese Patent Application No. 1-24653, the applicant has disclosed a technology in which the direction in which the endoscope is inserted is detected and the warping operation is controlled in such a manner that the leading portion of the insertion portion faces the detected insertion direction.

In a case where the tract is formed straight, it is necessary for the endoscope to simply move forward linearly in the detected insertion direction. However, if the tract is bent, the endoscope must be moved to correspond to the state of bending. However, there has not been a means which is capable of detecting the state of bending of the tract or the like.

Therefore, the applicant of the present invention has suggested an insertion control device in Japanese Patent Application No. 1-270119 which is capable of discriminating the conditions for inserting the endoscope in accordance with the state of a subject of the inspection on the basis of an image signal and therefore capable of automatically inserting the endoscope in a suitable manner according to the state of the subject of the inspection.

In a case where an electronic endoscope or the like is used in the electromotive warping type endoscope apparatus, the warping operation is sometimes performed while observing the monitor image. In this case, the warping velocity is constant regardless of the distance between the subject and the image-sensing means such as the electronic endoscope or the like. Therefore, when the warping is instructed by operating a warping operation switch or the like, the monitor image moves slowly when the aforesaid distance is long and the same moves quickly when the distance is short. As described above, the image moving velocity becomes different due to the distance from the subject, causing a problem to arise in that the warping velocity cannot be easily recognized and therefore the warping operation becomes difficult to perform.

On the other hand, there is a case in which the angle of operation of a warping joy-stick and the angle of warp of the warp-enabled portion does not coincide with each other at the initial operation after the power has been supplied. In this case, there arises a fear that the warp-enabled portion will be warped in an unintentional direction because the operator does not know the fact that the two angles are different from each other.

The conventional electromotive warping type endoscope apparatus is arranged to change the warping velocity by changing the time in which the warping operation is performed, the quantity of the operation, the power for performing the operation or operating the operation switch or the like. However, the state of the insertion portion or that of the warp-enabled portion cannot be recognized and therefore there arises a problem in that the operator must operate the endoscope while always paying attention to prevent contact of the endoscope with the inside wall of the colon.

Although there has been disclosed a structure in Japanese Patent Laid-Open No. 58-69523 which is arranged in such a manner that a switch for finely adjusting the warp is provided in addition to the warp operation switch, the state of the insertion portion or the warp-enabled portion cannot be detected similarly. Therefore, a problem arises in that the operation becomes too complicated because the operator must always pay attention to prevent the contact between the endoscope and the body wall although the operator performs the warping operation while finely moving it by using the aforesaid switch for finely adjusting the warp. What is even worse, there is a risk of injuring the body wall if the warping operation is continued in a state where the endoscope is in contact with the body wall.

The aforesaid insertion control device or the like which has been disclosed in Japanese Patent Application No. 1-270119 and which is capable of automatically inserting the endoscope has no special means for use at the time of the warping operation in the automatic insertion mode.

In the electromotive warping type endoscope apparatus, it is important to know that the warp-enabled portion is straight. For example, in an operation to be performed while observing the monitor image, if the state of straightness can be recognized from only the scope while eliminating the necessity of looking at the warp operation switch or the like, the operator is required to look only at the monitor scope. Therefore, the operability can be improved.

As a related art relating to the operation of warping an endoscope or the like, an apparatus has been disclosed in U.S. Pat. No. 4,941,454 which is arranged in such a manner that a pulse width modulation control is employed to control the operation of pulling a warping cable and controlling the tension.

SUMMARY OF THE INVENTION

An object of the present invention is to provide an electromotive warping type endoscope apparatus capable of eliminating the complexity of an operation at the time of a warping operation and capable of improving the operability of the warping operation.

Another object of the present invention is to provide an electromotive warping type endoscope apparatus capable of detecting contact of an insertion portion with the subject of the inspection and therefore capable of improving safety in the warping operation.

Another object of the present invention is to provide an electromotive warping type endoscope apparatus capable of improving the safety in the warping operation when the insertion portion is automatically inserted.

Another object of the present invention is to provide an electromotive warping type endoscope apparatus capable of recognizing a straight state of the warp-enabled portion and therefore capable of improving the operability and the safety in the warping operation.

Another object of the present invention is to provide an electromotive warping type endoscope apparatus capable of avoiding a dangerous state realized due to the difference between the instructed quantity of the quantity of warp instruction means and the quantity of warp of the warp-enabled portion at the time of supplying power and therefore capable of improving the operability and the safety in the warping operation.

Another object of the present invention is to provide an electromotive warping type endoscope apparatus in which the movement of the endoscope image displayed on a display means is made constant so as to make the relationship between the warping operation and the quantity of warp to be easily recognized regardless of the given velocity at which the quantity of instruction of the quantity of warp instruction means and which is therefore capable of improving the operability of the warping operation.

According to an aspect of the present invention, there is provided an electromotive warping type endoscope apparatus comprising: a warping mechanism for warping a warp-enabled portion provided for an insertion portion of an endoscope which can be inserted into a subject to be inspected; driving means for driving the warping mechanism; detecting means for detecting a state of the insertion portion; and warping velocity control means for supplying a control signal for controlling the warping velocity of the warp-enabled portion to the driving means according to information about the detection performed by the detecting means. Therefore, the warping velocity control means controls the warping velocity of the warp-enabled portion on the basis of information about the state of insertion or warp detected by the detecting means.

Other and further objects, features and advantages of the invention will appear more fully from the following description.

BRIEF DESCRIPTION OF THE DRAWINGS

FIG. 1 is an overall structural view which illustrates an electromotive warping type endoscope apparatus;

FIG. 2 is a cross-sectional view which illustrates an endoscope insertion portion;

FIG. 3 is a block diagram which illustrates the electromotive warping type endoscope apparatus featuring an essential portion;

FIG. 4 is a structural view which illustrates a driven gear in which magnetism is disposed;

FIG. 5 is a flow chart which illustrates an initial operation in a warp control operation;

FIG. 6 is a flow chart which illustrates a warping direction recognition and its instruction in the warp control operation;

FIG. 7 is a flow chart which illustrates the warp control operation for obtaining a predetermined angle of warp;

FIG. 8 is a flow chart which illustrates the warping control operation for taking a measure against a dangerous state;

FIG. 9 is a perspective view which illustrates a leading portion of an endoscope;

FIG. 10 is a block diagram which illustrates the electromotive warping type endoscope apparatus featuring an essential portion;

FIG. 11 is a flow chart which illustrates an operation of controlling the warping operation and warping velocity;

FIG. 12 is a flow chart which illustrates an operation of setting a velocity setting flag;

FIG. 13 is a flow chart which illustrates an operation of switching the warping velocity;

FIG. 14 is a flow chart which illustrates an operation of emergency-stopping a warp-enabled portion;

FIGS. 15 to 17(b) illustrate a third embodiment of the present invention, where

FIG. 15 is a block diagram which illustrates the electromotive warping type endoscope apparatus featuring an essential portion;

FIG. 16 is an overall structural view which illustrates the electromotive warping type endoscope apparatus;

FIGS. 17(a) and 17(b) show cross-sectional views illustrating an optical system of the leading portion of the endoscope;

FIG. 18 is a schematic overall structural view which illustrates the electromotive warping type endoscope apparatus;

FIG. 19 is a structural view which illustrates a portion of a warping mechanism;

FIG. 20 is an electrical block diagram which illustrates a motor control device;

FIG. 22 is a schematic overall structural view which illustrates the electromotive warping type endoscope apparatus;

FIG. 23 is a structural view which illustrates a portion of the warping mechanism;

FIG. 24 is an electrical block diagram which illustrates a motor control device;

FIGS. 25 and 26 illustrate a fifth embodiment of the present invention, where

FIG. 26 is an electrical block diagram which illustrates the motor control device;

FIGS. 27 to 30 illustrate a sixth embodiment of the present invention, where

FIG. 27 is an overall structural view which illustrates the electromotive warping type endoscope apparatus;

FIG. 28 is a structural view which illustrates a portion of the warping mechanism;

FIG. 29 is a cross-sectional view which illustrates the warping mechanism of the endoscope;

FIG. 30 is an electrical block diagram which illustrates the warp controlling operation;

FIGS. 31 to 33 illustrate a seventh embodiment of the present invention, where

FIG. 31 is an overall structural cross-sectional view which illustrates the endoscope operation portion of the electromotive warping type endoscope apparatus;

FIG. 32 is a side elevational view which illustrates a portion of the warping mechanism;

FIG. 33 is an electrical block diagram which illustrates the motor control device;

FIG. 35 is an electrical block diagram which illustrates the warp control system of the electromotive warping type endoscope apparatus;

FIG. 36 is a flow chart which illustrates the warp control operation;

FIG. 37 is an overall structural view which illustrates the electromotive warping type endoscope apparatus;

FIG. 38 is a structural view which illustrates the warping mechanism;

FIG. 39 is a perspective view which illustrates a supersonic driving system of the endoscope;

FIG. 40 is an electronic block diagram which illustrates the motor control device;

FIGS. 41 to 43 illustrate a ninth embodiment of the present invention, where

FIG. 41 is a structural view which illustrates the electromotive warping type endoscope apparatus featuring an essential portion;

FIG. 42(a) is a plan structural view which illustrating the leading portion of the endoscope;

FIG. 42(b) is an end view of the leading portion of the endoscope shown in FIG. 42(a);

FIG. 43 is a flow chart which illustrates the warping velocity control operation;

FIG. 44 is an overall schematic structural view which illustrates the electromotive warping type endoscope apparatus;

FIG. 45 is a flow chart which illustrates control of the warping velocity;

FIG. 46 is a histogram of the pixel density;

FIG. 49 is a structural view which illustrates the electromotive warping type endoscope apparatus featuring an essential portion;

FIG. 50 is a flow chart which illustrates control of the warping velocity;

FIG. 51 illustrates an image region for obtaining an image correlation;

FIG. 52 is a structural view which illustrates the electromotive warping type endoscope apparatus featuring an essential portion;

FIG. 53 is a flow chart which illustrates control of the warping velocity;

FIG. 54 is a flow chart which illustrates control of the warping velocity;

FIG. 55 is a structural view which illustrates a warp driving system and the like of the electromotive warping type endoscope apparatus;

FIG. 56 is an electrical block diagram which illustrates warp control to be performed in the electromotive warping type endoscope apparatus;

FIG. 57 is an overall structural view which illustrates the electromotive warping type endoscope apparatus;

FIG. 58 is an electrical block diagram which illustrates a warp control system of the apparatus shown in FIG. 57;

FIGS. 59, 60(a) and 60(b) illustrate a fifteenth embodiment of the present invention, where FIG. 59 is a schematic structural view which illustrates the electric circuits or the warping mechanism and the control system of the endoscope apparatus;

FIG. 61 is a block diagram which illustrates the electromotive warping type endoscope apparatus featuring an essential portion;

FIG. 62 is a schematic block diagram which illustrates the electromotive warping type endoscope apparatus according to the sixteenth embodiment;

FIG. 63 is an overall schematic structural view which illustrates the electromotive warping type endoscope apparatus;

FIG. 64(a) is a specific structural view which illustrates an example of a structure for detecting the warp angle rotation;

FIG. 64(b) is a structural view which illustrates a slit plate of an encoder;

FIG. 65 is a structural view which illustrates another example of a structure for detecting the angle of warp;

FIG. 66 is a specific structural view which illustrates a drive circuit;

FIG. 67 is a truth value table of a circuit shown in FIG. 66;

FIG. 68 is a flow chart which illustrates warping velocity switching control;

FIG. 69 is a flow chart which illustrates another example of the warping velocity switching control;

FIGS. 70 to 82 illustrate a seventeenth embodiment, where

FIG. 70 is a schematic structural view which illustrates the warping mechanism and a warp/insertion proceeding and retracting means of the endoscope;

FIG. 71 is a block diagram which illustrates the structure of an automatic insertion device of the endoscope;

FIG. 72 is an overall schematic structural view which illustrates the endoscope apparatus;

FIG. 73 is a circuit diagram which illustrates a binary circuit and a threshold level setting portion;

FIGS. 74(a) and 74(b) illustrate the operation performed by a dark portion extracting portion;

FIG. 75 illustrates a plurality of regions extracted by the dark portion extracting portion;

FIG. 76 illustrates an endoscope image in a state where the leading portion of the endoscope has excessively approached the subject of the inspection;

FIGS. 77(a) and 77(b) illustrate an example of a contrast pattern of a pattern comparison portion;

FIG. 78 illustrates an operation performed by a boundary extracting portion;

FIG. 79 illustrates an operation performed by a center extraction calculating portion;

FIGS. 80(a), 80(b) and 80(c) illustrate an operation performed by the automatic insertion device in a case where the tract is straight;

FIGS. 81(a), 81(b), and 81(c) illustrate an operation performed by the automatic insertion device in a case where the tract is bent;

FIGS. 82(a), 82(b), 82(c), and 82(d) illustrate functions between the angle of warp and the warping velocity;

FIG. 83 illustrates the relationship between the insertion velocity and the set warping velocity;

FIG. 84 is an overall structural view which illustrates the electromotive warping type endoscope apparatus;

FIG. 85 is a block diagram which illustrates the electromotive warping type endoscope apparatus featuring an essential portion;

FIG. 86 is a circuit diagram which illustrates control of driving of the warp-enabled portion;

FIG. 87 is a truth value table of a circuit shown in FIG. 86;

FIG. 88 is a circuit diagram which illustrates control of driving the warp-enabled portion; and FIG. 89 is a truth value table of a circuit shown in FIG.

DETAILED DESCRIPTION OF THE PREFERRED EMBODIMENTS

Preferred embodiments of the present invention will now be described with reference to the drawings.

Figure 1:
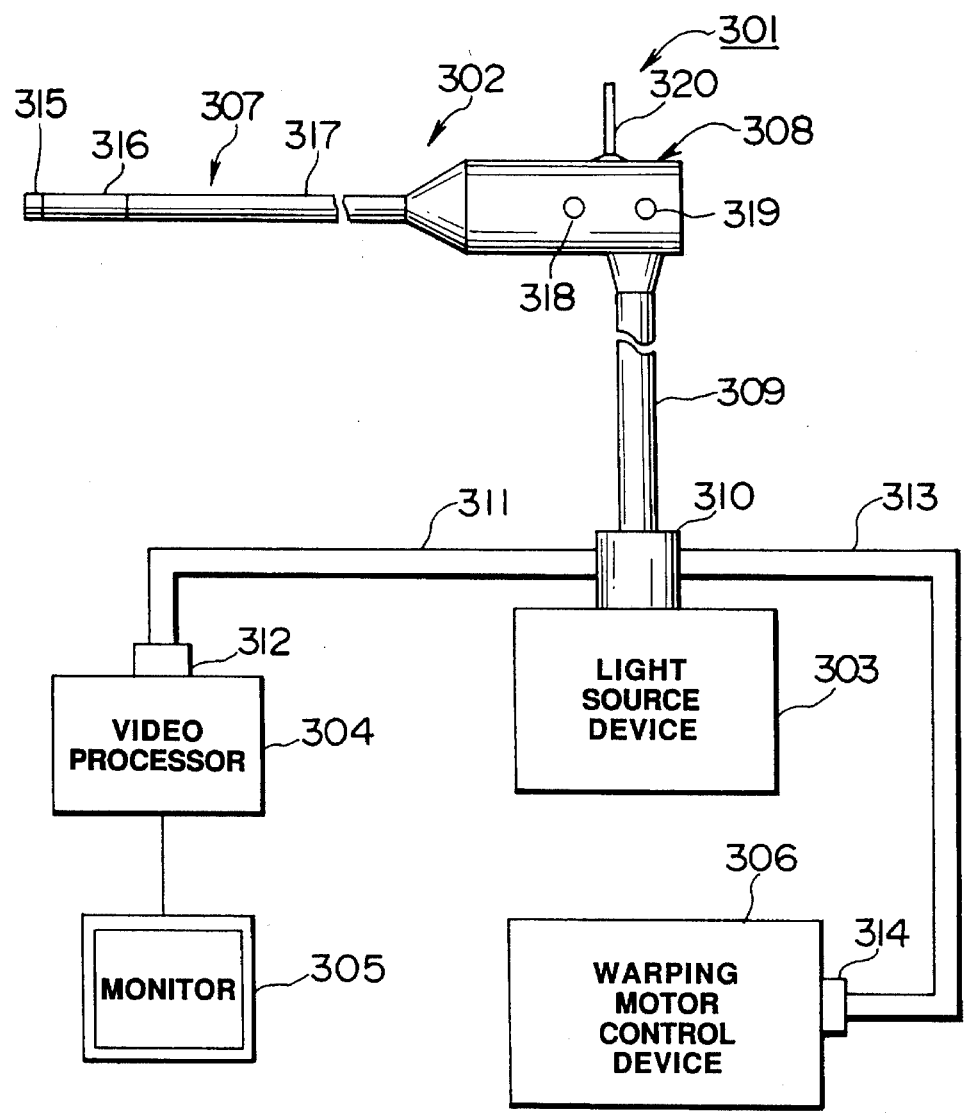
FIGS. 1 to 8 illustrate a first embodiment of the present invention, where
Figure 2:
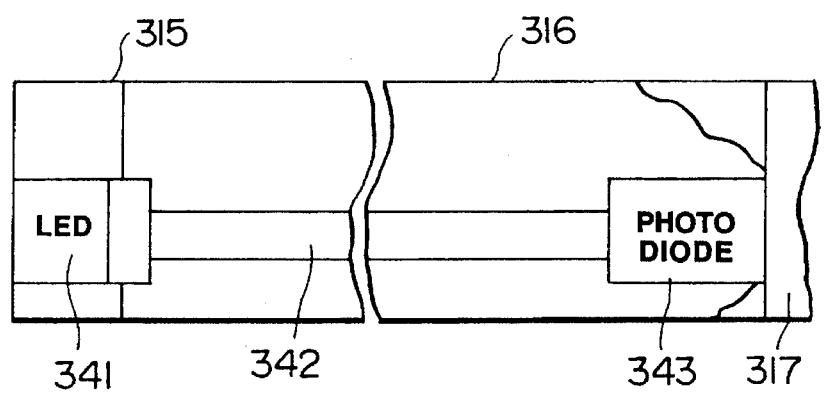
Figure 3:
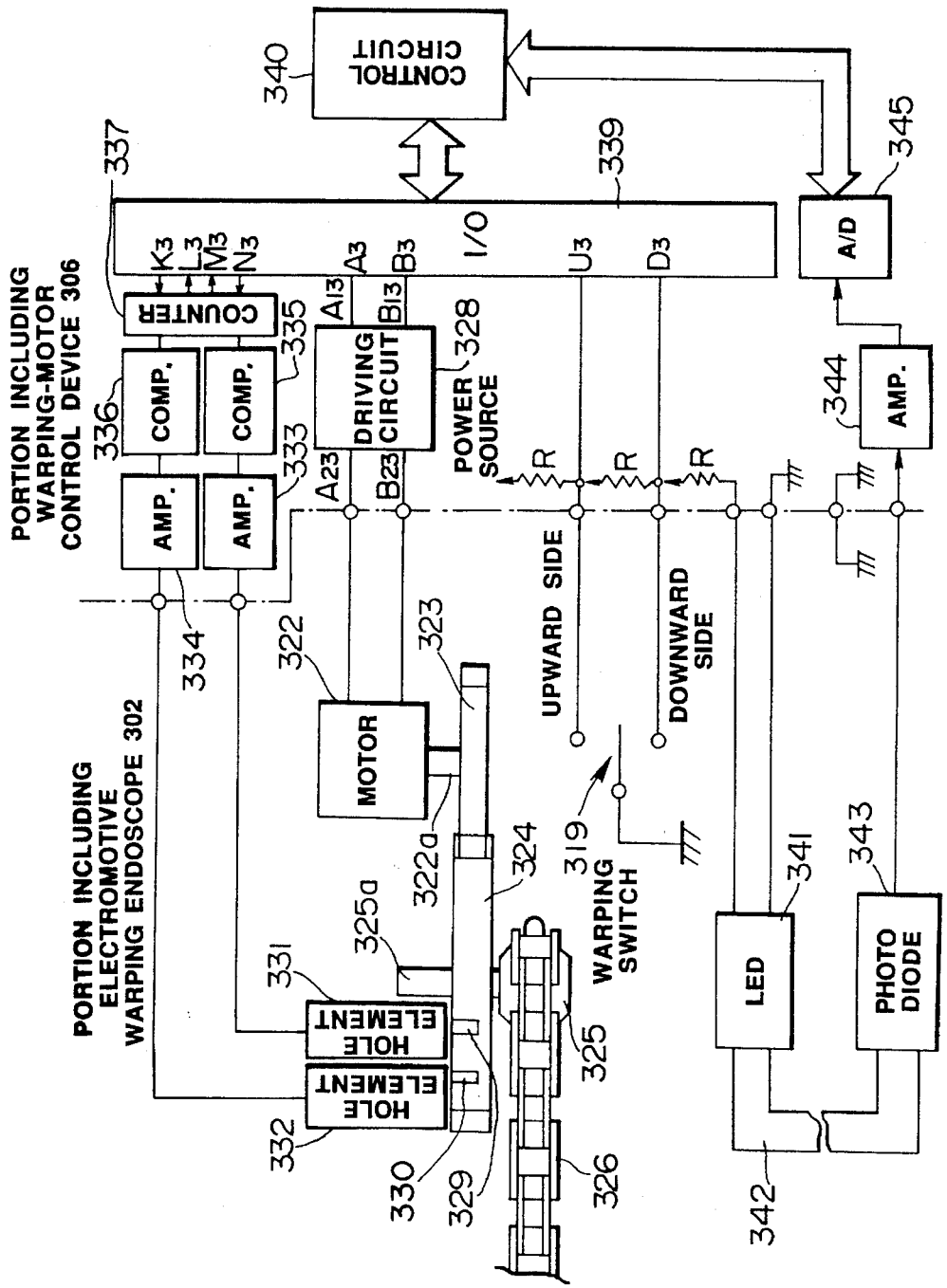
Figure 4:
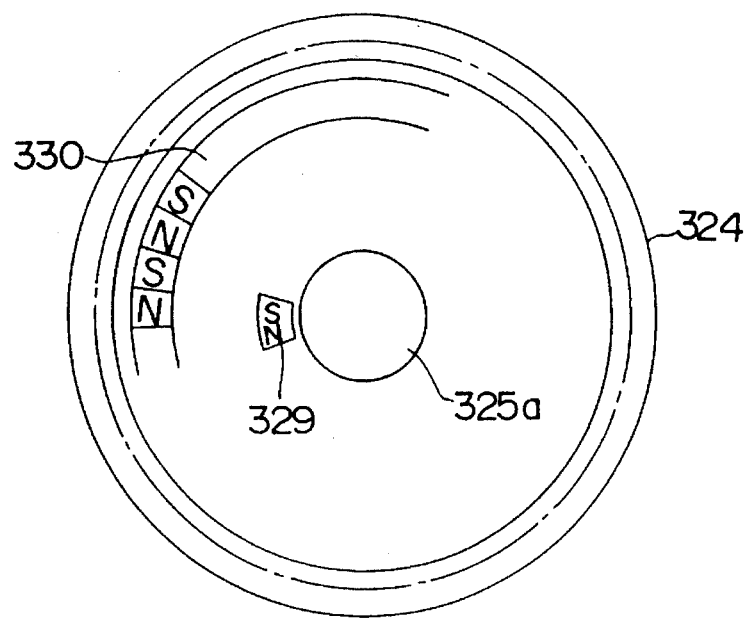
Figure 5:
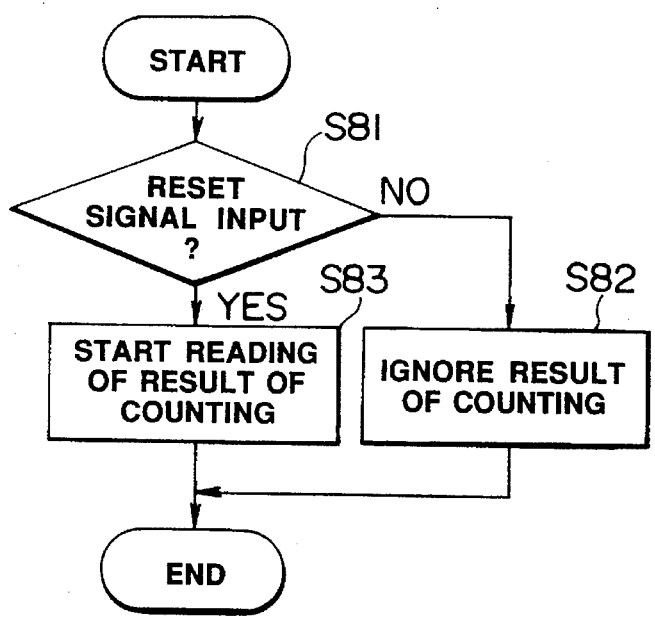
Figure 6:
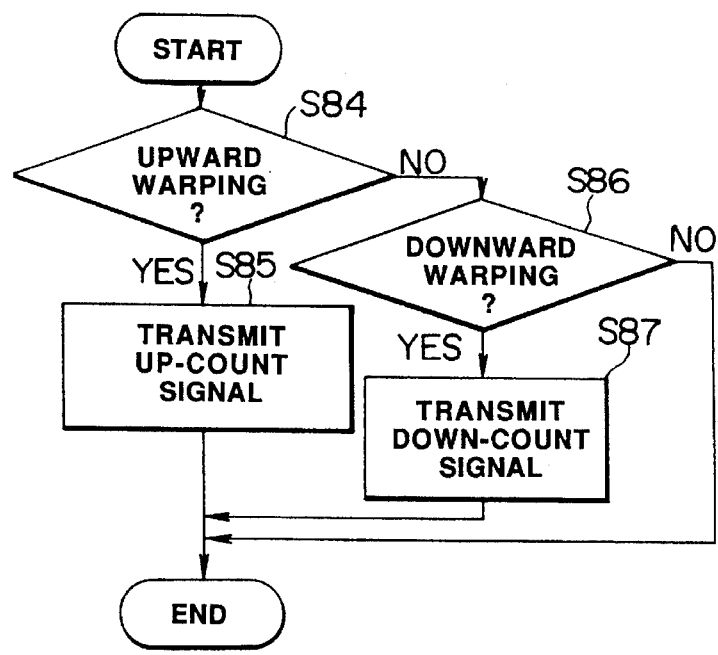
Figure 7:
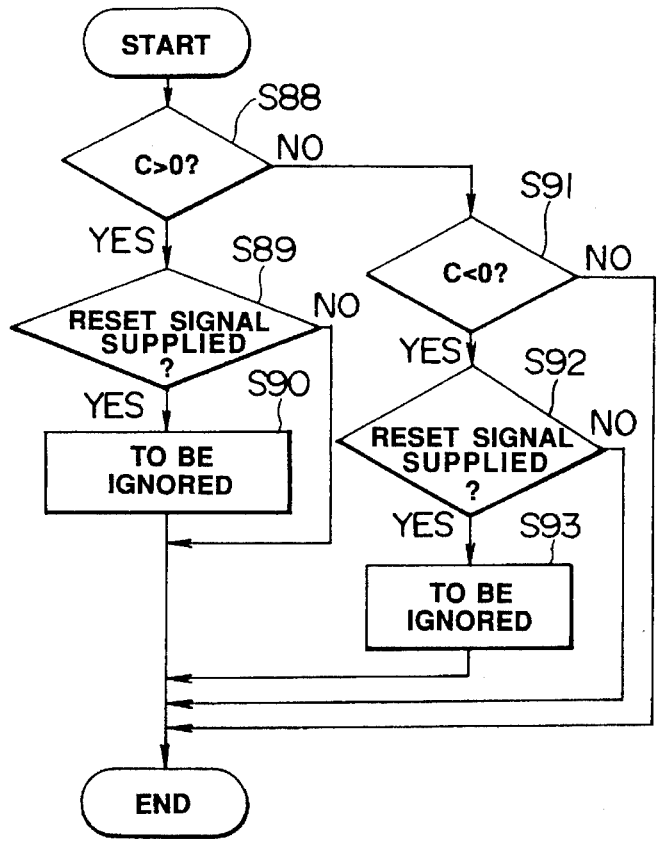
Figure 8:
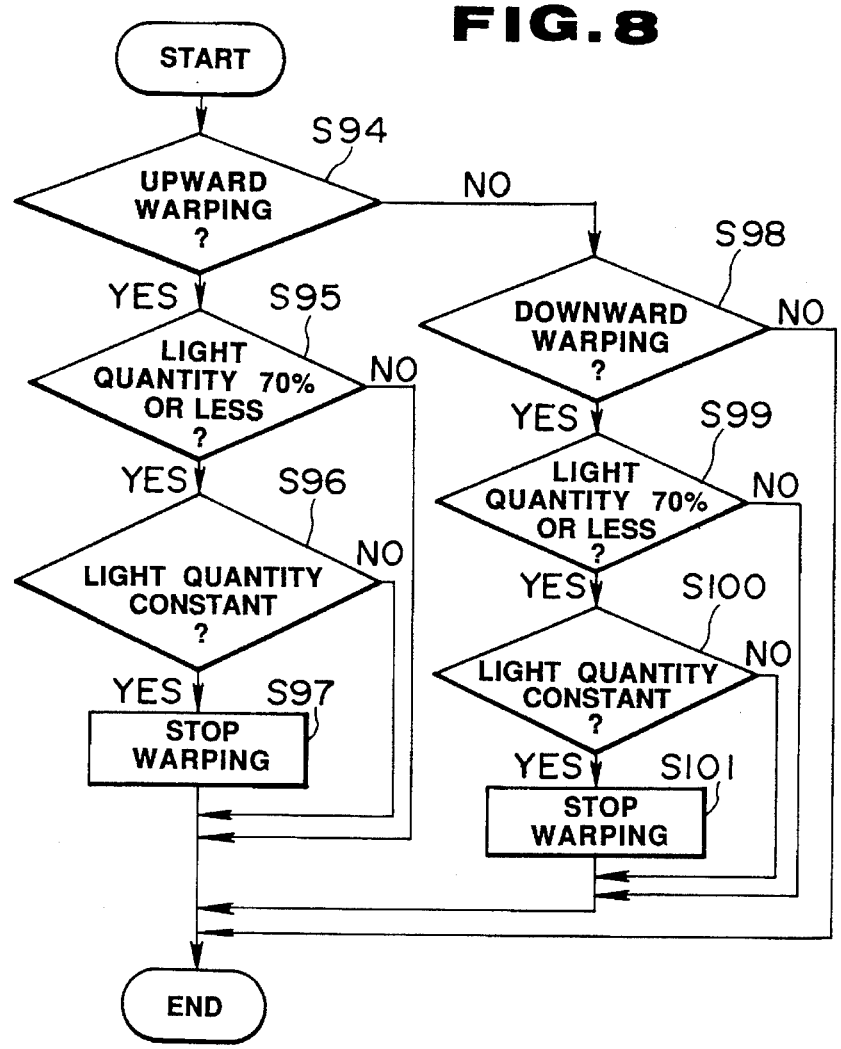

FIGS. 1 to 8 illustrate a first embodiment of the present invention. FIG. 1 illustrates the overall structure of an EM, FIG. 2 is a cross-sectional view which illustrates an insertion portion of the endoscope, FIG. 3 is a block diagram which illustrates the electromotive warping type endoscope apparatus including its essential portion, FIG. 4 is a structural view which illustrates a driven gear having magnetic poles therein, FIG. 5 is a flow chart which illustrates the initial operation to be performed at the time of controlling the warp; FIG. 6 is a flow chart which relates to warping direction recognition and its instruction, FIG. 7 is a flow chart which illustrates the warp control to be performed in order to obtain a predetermined angle of warping and FIG. 8 is a flow chart which illustrates the warp control which relates to a process to be performed in a dangerous state.

FIG. 1 illustrates an electronic type electromotive warping type endoscope apparatus 301. The electronic type electromotive warping type endoscope apparatus 301 has an electronic type electromotive warping type endoscope 302 having a solid-state image sensing device, a light source device 303 for supplying illuminating light to the electronic type electromotive warping type endoscope 302, a video processor 304 for processing signals transmitted from the electronic type electromotive warping type endoscope 302, a monitor 305 for receiving video signals transmitted from the video processor 304 so as to display an image of a subject and a curving-motor control device for controlling warping of a warp-enabled portion 316 provided for an insertion portion 307 of the electronic type electromotive warping type endoscope 302.

The electronic type electromotive warping type endoscope 302 comprises the insertion portion 307, an operation portion 308 and a universal cord 309. The insertion portion 307 is composed of a leading structural portion 315, a warp-enabled portion which can be warped and a flex-tube portion 317. The operation portion 308 has an air/water supply button 318, a suction button 319 and a warping-operation switch portion 320. When the warping-operation switch portion 320 is operated, the warp-enabled portion 316 is vertically warped.

A connector 310 arranged to be detachable from the light source device 303 is disposed at the end portion of the universal cord 309. A video processor cord 311 and a warping motor control unit cord 313 are extended from the side portion of the connector 310. A connector 312 to be detachably connected to the video processor 304 is fastened to the end portion of the video processor cord 311. Furthermore, a connector 314 to be detachably connected to the warping-motor control device 306 is fastened to the end portion of the warping-motor control device cord 313.

FIG. 2 schematically illustrates the inside portion of the leading structural unit 315 and that of the warp-enabled portion 316. The warp-enabled portion 316 includes a rubber fiber 342. The rubber fiber 342 has flexibility and is capable of transmitting light. The rubber fiber 342 is arranged in such a manner that the light quantity is damped in inverse proportion to the angle of the rotation. Light emitted from an LED 341 disposed in the leading structural unit 315 is caused to be incident on an end portion of the rubber fiber 342. A photodiode 343 is disposed in another end portion of the rubber fiber 342, the photodiode 343 being arranged to receive light emitted from the LED 341.

The electronic type electromotive warping type endoscope 302 is electrically connected to a warping-motor control unit 306 as shown in FIG. 3.

The operation portion 308 of the electronic type electromotive warping type endoscope 302 includes a power source, for example, a DC motor 322 for warping the warp-enabled portion 316. The DC motor 322 has a shaft 322a to which a drive gear 323 is secured. A driven gear 324 to be engaged to the drive gear 323 has a sprocket 325 secured thereto. A chain 326 is rotatively fastened to the sprocket 325. Two end portions of the chain 36 are respectively connected to end portions of two warping operation wires (omitted from illustration) while interposing two connection members (omitted from illustration).

FIG. 4 illustrates the driven gear 324.

The driven gear 324 has a band 329 on its side opposing the chain 326 and as well as adjacent to a shaft 325a of the sprocket 325, the band being polarized into a pair of poles composed of N and S poles. The band 329 is located in such a manner that it faces a hole element to be described later when the warp-enabled portion 316 is in a straight state (it is not warped vertically), A ring 330 polarized into N and S poles is disposed in the outer circumferential portion of the driven gear 324. The ring 330 is polarized into a plurality of N and S poles and has 36 pairs, each composed of one N pole and one S pole, in its circumference.

The hole elements 331 and 332 respectively convert the magnetic change caused from the rotation of the band 329 and that of the ring 330 into an electric signal. The hole element 331 acts to detect the fact that the warp-enabled portion 316 is straight, while the hole element 332 acts to detect the angle and the direction in which the warp-enabled portion 316 is warped.

The warping-motor control device 306 has a drive circuit 328 for driving a DC motor 322 included in the operation portion 308, amplifiers 333 and 334 for amplifying output signals transmitted from the hole elements 331 and 332, comparators 335 and 336 for waveform-shaping the output signals transmitted from the amplifiers 333 and 334 into rectangular waves and a counter 337 for counting an output signal transmitted from the comparator 336 and also transmitting an output signal transmitted from the comparator 335 to an input/output interface (hereinafter abbreviated to "I/O") 339, the output transmitted from the comparator 335 being transmitted as a reset signal.

The I/O 339 is connected to the counter 337 and has a terminal M3 for receiving a signal transmitted from the counter 337, a terminal N3 for transmitting an up-count signal, a terminal K3 for transmitting a down-count signal and a terminal L3 for receiving a reset signal.

The counter 337 receives an output signal transmitted from the hole element 332 and formed into a binary signal by the comparator 335 so as to transmit it as the reset signal to the control circuit 340 via the terminal L3.

Furthermore, the counter 337 receives an output signal transmitted from the hole element 332 and formed into a binary signal by the comparator 335 so as to transmit a count value to the control circuit 340 via the terminal M3.

The output signal transmitted from the comparator 335 becomes a pulse signal which corresponds to an angle of rotation. Furthermore, the counter 337 increases the count value in accordance with an instruction made by the up-count signal transmitted from the control circuit 340, the instruction being made with the level, for example, the high level (hereinafter abbreviated to "H") of the up-count signal. On the contrary, the counter 337 decreases the count value in accordance with an instruction made by the down-count signal transmitted from the control circuit 340, the instruction being made with the level, for example, the low level (hereinafter abbreviated to "L") of the down-count signal.

The control circuit 340 is able to recognize a straight state when it receives the reset signal supplied from the counter 337. Furthermore, the control circuit 340 recognizes the direction and the angle of the warp from the count value and sets flag C in such a manner that it increases/decreases flag C according to increase/decrease of the count value. The control circuit 340 transmits the up-count signal via the terminal N3 in accordance with the angle of the warp recognized from the aforesaid count value, while the same transmits the down-count signal to the counter 337 via the terminal K3.

The control circuit 340 makes both of the levels of the up-count signal and that of the down-count signal to, for example, "L" at the time of the initial operation when the power supply is commenced. At this time, the counter 337 presets the count value in response to a signal transmitted from the comparator 335.

In a case where the endoscope is of a type having the driven gear 324 which is rotated a plurality of times until the maximum warp angle is made, the control circuit 340 ignores the reset signal supplied from the counter 337.

The warping-motor control device 306 has an amplifier 344 for amplifying an output signal detected by the photodiode 343 and an A/D converter 345 for A/D-converting an output signal transmitted from the amplifier 344 so as to transmit a digital signal to the control circuit 340.

Terminals A3 and B3 of the I/O 339 are connected to the drive circuit 328, while terminals U3 and D3 are connected to the warping-operation switch 320 and are pulled-up via resistors R.

Output signals transmitted from the warping-operation switch 320 and the counter 337 are supplied to the control circuit 340 via the I/O 339. An output signal from the control circuit 340 is transmitted to the drive circuit 328 via the I/O 339. The drive circuit 328 rotates the DC motor 322 with predetermined voltage.

Although description is made about a structure in which the warping is made in only the vertical direction in order to simplify the description, the warping may be made in four directions. In this case, another system comprising the warping mechanism composed of the chain 326 and the gear and the like, the hole elements 331 and 332, the motor 322 and the warping-operation switch 320 must be provided.

The operation of this embodiment will now be described with reference to flow charts shown in FIGS. 5 to 8.

When power is supplied to the warping-operation motor control device 306, a high level signal is supplied to the terminal U3 of the I/O 339 and a high level signal is supplied to the terminal D3.

A low level signal is abbreviated to "L" and the high level signal is abbreviated to "H". In addition, the signals to be supplied/transmitted from the I/O 339 are expressed in such a manner that U3="H" and D3="H".

Since the control circuit 340 inputs/outputs U3="H" and D3="H", A3=L and B3=L are transmitted from the I/O 339 to the drive circuit 328. As a result, a stationary state of the warp-enabled portion 316 is maintained.

FIG. 5 is a flow chart which illustrates only the first time operation to be performed when the power is supplied.

The warping-operation switch 320 is operated in the upward or downward direction. At this time, if the reset signal is not supplied to the terminal L3 one time in step S81, the control circuit 340 ignores the count value in step S82.

If the reset signal is supplied one time in step S81, the control circuit 340 resets flag C included therein in step S83. Furthermore, the control circuit 340 starts reading the count value of the counter 337. As a result of this operation, the state where the warp-enabled portion 316 is straight is recognized. At this time, the counter 337 presets a predetermined count value.

When the warping-operation switch 320 is operated in the upward direction, U3="L" and D3="H" are supplied to the I/O 339. Since the control circuit 340 receives/transmits U3="L" and D3="H" it transmits A3="H" and B3="L" from the I/O 339 to the drive circuit 328. That is, since A13="H" and B13= "L" an electric current flows from A23 to B23 As a result, the DC motor 322 is rotated in the upward direction. When the DC motor 322 is rotated, the drive gear 323 is rotated and the driven gear 324 is rotated. As a result, the sprocket 325 is rotated and the chain 326 is pulled. When either side of the chain 326 is pulled, one of the wires (omitted from illustration) is pulled. On the other hand, the other wire is slackened. As a result, the warp-enabled portion 316 is warped in the upward direction.

When the warping-operation switch 320 is operated in the downward direction, U3="H" and D3="L" are supplied to the I/O 339. Since the control circuit 340 receives/transmits U3="H" and D3="L", the I/O 339 transmits A3="L" and B3="H" to the drive circuit 328 That is, since A13="L" and B13="H" an electric current flows from B23 to A23. As a result, the DC motor 332 is rotated in the downward direction. When the DC motor 322 is rotated, the drive gear 333 is rotated and the driven gear 324 is rotated. As a result, the sprocket 325 is rotated and the chain 326 is pulled. As a result, the wire is pulled in the downward direction opposing the upward direction.

The driven gear 324 has the ring 330 polarized into N and S poles, the ring 330 polarized into the N and S poles having 36 pairs of poles each composed of N and S poles. The structure is arranged in such a manner that the driven gear is warped by, for example, about 10° during the time from a moment at which the hole element 332 detects one pair of the N and S poles to a moment at which the same detects the next pair of the N and S poles.

The angle of the warp is not limited to the aforesaid degree of about 10°. Furthermore, the number of the pairs each composed of the N and S poles of the ring polarized into the N and S poles is not limited to 36.

A signal detected by the hole element 332 is amplified by the amplifier 334, and then it is converted into the rectangular wave by the comparator 336, the rectangular wave being then transmitted to the counter 337.

In a case where the warping-operation switch 320 is operated in the upward direction, the control circuit 340 discriminates in step S84 shown in FIG. 6 that the upward directional warp is instructed in accordance with the inputs U3="H" and D3="L" made to the I/O 339. Then, it transmits the up-count signal to the counter 337 in step S85.

In a case where the warping-operation switch 320 is operated in the downward direction, the control circuit 340 discriminates in step S86 shown in FIG. 6 that the downward directional warp is instructed in accordance with the inputs U3="L" and D3="H" made to the I/O 339. Then, it transmits the down-count signal to the counter 337 in step S87.

The counter 337 increases/decreases the count of the number of the pulses transmitted from the comparator 336 via the terminal M3 of the I/O 339 in response to the up/down count signal transmitted from the control circuit 340. Furthermore, the counter 337 transmits the count value to the control circuit 340 via the I/O 339.

The control circuit 340 increases/decreases flag C in accordance with the increase/decrease of the count value.

If flag C>0 in step S88 shown in FIG. 7, the control circuit 340 detects in step S89 whether or not the reset signal has been supplied. If the reset signal is supplied in step S90, the control circuit 340 ignores the reset signal. That is, the control circuit 340 does not reset flag G in a state where the upward directional warp is made.

The reset signal is transmitted from the counter 337 whenever the band 329 composed of the pair of N and S poles passes through the hole element 331. However, in the aforesaid case where the endoscope is a type arranged in such a manner that its driven gear 324 rotates plural times until the maximum angle of warp is made, the position at which the reset signal is detected is not necessarily the position at which the warp-enabled portion 316 is straight. Accordingly, this embodiment is arranged in such a manner that whether or not the warp-enabled portion 316 is in an intermediate state (a state where it is not straight) of the warping operation is discriminated in accordance with the polarity of flag C.

As a result of the operations in steps S88 to S90, flag C is not reset at positions at which the warp-enabled portion 316 is not straight. Therefore, an erroneous recognition that the warp-enabled portion is straight can be prevented. If no reset signal is supplied in step S89, for example, if the warp-enabled portion 316 is warped, flag C is increased or decreased.

Steps S91 to S93 are included in a flow chart for a state in which the downward warp is made and are the same as the operations to be performed in the case where the upward warp is made. Therefore, their descriptions are omitted here.

If a negative discrimination is made in step S91, it means that the straight state (C=0) or the warp-enabled portion 316 is stopped. Therefore, the increase or decrease of flag C is performed usually in accordance with the ensuing warping operation instructed.

The warp-enabled portion 316 has the rubber fiber 342, an output signal transmitted from the photodiode 343 is amplified by the amplifier 344 and is subject to the A/D conversion in the A/D converter 345 so as to transmit the digital signal to the control circuit 340. The control circuit 340 always supervises the light quantity received by the photodiode 342. The control circuit 340 discriminates the light quantity from the photodiode 340 is 100% at the position at which the reset signal is received, that is, in the state where the warp-enabled portion 316 is straight.

Since the liquid quantity is damped according to the angle of the warp in a state where the warp-enabled portion 316 is warped, the control circuit 340 is able to detect whether or not the warp-enabled portion 316 comes in contact with the subject to be inspected by supervising the change in the light quantity.

In a case where the upward warp is made in step S94 shown in FIG. 8, the light quantity is 70% or less in step S95 and the change in the light quantity is ±1% or less although an output is made from the hole element 332 in step S96, a discrimination is made that it is dangerous because the warp-enabled portion 316 comes in contact with the body wall or the like. Therefore, the warping operation is stopped in step S97. The aforesaid control is given priority to the instruction of the warping-operation switch portion 320.

The reason why the discrimination is made whether or not the light quantity is 70% or less lies in that the rubber fiber 342 has not the linear characteristic. In particular, since the light quantity change is insufficient in a case where a small angular warp is made from the straight state, the discrimination that the state where no light quantity change is detected is a dangerous state cannot always be made after a state in which the light quantity change has been made relatively considerable.

Steps S98 to S101 are included in a flow chart for a state in which the downward warp is made and are the same as the operations to be performed in the case where the upward warp is made. Therefore, their descriptions are omitted here.

If a negative discrimination is made in step S98, it means that the warp-enabled portion 316 is straight or the same is stopped.

The change in the light quantity at which the warping operation is stopped is not limited to ±1%. Furthermore, the LED 341 is replaced by a light guide fiber branched into two sections either of which is connected to the rubber fiber 336.

According to this embodiment, if the quantity of light received by the photodiode is not changed although the warp-enabled portion is warped, a discrimination is made that it is a dangerous state because it comes in contact with, for example, the body wall and therefore the warping operation is stopped. As a result, according to this embodiment, the warping operation feasibility can be improved and also the safety can be improved.

As the control of the warping velocity, the warping velocity may be decelerated or the warp enabled portion may be warped in a different direction, for example, in an opposing direction to the direction realized (instructed) by means of the warping-operation switch portion 320 as an alternative to stopping the warping operation.

Figure 9:
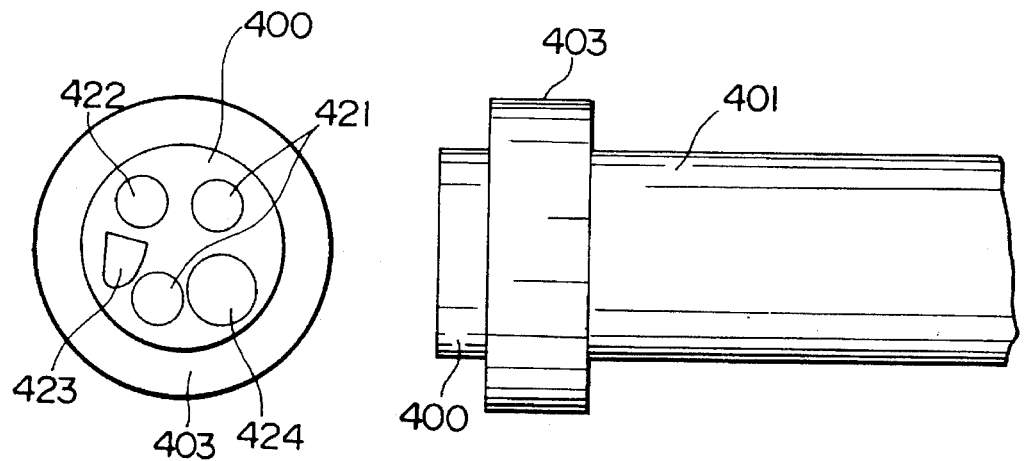
FIGS. 9 to 14 illustrate a second embodiment of the present invention, where
Figure 10:
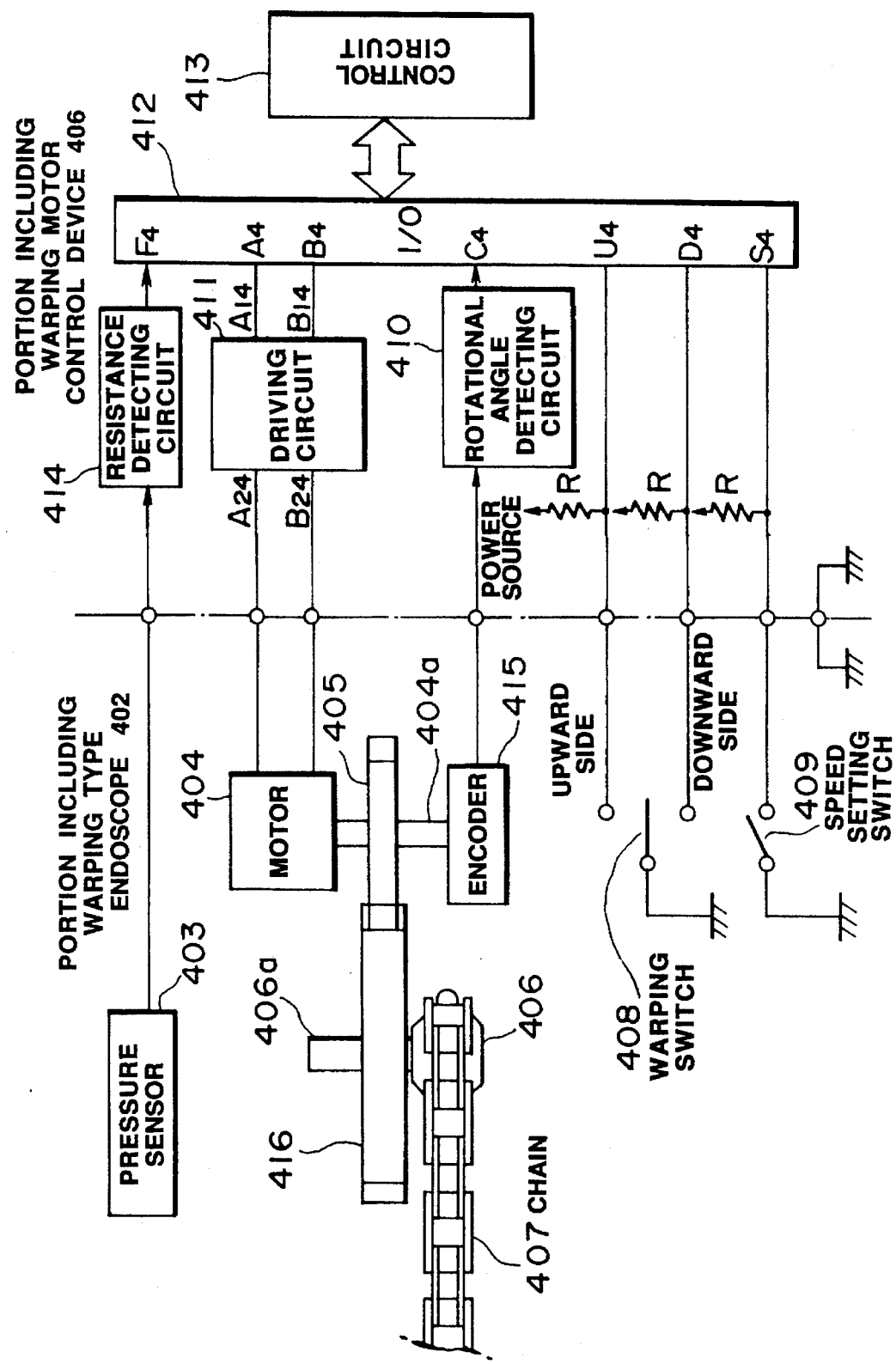
Figure 11:
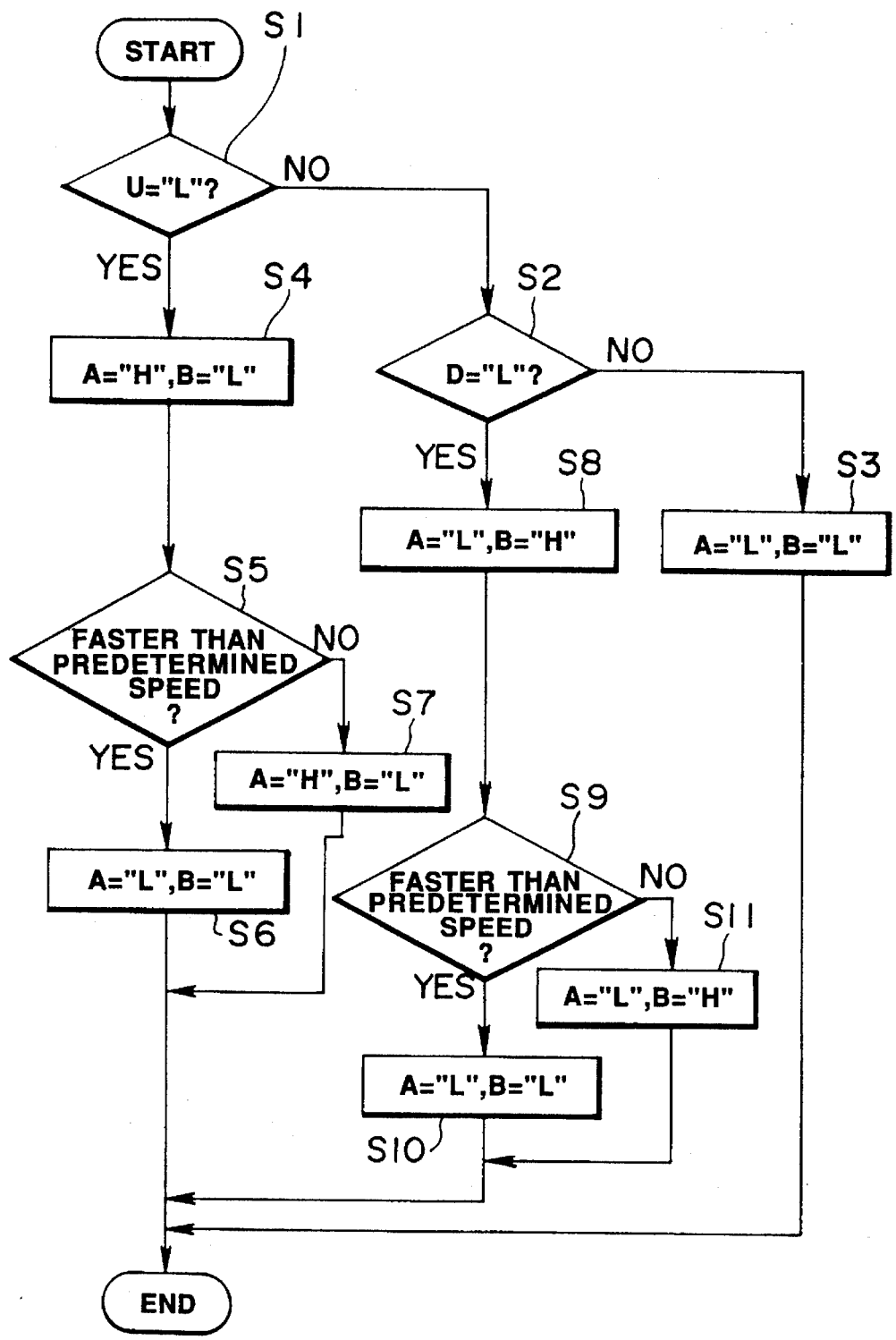
Figure 12:
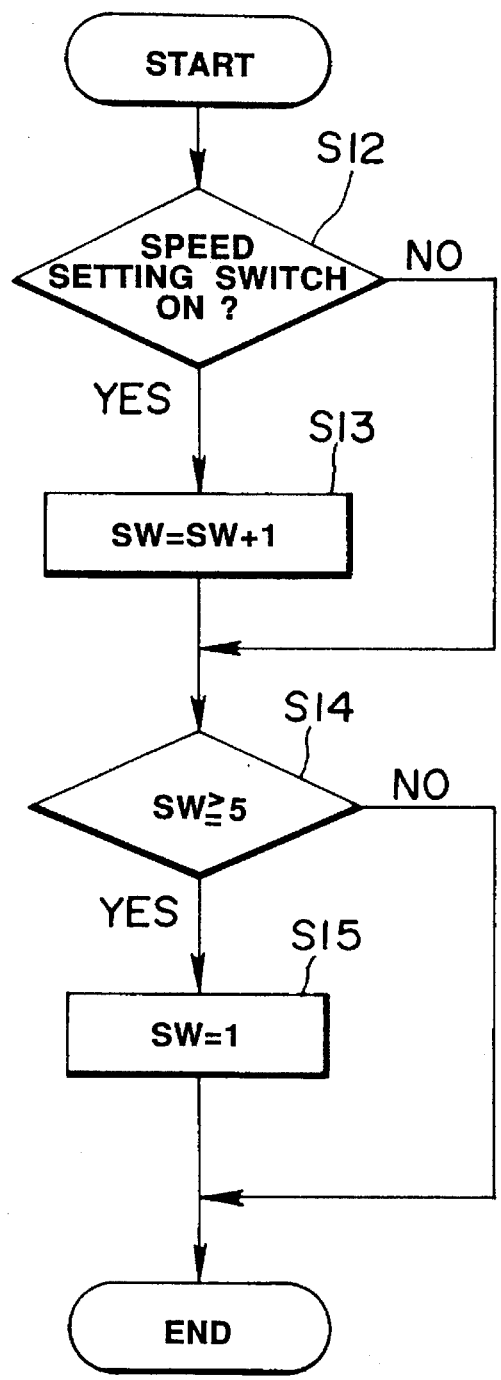
Figure 13:
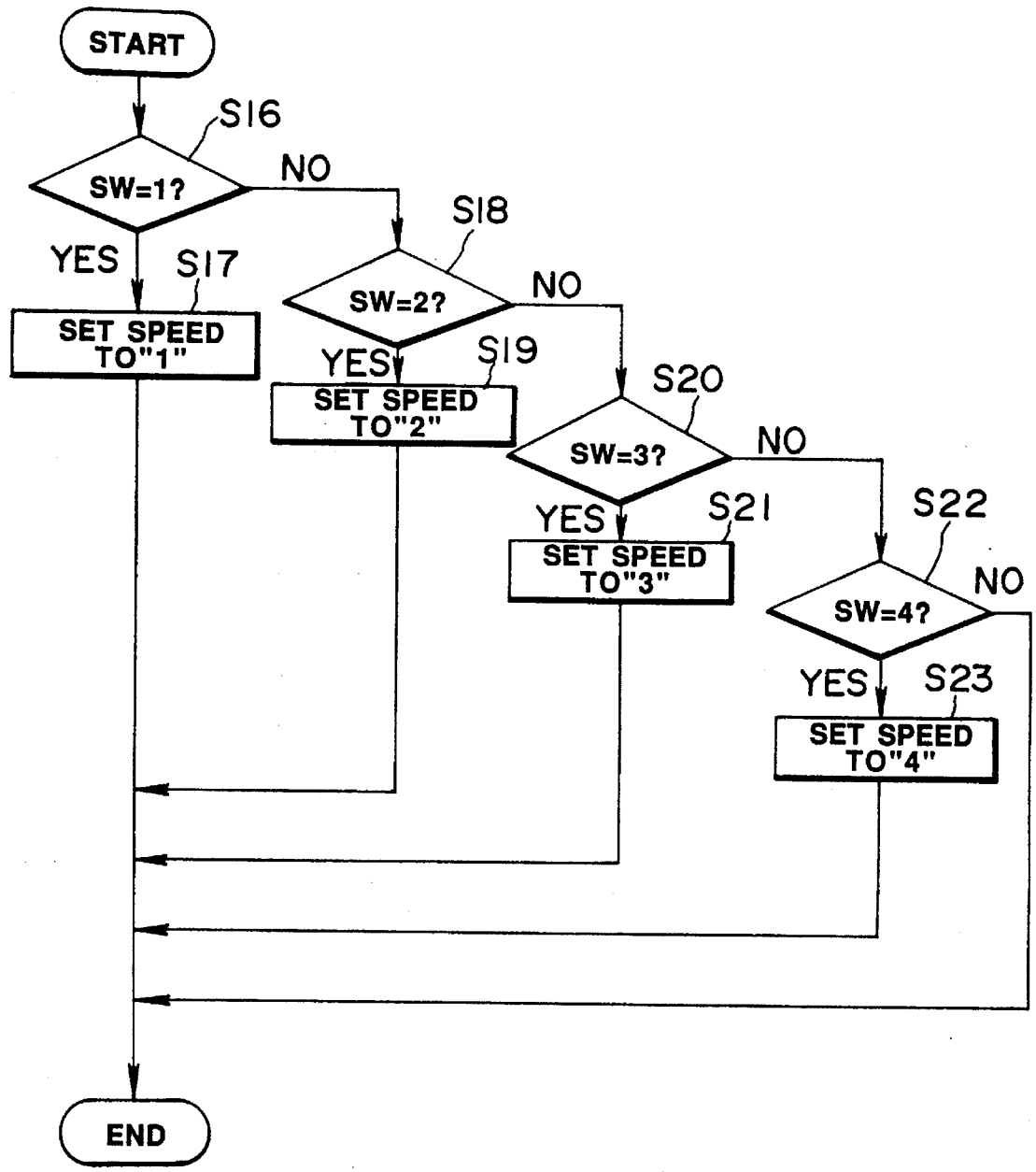
Figure 14:
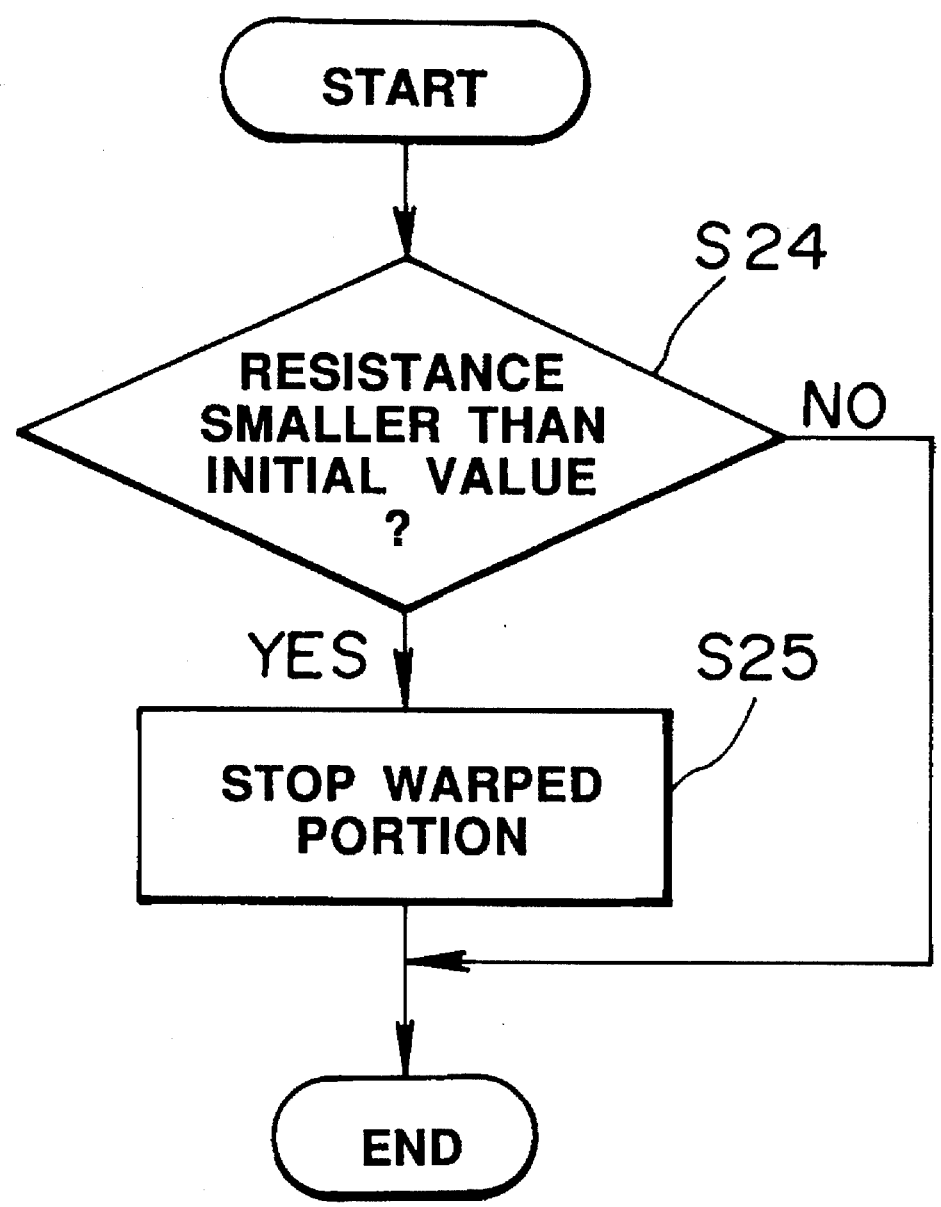

FIGS. 9 to 14 illustrate a second embodiment of the present invention. FIG. 9 illustrates the shape of the leading portion of the endoscope, FIG. 10 is a block diagram which illustrates an essential portion of the electromotive warping type endoscope apparatus, FIG. 11 is a flow chart which illustrates the operations for controlling the warping operation and the warping velocity, FIG. 12 is a flow chart which illustrates the operation for setting a velocity setting flag, FIG. 13 is a flow chart which illustrates the operation of switching the warping velocity and FIG. 14 is a flow chart which illustrates the operation for emergency-stopping the warp-enabled portion.

The electromotive warping type endoscope according to the first embodiment is arranged in such a manner that the contact with the subject to be inspected is detected from the change in the quantity of light which has transmitted the rubber fiber and the angle of the warp and the straight state are detected by the hole element. However, this embodiment is arranged in such a manner that the contact with the subject to be inspected is directly detected by a pressure sensor and the angle of warp is detected by an encoder.

The electromotive warping type endoscope according to this embodiment is structured substantially the same as the electromotive endoscope apparatus 301 shown in FIG. 1. An endoscope 402 shown in FIG. 9 is employed in place of the endoscope 302 and a warping-motor control device 406 shown in FIG. 10 is employed in place of the warping-motor control device 306. Since the overall structure of the apparatus is the same as that according to the first embodiment, illustration and description are omitted here.

FIG. 9 illustrates a leading structure 400 and the warp-enabled portion 401 which are disposed in the leading portion of the insertion portion of the electronic endoscope 402. An annular pressure sensor 403 is secured to the circular outer surface of the leading unit 400. Referring to FIG. 9, reference numeral 421 represents an illuminating window, 422 represents an observing window, 423 represents an air and water supply nozzle and 424 represents a forceps channel port.

FIG. 10 illustrates an electrical connection between an operation portion of the electromotive warping type endoscope 401 and the warping-motor control device 406 and also shows a portion of a warping mechanism.

The operation portion of the electromotive warping type endoscope 402 includes a DC motor 404 as driving means for warping the warp-enabled portion 401. A rotational shaft 404a of the DC motor 404 has a drive gear 405 at an intermediate portion thereof. A driven gear 416 to be engaged to the drive gear 405 is secured to a shaft 406a of a sprocket 406. A chain 407 is rotatively fastened to the sprocket 406. End portions of two wires (omitted from illustration) are connected to the chain 407 by two connection members (omitted from illustration). The other end portions of the two wires are inserted into a plurality of joint blocks included in the warp-enabled portion 401 and rotatively combined with each other, the wires being secured to the leading joint blocks. The other end portions of the wires are secured to the leading unit 400. As a result, the aforesaid wires are pulled/slackened when the DC motor 404 is rotated, causing the warp-enabled portion 401 to be warped.

The rotational shaft 404a of the DC motor 404 has, at the leading portion thereof, an absolute-type encoder 415 for the purpose of detecting the rotational angle of the DC motor 404.

The warping-motor control device 406 comprises a drive circuit 411 for rotating the DC motor 404, a rotational angle detecting circuit 410 for converting an output signal transmitted from the encoder into data about an angle so as to transmit data, a control circuit serving as control means for controlling the warping operation and the warping velocity and a resistance detecting circuit 414 for detecting an output signal transmitted from the pressure sensor 403.

The warping-motor control device 406 comprises the drive circuit 411, the rotational angle detecting circuit 410, the resistance detecting circuit 414, a warping operation switch 408 and a velocity setting switch 409 each disposed in the operation portion of the endoscope 402 and an I/O 412 disposed between these elements and the control circuit 413 and interfacing input and output of signals.

The control circuit 413 and the I/O 412 are connected to each other by a bus line. The warping operation switch 408 is a switch for upwards/downwards warping the warp-enabled portion 401 and has a common terminal grounded and an up-terminal connected to a terminal U4 of the I/O 412. Furthermore, an end of a resistor R, another end portion of which is connected to a power source, is connected to the upward-terminal. A down-terminal of the warping operation switch 408 is connected to a terminal D4 of the I/O 412. Furthermore, an end portion of a resistor R, another end portion of which is connected to the power source, is connected to the downward-terminal.

An end portion of the velocity setting switch 409 is grounded, while another end portion is connected to a terminal S4 of the I/O 412. Furthermore, an end portion of a resistor R, another end portion of which is connected to the power source, is connected to the end portion of the velocity setting switch 409.

The drive circuit 411 is composed of, for example, a CPU which receives a control signal via terminals A4 and B4 of the I/O 412. On the other hand, the rotational angle detecting circuit 410 transmits data about the angle to the control circuit 413 via a terminal C4 of the I/O 412. The resistance detecting circuit 414 transmits data about the resistance value to the control circuit 413 via a terminal F4 of the I/O 412.

The control circuit 413 controls the drive circuit 411 via the I/O 412 when the warping-operation switch 409 is operated so as to control the start/stop of the warp-enabled portion 401 and also controls the warping direction.

The control circuit 413 converts data about the angle obtained by the rotational angle detecting circuit 410 into data about the warping velocity of the warp-enabled portion 401 so as to always supervise the warping velocity of the warp-enabled portion 401. Furthermore, the control circuit controls the warping velocity of the warp-enabled portion 401 in accordance with the operation of the velocity setting switch 409. In addition, the control circuit 413 always supervises the data about the resistance value detected by the resistance detecting circuit 414.

In order to simplify the description, the warping direction is limited to the two directions, that is, the upward and downward directions. The warping may be made in four directions composed of the aforesaid directions and additional right and left directions. In this case, another system composed of the warping mechanism comprising the chain 407 and the gear, the DC motor 404 and the warping operation switch 408 must be used.

The operation of this embodiment will now be described with reference to flow charts shown in FIGS. 11 to 14.

When the power source for the warping-motor control device 406 is turned on, the levels of the terminals D4 and U4 of the I/O 412 are raised ("H"). As a result, the control circuit 413 discriminates that the state of stoppage has been realized and transmits low level signals ("L") to the terminals A4 and B4 of the I/O 412. The warp-enabled portion 401 maintains the state of stoppage.

When the warping operation switch 408 is operated in the upward direction, the level of the terminal U4 of the I/O 412 is lowered and that of the terminal D4 of the same is raised. In step S4 allowed to proceed as a result of a discrimination made in step S1, the control circuit 413 transmits a high level signal to the terminal A4 of the I/O 412 and a low level signal to the terminal B4 of the same. At this time, an electric current flows in the DC motor 404 in a direction from A24 to B24 shown in FIG. 10, so that the DC motor 404 is rotated in the upward direction. The rotation of the DC motor 404 pulls the chain 407 and the wire via the drive gear 405, the driven gear 416 and the sprocket 406. As a result, the warp-enabled portion 401 is warped in the upward direction.

The rotational angle detecting circuit 410 converts the output pulse detected by the encoder 415 into angle data so as to transmit it to the control circuit 413 via the terminal C4 of the I/O 412. The control circuit 413 converts angle data to velocity data denoting the warping velocity of the warp-enabled portion 401, and, in step S5, discriminates whether or not the value of velocity data is larger than a predetermined value, that is, whether or not the warping velocity is higher than a predetermined velocity to be described later. If an affirmative discrimination has been made, the control circuit 413 makes the rotation speed of the DC motor 404 constant by lowering the levels of both of the terminals A4 and B4 of the I/O 412 to stop the supply of the electric current to the DC motor 404 in step S6. If a negative discrimination has been made, that is, if the velocity is lower than the predetermined velocity, the control circuit 413 transmits a high level signal to the terminal A4 of the I/O 412 and a low level signal to the terminal B4 in step S7 to instruct the continuity of the upward directional rotation of the DC motor 404. As a result of a kind of the PWM (Pulse Width Modulation) control, the DC motor 404 is always rotated at constant speed.

When the warping operation switch 408 is operated in the downward direction, the level of the terminal U4 of the I/O 412 is raised and that of the terminal D4 is lowered. In step S8 allowed to proceed via steps S1 and S2, the control circuit 413 transmits a low level signal to the terminal A4 of the I/O 412 and a high level signal to the terminal B4. At this time, an electric current flow in the DC motor 404 in a direction from B24 to A24 shown in FIG. 10, so that the DC motor 404 is rotated in the downward direction. The rotation of the DC motor 404 pulls the chain 407 and the wire via the drive gear 405, the driven gear 416 and the sprocket 406. As a result, the warp-enabled portion 401 is warped in the downward direction.

By using velocity data similarly to the aforesaid case, the control circuit 413 discriminates whether or not the value of velocity data is larger than a predetermined value in step S9, that is, whether or not the warping velocity is higher than the predetermined velocity.

If an affirmative discrimination has been made, the control circuit 413 makes the rotation speed of the DC motor 404 constant by lowering the levels of both of the terminals A4 and B4 of the I/O 412 to stop the supply of the electric current to the DC motor 404 in step S10. If a negative discrimination has been made, that is, if the velocity is lower than the predetermined velocity, the control circuit 413 transmits a low level signal to the terminal A4 of the I/O 412 and a high level signal to the terminal B4 to instruct the continuity of the downward directional rotation of the DC motor 404. As a result of a kind of the PWM (Pulse Width Modulation) control, the DC motor 404 is always rotated at constant speed.

If the warping operation switch 408 is not operated, that is, if the switch is at the neutral position, the level of the terminal U4 of the I/O 412 and that of the terminal D4 of the same are high, the control circuit 413 sets the levels of the outputs from the terminals A4 and B4 of the I/O 412 in step S3 allowed to proceed via steps S1 and S2. As a result, no electric current flows to the DC motor 404, causing the state of stoppage to be maintained and therefore the stoppage of the warp-enabled portion 401 to be maintained.

FIGS. 12 and 13 are flow charts which illustrate a process to be performed by the control circuit 413 in a case where the velocity setting switch 408 is operated.

When power is supplied to the warping-motor control device 406, flag SW for setting the velocity in the control circuit 413 is first set to "1". When the velocity setting switch 409 is switched on in step S12 shown in FIG. 12, flag SW is increased by "1" in step S13 whenever the same is switched on. If the velocity setting switch 409 is not switched on, flag SW maintains the present state until the velocity setting switch 409 is switched on. In step S14, whether or not flag SW≧5 is discriminated. If it is 5 or more, flag SW is again returned to "1" in step 15. That is, flag SW is increased by one whenever the velocity setting switch 409 is switched on so that the indication of flag SW is always in a range from "1" to "4".

If flag SW is "1" in step S16 shown in FIG. 13, the velocity is set to "1" in step S17. The velocity which is set in this step is a predetermined velocity which serves as a reference for an evaluation in steps S5 and S9 in FIG. 11. If flag SW is "2" in step S18, the velocity is set to "2" in step S19. If flag SW is "3" in step S20, the velocity is set to "3" in step S21. If flag SW is "4" in step S22, the velocity is set to "4" in step S23.

A flow chart shown in FIG. 14 illustrates the operation of controlling the warping velocity to be performed when a dangerous state in which the warp-enabled portion of the endoscope 402 comes in contact with the subject to be inspected.

The control circuit 413 always supervises the change in the resistance value of the pressure sensor 403 detected by the resistance detecting circuit 414. When the warp-enabled portion 401 of the endoscope 402 is warped, the pressure sensor 403 sometimes comes in contact with the body wall of the subject to be inspected. If the pressure sensor 403 comes in contact with the body wall of the subject to be inspected or the like, the resistance value of the pressure sensor 403 is decreased.

In the aforesaid state, the resistance detecting circuit 414 detects the change in which the resistance value of the pressure sensor 403 is decreased in step S24 to transmit the result of the detection to the control circuit 413. The control circuit 413 discriminates that it is dangerous if the detected resistance value is smaller than a predetermined resistance value. Then, in step S25, the control circuit 413 causes the I/O 412 to transmit "L" from A4 and "L" from B4. As a result, the warp-enabled portion 401 is stopped. The aforesaid control is given priority to the instruction made with the warping operation switch 408.

If the resistance value is larger than the predetermined value in step S24, the present operation, for example, the upward warping operation, corresponding to the instruction made with the warping operation switch 408 is continued.

In step S25, control may be performed in such a manner that the setting velocity is lower than the set velocity "1" or less, for example, the half of the set velocity. The warp-enabled portion 401 may be warped in a different direction, for example, an opposite direction to the direction in which the warping and movement are made in order to be out of danger.

According to this embodiment, control is performed in such a manner that the rotation speed of the motor is made constant. Therefore, the warp-enabled portion can be warped at a predetermined velocity and the warping velocity can be variably changed. According to this embodiment, if the pressure sensor 403 comes in contact with the body wall or the like of the subject to be inspected, the fact that the leading portion of the insertion portion has come in contact with the subject to be inspected can be detected and the warp-enabled portion is stopped (or the warping velocity is made lower than a predetermined velocity). As a result, a dangerous state can be avoided and the operability and the safety in the warping operation can be improved. Furthermore, the safety of the human body or the subject to be inspected can be attained.

Figure 15:
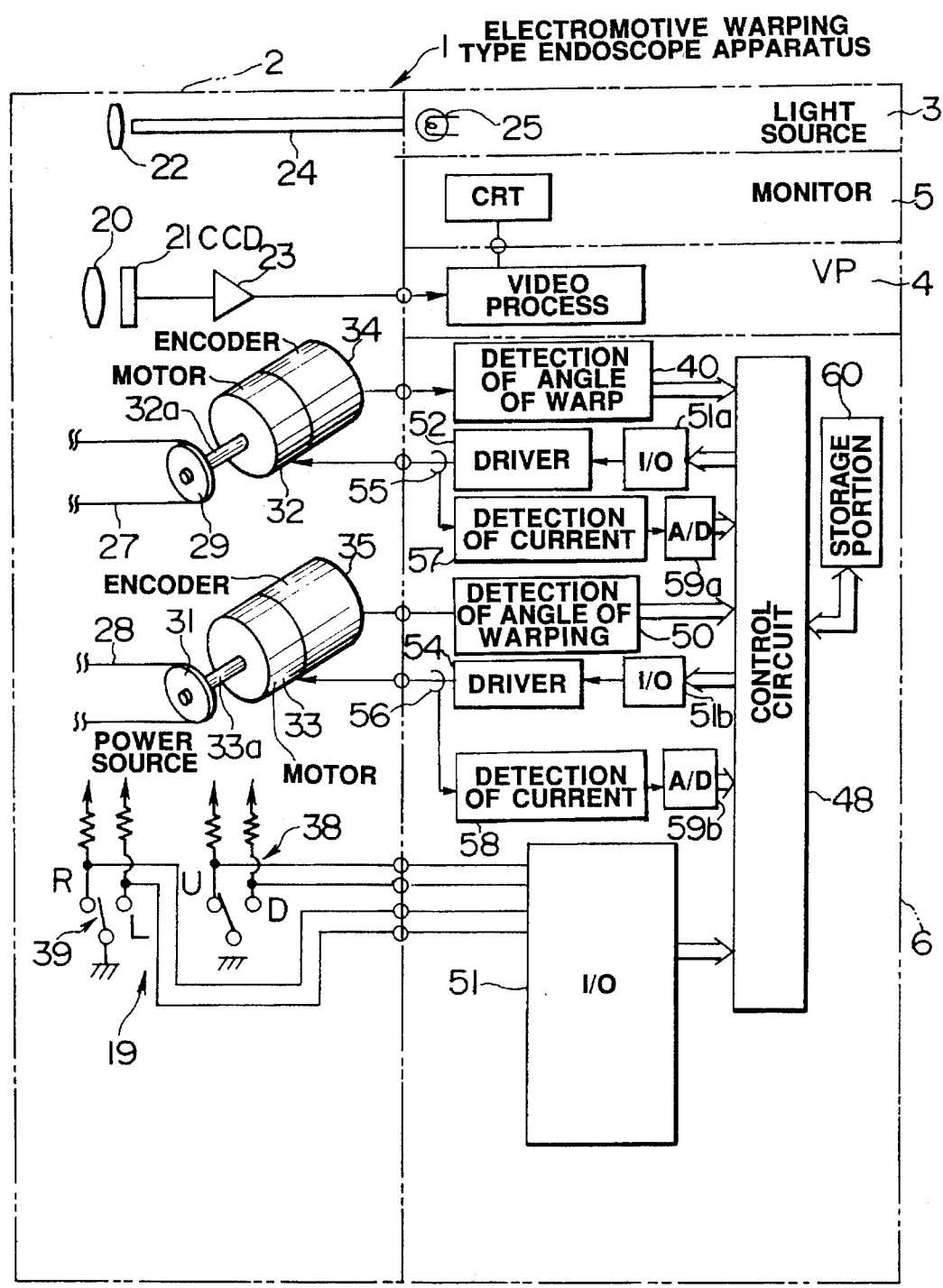
Figure 16:
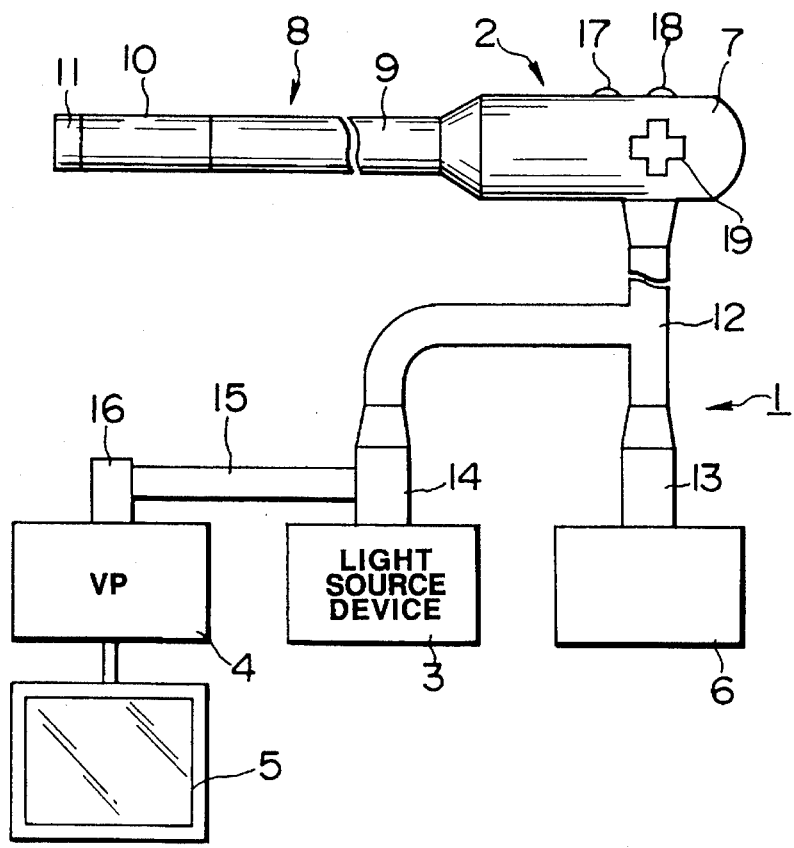
Figure 17:
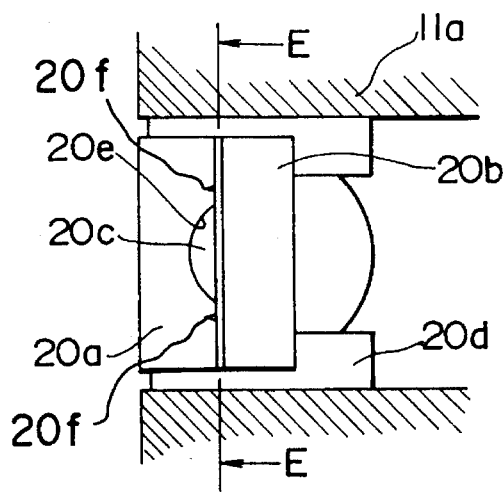
Figure 17:
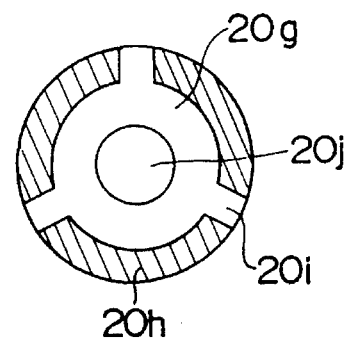

FIGS. 15 to 17(b) illustrate a third embodiment of the present invention. FIG. 15 is a block diagram which illustrates an essential portion of the electromotive warping type endoscope apparatus. FIG. 16 is an overall structural view which illustrates the electromotive warping type endoscope apparatus. FIGS. 17(a) and 17(b) show a cross-sectional view which illustrates an optical system of a leading portion of the endoscope.

An electromotive warping type endoscope apparatus 1 shown in FIG. 16 comprises an electronic type electromotive warping type endoscope 2 including a solid-state image sensing device such as a CCD, a light source device 3 for supplying illuminating light to the electronic type electromotive warping type endoscope 2, a video processor (hereinafter abbreviated to "VP") 4 for converting a video signal supplied from the solid-state image sensing device into a video signal, a monitor 5 for displaying the video signal supplied from the VP 4 and a warping motor control device 6 for controlling the warp of a warp-enabled portion 10 of the electronic type electromotive warping type endoscope 2, the warp-enabled portion 10 to be described later.

The electronic type electromotive warping type endoscope 2 has a large-diameter operation portion 7 and an insertion portion 8 connected to the operation portion 7 and formed into an elongated shape so as to be inserted into the subject to be inspected. A soft portion 9, the warp-enabled portion 10 and a leading unit 11 are connected to the insertion portion 8 in the aforesaid sequential order from the operation portion 7. The warp-enabled portion 10 includes a warping tube constituted by connecting a plurality of warp-enabling blocks so as to be warped vertically and horizontally.

A universal cord 12 branched into two portions at an intermediate portion thereof is connected to the side portion of the operation portion 7. A motor controlling device connector 13 detachably connected to a warping motor control device 6 is disposed at an end portion of the universal cord 12. Furthermore, a light guide connector 14 detachably connected to the light source device 3 is disposed at another end portion of the same. A video controlling cord 15 is extended from the side portion of the light guide connector 14. Furthermore, video processor (VP) connector 16 to be detachably connected to the VP 4 is disposed at an end portion of the video controlling cord 15.

The operation portion 7 has an air/water supplying button 17 for cleaning an observing window (omitted from illustration) and a suction button 18 for sucking body fluids or the like. By operating the air/water supplying button 17, water or air is supplied. By operating the suction button 18, a suction operation is performed through a suction channel (a channel through which a treatment tool passes) formed in the electronic type electromotive warping type endoscope 2.

The leading unit 11 has an objective optical system 20 at the rear end portion of the observing window and the solid-state image sensing device 21 shown in FIG. 15. Furthermore, the leading unit 11 has, at the rear end portion of the illuminating window (omitted from illustration), an illuminating optical system 22 or the like shown in FIG. 15. A signal cable is electrically connected to the solid-state image sensing device 20, the signal cable extending to the VP connector 16 through an amplifier 23. Furthermore, a light emission end of a light guide fiber 24 made of a fiber bundle is located at the rear end portion of the illuminating optical system 22. The light guide fiber 24 is extended to the light guide connector 14 so that illuminating light supplied from a light distributing lamp 25 included in the light source device 3 is incident on the incident end of the light guide fiber 24.

A medical endoscope is cleaned and disinfected at each treatment case and therefore a waterproof endoscope sometimes encounters a problem of invasion of moisture into a portion between lenses of the objective optical system 20 if it has been used in a large number of medical treatments. If moisture is invaded into a portion, for example, between a first lens 20a of the objective optical system 20 shown in FIG. 17(a) and a second lens 20b, the endoscope, which enables a clear visibility to be obtained before it is inserted into the colon, is heated by the body heat after it has been into the colon. Therefore, if the lens is cleaned by cleaning liquid sprayed through the cleaning nozzle in order to clean the surface of the lens contaminated by body fluids or the like, the surface of the lens is rapidly cooled down and invaded moisture is dewed on the reverse side of the first lens 20a as cloud deteriorating the visibility. The cloud deteriorating the visibility becomes a critical problem at the time of performing an observation by using the endoscope and the life is endangered in a case where the observation with the endoscope and treatment must be performed urgently because of bleeding or the like.

In order to prevent the cloud deteriorating the visibility, a space 20c between the first lens 20a and the second 20b is reduced as shown in FIG. 17(a) so as to reduce the quantity of moisture which can be invaded.

The two lenses 20a and 20b are held by a lens frame 20d and a securing portion 11a for holding them including the lens frame 20d is disposed outside the lens frame 20d. In order to satisfactorily prevent generation of the cloud deteriorating the visibility, it is preferable to bond the contact surface of the first lens 20a and that of the second lens 20b. However, if the two lenses are bonded to each other with adhesive, overflowed adhesive will undesirably be introduced into a recess 20e of the lens and the optical path is hindered. Accordingly, V-grooves 20f are formed at a position outer and more adjacent to the rear end surface than the position of the recess 20e of the lens and the adhesive is applied to the portion outer than the V-grooves 20f. As a result, the excessive adhesive can be collected by the V-groove 20f and therefore it does not reach the recess 20e. Thus, a satisfactory effect can be obtained from the adhesion.

A diaphragm 20g is sometimes inserted into a portion between the first lens 20a and the second lens 20b as shown in FIG. 17(b) which is a cross-sectional view taken along line E—E of FIG. 17(a). In this case, it has been said that sufficient adhesive property cannot be obtained in the two sides of the diaphragm 20g while preventing the overflow of the adhesive.

However, according to this embodiment, as shown in FIG. 17(b), a diaphragm formed by cutting the sector-shaped outer portions (the diagonal line portions) of an annular diaphragm 20g is used and the adhesive is introduced from the outer portion of the joined lenses. As a result, in a cut portion 20h of the diaphragm, the first lens 20a and the second lens 20b are directly bonded and the area of contact can be increased, causing the adhesive property to be improved. The diaphragm 20g is supported by the lens frame 20d by the periphery portions 20i thereof, so that the coaxial characteristic between a light transmissible portion 20j and the lens is secured.

The warp-enabled portion 10, which is disposed adjacent to the rear end portion of the leading portion 11 and which can be warped, includes a warping tube formed by a multiplicity of warping blocks (omitted from illustration) longitudinally connected in such a manner that they can be rotated vertically and laterally. A vertical warping operation wire 27 and a lateral warping operation wire 28 shown in FIG. 15 are inserted into a multiplicity of the warping blocks. Furthermore, the front end portion of each wire is connected to the front warping block (omitted from illustration) included by the leading portion 11. The warping operation wires 27 and 28 are inserted into the warp-enabled portion 10 and the flexible tube portion 9, while the rear end portions of them are respectively wound around pulleys 28 and 31 included in the operation portion 7.

The pulleys 29 and 31 are respectively secured to shafts 32a and 33a of, for example, DC motors 32 and 33 serving as electrical warping driving means. The rotations of the DC motors 32 and 33 cause the corresponding pulleys 29 and 31 to be rotated.

In a case where the warp-enabled portion 10 is vertically warped, the DC motor 32 is rotated. When the pulley 29 is rotated, one of the folded back ends of the warping operation wire 27 is pulled and another end is slackened. As a result, the warp-enabled portion 10 is warped in the pulled direction.

The warping operation driving DC motors 32 and 33 have shafts projecting on the side opposing the side on which the pulleys 29 and 31 are disposed. Rotary encoders 34 and 35 are fastened to the aforesaid shafts, so that the amount of angular movement of the DC motor 32 and that of the DC motor 33 are detected.

The operation portion 7 has warping switch portion 19 serving as warping quantity instruction means as shown in FIGS. 15 and 16. The warping switch portion 19 is composed of a vertical-warping switch 38 and a lateral-warping switch 39.

The warping switch portion 19 rotates the DC motors 32 and 33 in response to a warping operation signal transmitted due to the operation of the warping switch portion 19. At this time, the rotary encoders 34 and 35 detect the amount of angular movement of the DC motor 32 and that of the DC motor 33. The detected amounts of the angular movements of the DC motors 32 and 33 are respectively supplied to warp angle detecting circuits 40 and 50. Since the aforesaid amounts of angular movements correspond to the quantity of the warp of the warp-enabled portion 10, the warp angle detecting circuits 40 and 50 convert the supplied quantities of the rotations into data about the warp angle of the warp-enabled portion 10 so as to supply data about the warp angle to a control circuit 48.

The aforesaid vertical warping switch 38 and the lateral warping switch 39 supply warping-operation signals to the control circuit 48 via an I/O 51 included by the warping-motor control device. Contacts R, L, U and D of the switches 38 and 39 adjacent to the I/O 51 are respectively pulled up to the power source by resistors. When the switches 38 and 39 are switched on, a low level switch-on signal is transmitted.

The control circuit 48 controls the forward/reverse rotation of the motor 32, that is, the vertical warping operation via an I/O 51a and a driver 52. Furthermore, the control circuit 48 controls the forward/reverse rotation of the motor 33, that is, the lateral warping operation via an I/O 51b and a driver 54. Driving electric currents for driving the motor 32 and 33 are respectively detected by current detecting circuits 57 and 58 via corresponding current probes 55 and 56 so as to be supplied to the control circuit 48 via an A/D converter 59.

The control performed by the control circuit 48 causes the driver 52 to supply, for example, positive electric power to the motor 32 in a case where the upward warp is desired and to supply, for example, negative electric power to the same in a case where the downward warp is desired. The supplied electric power is converted into an electric current by a current detecting circuit 57 via the current probe 55 and is A/D converted so as to be supplied to the control circuit 48. The control performed by the control circuit 48 causes the driver 54 to supply, for example, positive electric power to the motor 33 in a case where the left directional warp is desired and to supply, for example, negative electric power to the same in a case where the right directional warp is desired. The supplied electric power is converted into an electric current by a current detecting circuit 58 via the current probe 56 and is A/D converted so as to be supplied to the control circuit 48.

A storage portion 60 stores a predetermined power function as a relationship between data detected by the warp angle detecting circuit 40 (and 50) and the current detecting circuit 57 (and 58). If a deviation exceeding, for example, 50% is present between the power function stored in the storage portion 60 and data detected by the warp angle detecting circuit 40 (and 50) and the current detecting circuit 57 (and 58), the control circuit 48 lowers the increasing velocity at which the electric current is supplied to the driver 52 (or 54) so as to lower the warping velocity of the warp-enabled portion 10.

According to this embodiment, the angle of warp of the warp-enabled portion 10 is detected by the control circuit 48 via the warp angle detecting circuits 40 and 50 and also the state of contact between the warp-enabled portion 10 and the subject to be inspected is detected by the current detecting circuits 57 and 58 as electric power consumption. The electric current consumption (or the electric power consumption) of each of the motors 32 and 33 becomes a predetermined value when the warp-enabled portion 10 is not positioned in contact with the subject to be inspected (when unnecessary load is effected) at a predetermined angle of warp.

If the warp-enabled portion 10 is further warped in a state where it is positioned in contact with, for example, a mucous membrane, the warping is performed against the reaction of the mucous membrane. Therefore, an electric current required to obtain the same warp angle becomes large as compared with a case in which the warp-enabled portion 10 is not positioned in contact with the mucous membrane. A case where the rate, at which the electric current is enlarged, is larger than a current value at a certain angle of the warp in a case of no contact by a predetermined degree means a fact that the reaction of the mucous membrane is considerably large. Therefore, it is dangerous to further carelessly warp the warp-enabled portion. According to this embodiment, a predetermined value, which is a ratio of an electric current value in a case of no contact at a certain angle of warp and an electric current value in a case of contact at the same angle of warp, is made to be, for example, 150% and data about it is stored in the storage portion 60. A level higher than the aforesaid predetermined value is considered to be a dangerous level.

According to this embodiment, if a state where the detected ratio is at least 150% higher than the predetermined ratio, control is performed in such a manner that the acceleration of supplying the electric current to each of the motors 32 and 33 is lowered. As a result, the movement of the warp-enabled portion 10 can be slowed down and the warping operability can be improved and the safety of the patient can be secured.

As an alternative to slowing the acceleration of increasing the quantity of supply of the electric current, control may be performed in such a manner that a further supply of the electric current is inhibited and warping is stopped. As a result, further warping operation is not performed. As an alterative to this, the warping operation is controlled in such a manner that the warp-enabled portion is returned in a direction which opposes the direction in which the warp-enabled portion is moved in order to secure safety. In either case, the aforesaid control of the warping velocity is given priority to the instruction made with the warping switch portion 19.

It is preferable that data regarding the predetermined dangerous level and data regarding the levels which can be set can be altered by using a control panel (omitted from illustration). In this case, the structure may be constituted in such a manner that a plurality of data are stored in the storage portion 60 and data is selected as needed.

In a clinical case where the endoscope is inserted by a method such as "Fooking the Fold Method" in which the insertion section is folded in a loop shape, the resistance to be generated at the time of the warping operation is necessarily enlarged, and the predetermined dangerous level is set to a higher-than-normal level. In another case in which there is a desire of passing the endoscope through a narrow tract or internal organ, the predetermined dangerous level is set to a lower-than-normal level. As a result, the safety and the reliability can be improved.

Figure 18:
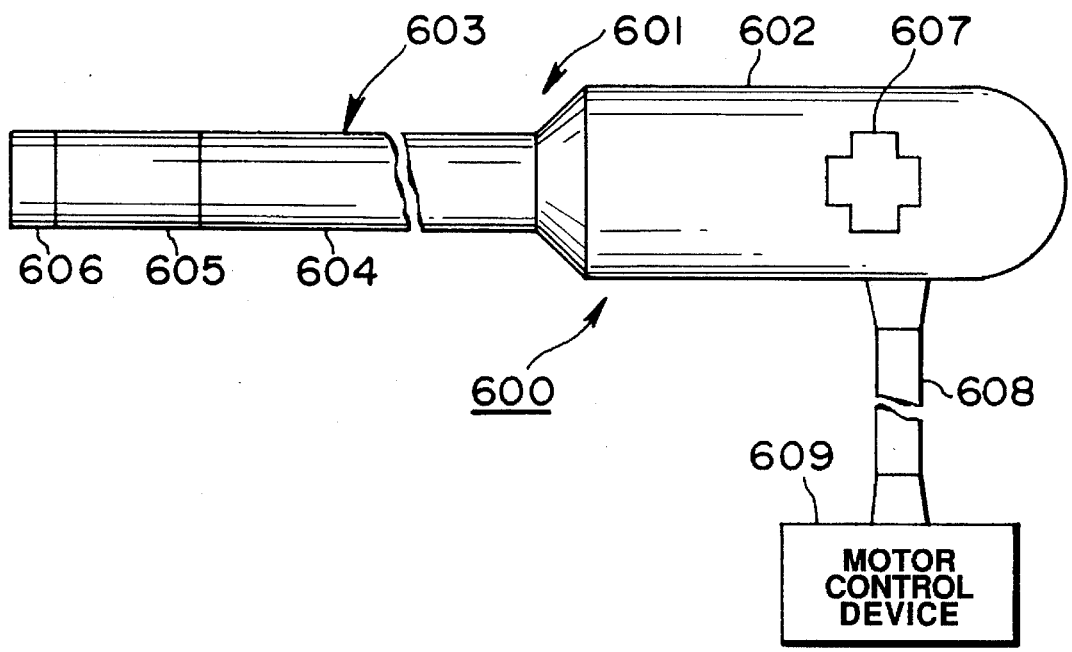
FIGS. 18 to 20 illustrate a fourth embodiment of the present invention, where
Figure 19:
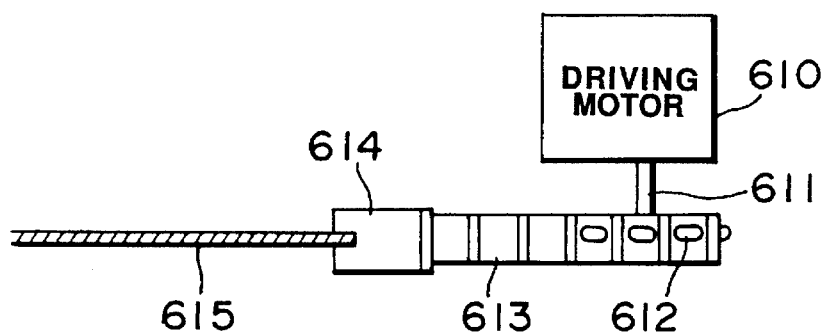
Figure 20:
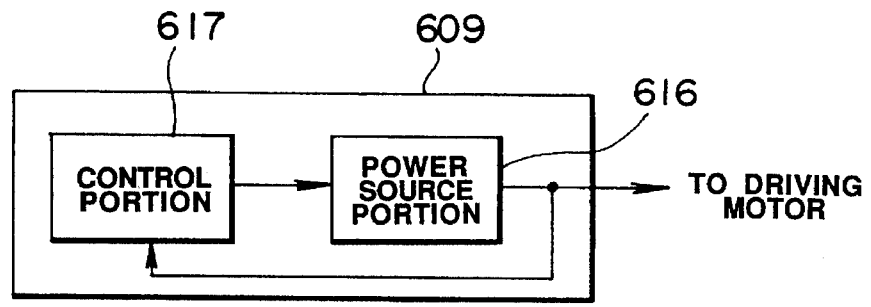

FIGS. 18 to 20 illustrate a fourth embodiment of the present invention. FIG. 18 is a schematic overall structural view which illustrates an electromotive warping type endoscope apparatus, FIG. 19 is a structural view which illustrates a portion of a warping mechanism and FIG. 20 is an electrical block diagram which illustrates a motor control device.

Although the third embodiment is arranged in such a manner that the magnification (the ratio) of the power consumption at a certain angle of the warp with respect to a predetermined value is detected, this embodiment is arranged in such a manner that whether or not the quantity of electric power consumption of the driving motor is a predetermined value is detected so as to detect a state of contact with the subject to be inspected is detected.

An electromotive warping type endoscope apparatus 600 shown in FIG. 18 has an electronic endoscope 601, a motor control device 609 and a light source device (omitted from illustration).

The electronic endoscope 601 has an operation portion 602 and an insertion portion 603 connected to the operation portion 602 and formed into an elongated shape so as to be inserted into a subject to be inspected. The insertion portion 603 has, when viewed from the operation portion 602, a soft portion 604, a warp-enabled portion 605 structured in such a manner that it can be warped and a leading unit 606 connected sequentially.

The warp-enabled portion 605 is constituted by connecting a plurality of warping blocks (omitted from illustration) so as to be warped when a pad-type warping operation switch 607 disposed in the operation portion 602 is operated. The pad-type warping operation switch 607 is a switch for performing the warping operation when it is depressed and stopping the operation when the depression is cancelled.

A universal cord 608 is connected to the side portion of the operation portion 602 and the motor control device 609 is connected to the universal cord 608.

The operation portion 602 includes a DC driving motor for vertically warping the warp-enabled portion 605, a sprocket 612 secured to a drive shaft 611 of the driving motor 610 and a chain 613 engaged with the sprocket 612. Wires 615 are connected to the two end portions of the chain 613 via connection members 614. The wires 615 are inserted into the soft portion 604 and the warp-enabled portion 605 and are connected to the front warping block (omitted from illustration) of the warp-enabled portion 605. FIG. 19 illustrates one of the connection members 614 and the wires 615.

As schematically shown in FIG. 20, the motor control device 609 includes a power source portion 616 for supplying electric power to the driving motor 610 and a control portion 617 for controlling the electric power to be supplied from the power source portion 616 by detecting the power supplied from the power source portion 616.

Although the warping operation device for vertically warping the warping portion 605 is illustrated, the warping mechanism and the control device for laterally warping it are constituted similarly.

When the pad-type warping operation switch 607 disposed on the operation portion 602 is depressed, a drive shaft 611 of the driving motor 610 is rotated. As a result, the wires 615 are pulled/slackened, so that the warp-enabled portion 650 is warped. If the warp-enabled portion 605 comes in contact with the body wall or the like at this time and therefore the resistance of the warp-enabled portion 605 is enlarged, the tension of one of the wires 615 is raised and the electric power consumption of the driving motor 610 is enlarged accordingly. The control portion 617 in the motor control device 609 performs control in such a manner that it detects the electric power consumption of the driving motor 610 and the power source from the power source portion 616 is reduced if the electric power consumption is larger than a predetermined electric power quantity. As a result, the rotation speed of the driving motor 610 is reduced and the warping velocity of the warp-enabled portion 605 is lowered. The aforesaid velocity control is given priority to the instruction made with the warping operation switch 607.

The control portion 617 may stop the power supply from the power source portion 616 to stop warping of the warp-enabled portion 605. As an alternative to this, control may be arranged in such a manner that warping is made in a direction different from the moving direction of the warp-enabled portion, for example, in the opposite direction.

According to this embodiment, the pressure sensor according to the second embodiment and disposed on the outer surface of the insertion portion of the endoscope is omitted from the structure. Therefore, the diameter of the insertion portion of the endoscope can be narrowed. Furthermore, since the warping velocity of the warp-enabled portion 605 can be controlled, for example, it can be lowered by the control portion 617 by detecting the contact of the warp-enabled portion with the tract wall or the like of a subject to be inspected according to a result of a discrimination made whether or not the electric power consumption is larger than a predetermined value. Therefore, the operability and the safety of the warping operation can be improved.

Figure 21:
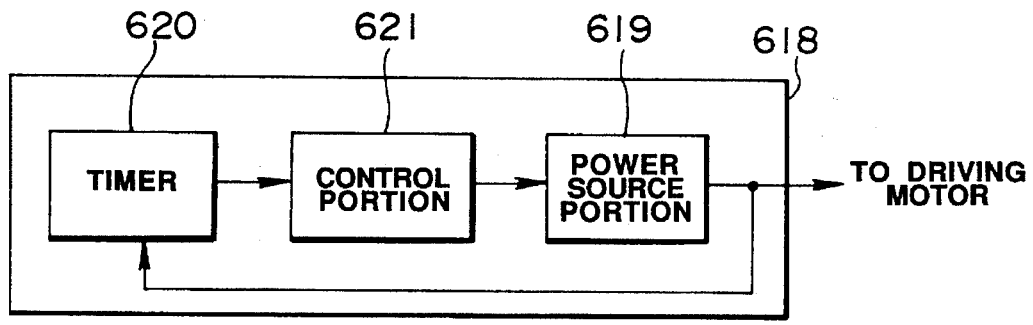
FIG. 21 is an electrical block diagram which illustrates a motor control device according to a first modification to the fourth embodiment of the present invention.

The method of controlling the warping velocity according to the fourth embodiment is not limited to the description made above. Therefore, a modification of the control method will now be described. FIG. 21 is an electrical block diagram which illustrates a motor control device according to a first modification to the fourth embodiment.

The first modification has a timer additionally provided in the motor control device according to the fourth embodiment. Since the structure and the operation are the same as those according to the fourth embodiment, their drawings and the descriptions are omitted here. Therefore, the different portions will now be described with reference to FIG. 21.

A motor control device 618 shown in FIG. 21 includes a power source portion 619 for supplying electric power to the driving motor 610, a timer 620 for detecting the electric power supplied from the power source portion 619 and acting in such a manner that its time counting operation is operated if the supplied electric power is larger than a predetermined value and the time counting operation is stopped if the same is smaller than the predetermined value and a control portion 621 for detecting the time in which the timer 620 is operated so as to perform control in such a manner that the electric power to be supplied from the power source portion 619 is reduced if the detected time is longer than a predetermined time.

In the aforesaid structure, if the electric power consumption of the driving motor 610 has been enlarged due to the enlargement of the resistance of the warp-enabled portion, the electric power supply from the power source portion 619 to the driving motor 610 is enlarged. If the supplied electric power is larger than a predetermined value at this time, the timer 620 is operated and data about the counted time is transmitted to the control portion 621.

If the enlargement of the supplied electric power has taken place instantaneously and the supplied electric power is smaller than a predetermined value, the timer 620 is stopped and the time counting is also stopped. On the contrary, if the supplied electric power is continuously larger than the predetermined value, the time counting operation is continued. The control portion 621 performs control in such a manner that the electric power supply from the power source portion 619 is reduced if the counted time data is longer than a predetermined time. This is a case in which the time where the supplied power is larger than a predetermined value is longer than a predetermined time. That is, in a case where the time in which the warp-enabled portion 650 is in contact with the wall of the tract or the like of a subject to be inspected is longer than a predetermined time, the electric power to be supplied is reduced. As a result, the rotation speed of the driving motor 610 is lowered and the warping velocity of the warp-enabled portion 605 is also lowered.

According to the first modification, the following effect can be obtained in addition to the effect obtainable from the fourth embodiment: Since the time is not lengthened to the aforesaid predetermined time in a case where the driving electricity supplied by the power source portion 619 is instantaneously enlarged and immediately returned to a level below the predetermined value by, for example, a quick operation of the warping operation switch 607, the warping operation is not affected. Therefore, according to the first modification, a further accurate and reliable warping operation control can be performed and the safety of the warping operation can be secured further satisfactorily. Since the other structures, operations and effects are the same as those according to the fourth embodiment, their descriptions are omitted here.

Although a pad-type (the warping operation is enabled during depression of the switch and the operation is stopped when the switch depression is cancelled) warping switch is used as the warping quantity instruction means according to the fourth embodiment and the first modification, a joy-stick type (the warping operation is enabled according to the angle of the tilt of a lever) warping switch may be employed to perform the similar control. Then, a second modification will now be described.

Figure 22:
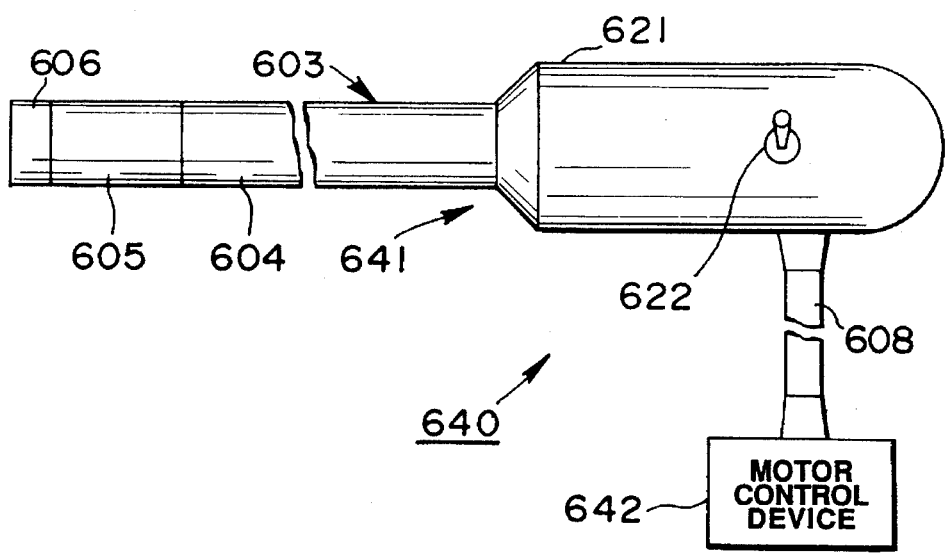
FIGS. 22 to 32 illustrates a second modification to the fourth embodiment, where
Figure 23:
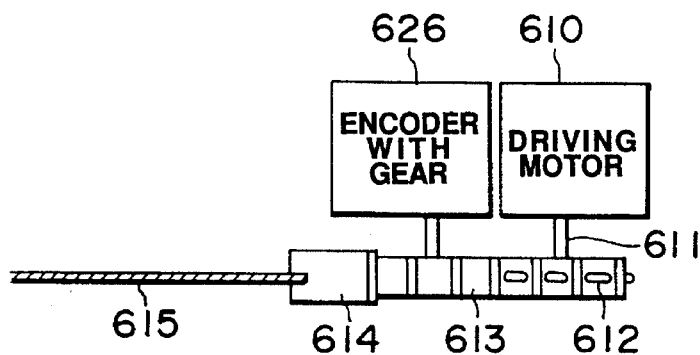
Figure 24:
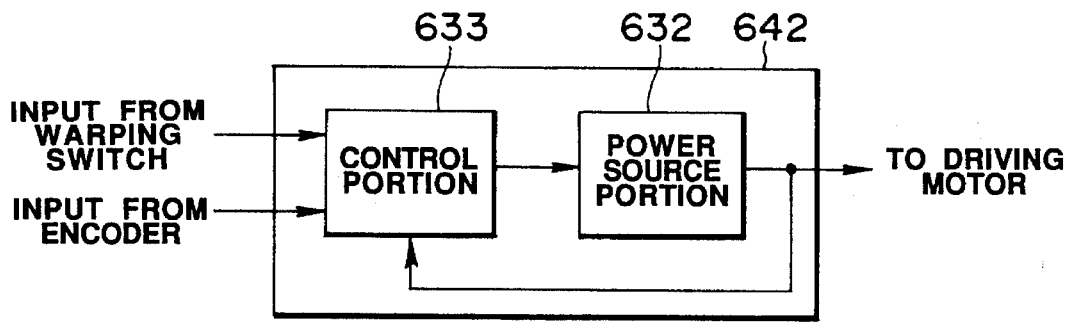

FIGS. 22 to 32 illustrate the second modification of the fourth embodiment. FIG. 22 is a schematic overall structural view which illustrates an electromotive warping type endoscope apparatus, FIG. 23 is a structural view which illustrates a portion of a warping mechanism and FIG. 24 is an electrical block diagram which illustrates a motor control device.

The endoscope according to the second modification is arranged in such a manner the warping operation switch 607 according to the fourth embodiment is changed from a pad-type switch to a joy-stick type switch and an encoder is additionally provided adjacent to the driving motor 610. The same structures and operations as those according to the fourth embodiment are given the same reference numerals and their descriptions are omitted here.

An electromotive endoscope apparatus 640 shown in FIG. 22 comprises an electronic endoscope 641, a motor control device 642 and a light source device (omitted from illustration).

The control portion 621 for the electronic endoscope 640 has a joy-stick-type warping operation switch 622.

The operation portion 621 includes the DC driving motor 610 for warping the warp-enabled portion 605, the sprocket 612 secured to the drive shaft 611 of the driving motor 610, an encoder 626 having a gear to be engaged with the sprocket 612 and the chain 613 to be engaged with the sprocket 612. The warping operation wires 615 are connected to the end portions of the chain 613 via the connection members 614. The warping operation wires 615 are connected to the front warping block of the warp-enabled portion 605.

The warping operation switch 622, the driving motor 610 and the encoder 626 having the gear are electrically connected to the motor control device 642 via signal lines (omitted from illustration) which pass through the aforesaid universal cord 608.

As shown in FIG. 24, the motor control device 642 includes a power source portion 632 for supplying electric power to the driving motor 610 and a control portion 633 for detecting the electric power supplied to the driving motor 610 and controlling the electric power to be supplied from the power source portion 632.

The control portion 633 calculates the difference between the angle of tilt of the warping operation switch 622 and the angle of rotation of the encoder 626 so as to detect the warping direction and the quantity of warp of the warp-enabled portion 605. The control portion 633 controls the power source portion 632 in such a manner that the power source portion 632 supplies electric power by a quantity which corresponds to the warp of the warp-enabled portion 605. Furthermore, the control portion 633 detects the electric power to be supplied to the driving motor 610 and performs control in such a manner that the electric power to be supplied is reduced if the supplied electric power is smaller than a predetermined value.

In the thus arranged structure, when the joy-stick-type warping operation switch 622 is operated, the warp-enabled portion 650 is warped in a predetermined direction and by a predetermined angle. If the warp-enabled portion 605 comes in contact with the body wall or the like and therefore the resistance of the warp-enabled portion is enlarged, the electric power consumption of the driving motor 610 is enlarged. The control portion 633 included by the motor control device 642 and detecting the electric power consumption of the driving motor 610 performs the control in such a manner that the electric power supply from the power source portion 632 is reduced if the aforesaid electric power consumption is larger than the predetermined value. As a result, the rotation speed of the motor is lowered and the warping velocity of the warp-enabled portion 605 is lowered.

The other structures, operations and effects are the same as those according to the fourth embodiment and therefore their descriptions are omitted here.

Figure 25:
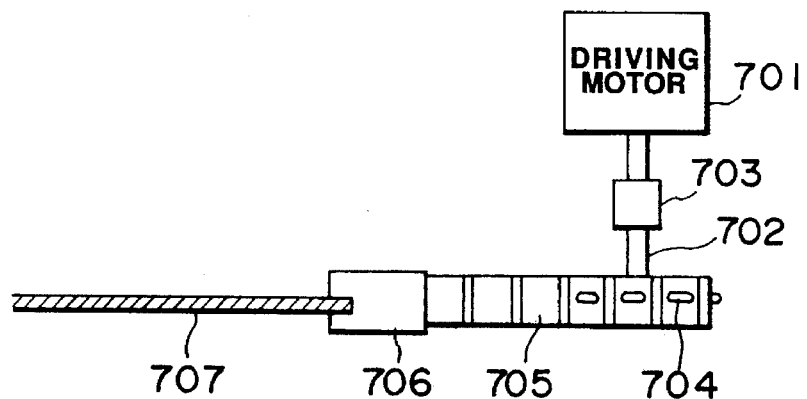
Figure 26:
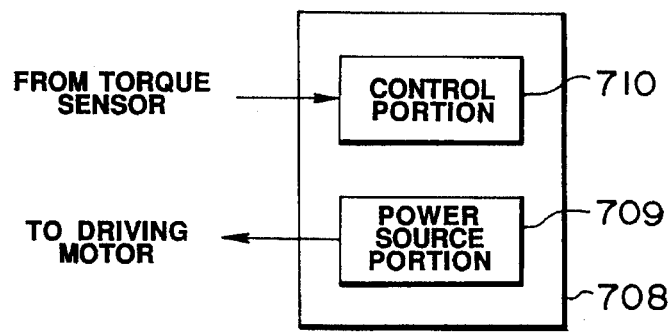

FIGS. 25 and 26 illustrate a fifth embodiment of the present invention. FIG. 25 is a structural view which illustrates a portion of a warping mechanism and FIG. 26 is an electrical block diagram which illustrates a motor control device.

This embodiment is arranged in such a manner that a torque sensor is provided for the drive shaft of the driving motor in addition to the structure according to the fourth embodiment. The overall structure of the electromotive warping type endoscope apparatus is the same as that of the apparatus according to the fourth embodiment shown in FIG. 18 and therefore its description is omitted here.

The operation portion 602 shown in FIG. 25 has a DC driving motor 701 for warping the warp-enabled portion 605 and a sprocket 704 secured to an end portion of a drive shaft 702 of the driving motor 701. Furthermore, a torque sensor 703 for measuring the torsion of the drive shaft 702 is disposed adjacent to the central portion of the drive shaft 702 of the driving motor 701. In addition, a chain 705 is engaged with the sprocket 704 and warping operation wires 707 (only one of them is illustrated) are secured to the end portions of the chain 705 via connection members 706 (only one of them is illustrated).

The warping operations wires 707 are connected to the front warping block (omitted from illustration) of the warp-enabled portion 605.

The motor control device 708 shown in FIG. 26 has a power source portion 709 for supplying electric power to the driving motor 701 and a control portion 710 for controlling the output from the power source portion 709 on the basis of the quantity of torsion measured by the torque sensor 703. By means of the universal cord 608 connected to the side portion of the operation portion 602, the torque sensor 703 is electrically connected to the control portion 710 and the driving motor 701 is also electrically connected to the power source portion 709.

In the thus arranged structure, when the warping operation switch 607 is operated and the operation wire 707 is given a tension due to the warping operation of the warp-enabled portion 605, also the sprocket 704 is given torque, causing the motor drive shaft 702 to be twisted. The torque sensor 703 detects the torsion and transmits this to the control portion 710 included by the motor control device 708. If the quantity of torsion is smaller than a predetermined value, the warp-enabled portion 605 is not in contact with the tract or the like. Therefore, the control portion 710 maintains the electric power to be supplied from the power source portion 709. As a result, the rotation speed of the drive shaft 702 of the driving motor 701 is maintained at a predetermined value and also the warp-enabled portion 605 is warped at a predetermined velocity.

If the quantity of torsion of the torque sensor 703 is larger than the predetermined value, the control portion 710 discriminates a fact that the warp-enabled portion 605 is in contact with the wall of the tract or the like and reduces the electric power supplied from the power source portion 709. As a result, the rotation speed of the drive shaft 702 of the driving motor 701 is lowered and also the warping velocity of the warp-enabled portion 605 is lowered. The aforesaid velocity control is given priority to the instruction made with the warping operation switch 607.

The control may be performed in such a manner that the warp-enabled portion is stopped or it is returned in a direction, for example, an opposite direction which is different from the direction in which the warp-enabled portion is moved as well as lowering the warping velocity.

According to this embodiment, since the insertion portion 603 has no pressure sensor, the diameter of the insertion portion can be narrowed as compared with the second embodiment. Furthermore, since no pressure sensor is provided for the insertion portion of the endoscope, the apparatus can be easily manufactured and the diameter of the insertion portion of the endoscope can be narrowed. In addition, according to this embodiment, the control portion 710 discriminates whether or not the contact of the warp-enabled portion with the wall of the tract of the subject to be inspected according to a fact whether or not the quantity of torsion is larger than the predetermined value. According to this information, the control portion 710 controls the warping velocity of the warp-enabled portion 605, for example, lowers it. Therefore, the operability of the warping operation can be improved and the safety can be secured more satisfactorily.

Figure 27:
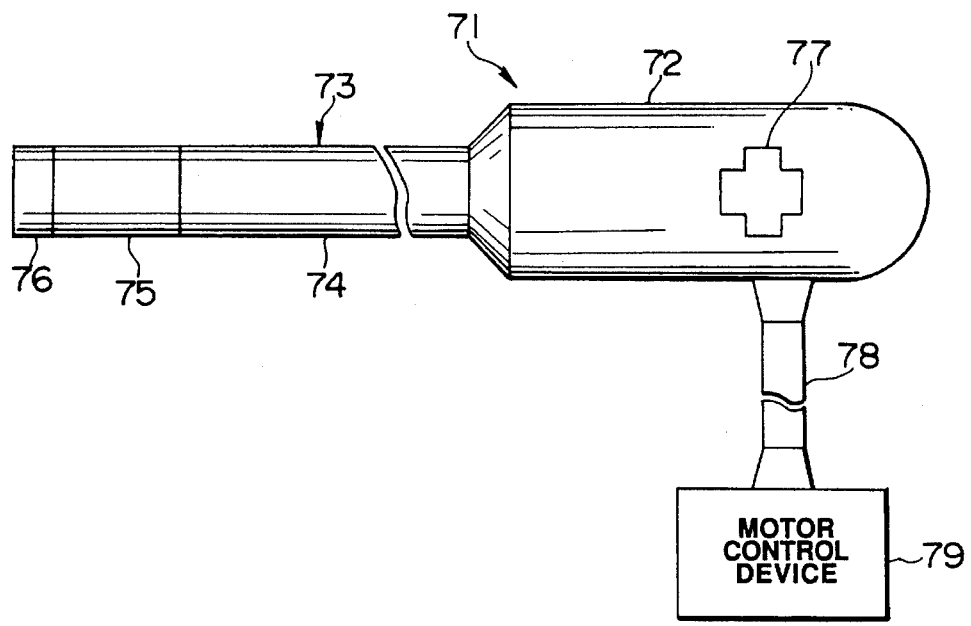
Figure 28:
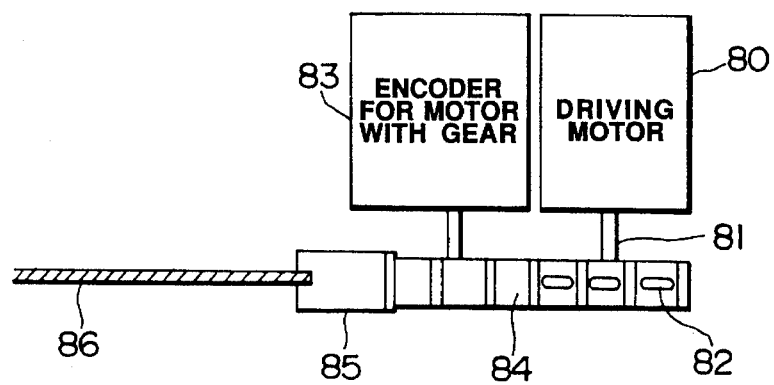
Figure 29:
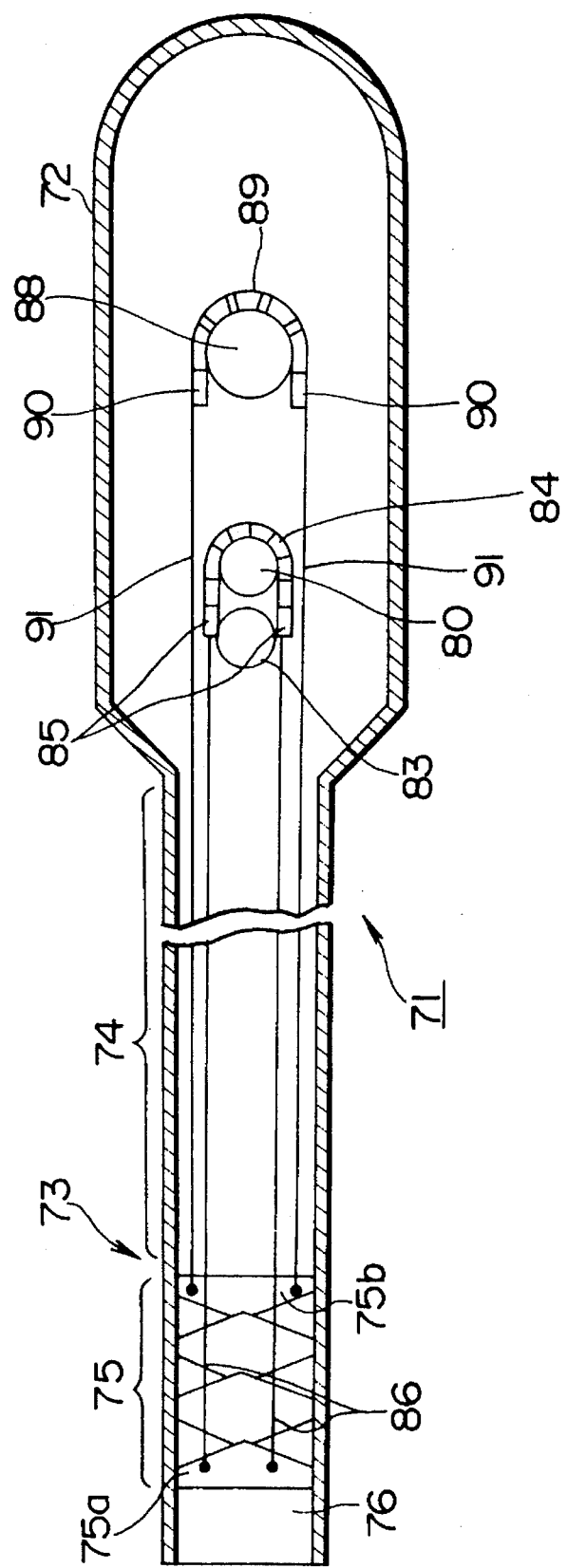
Figure 30:
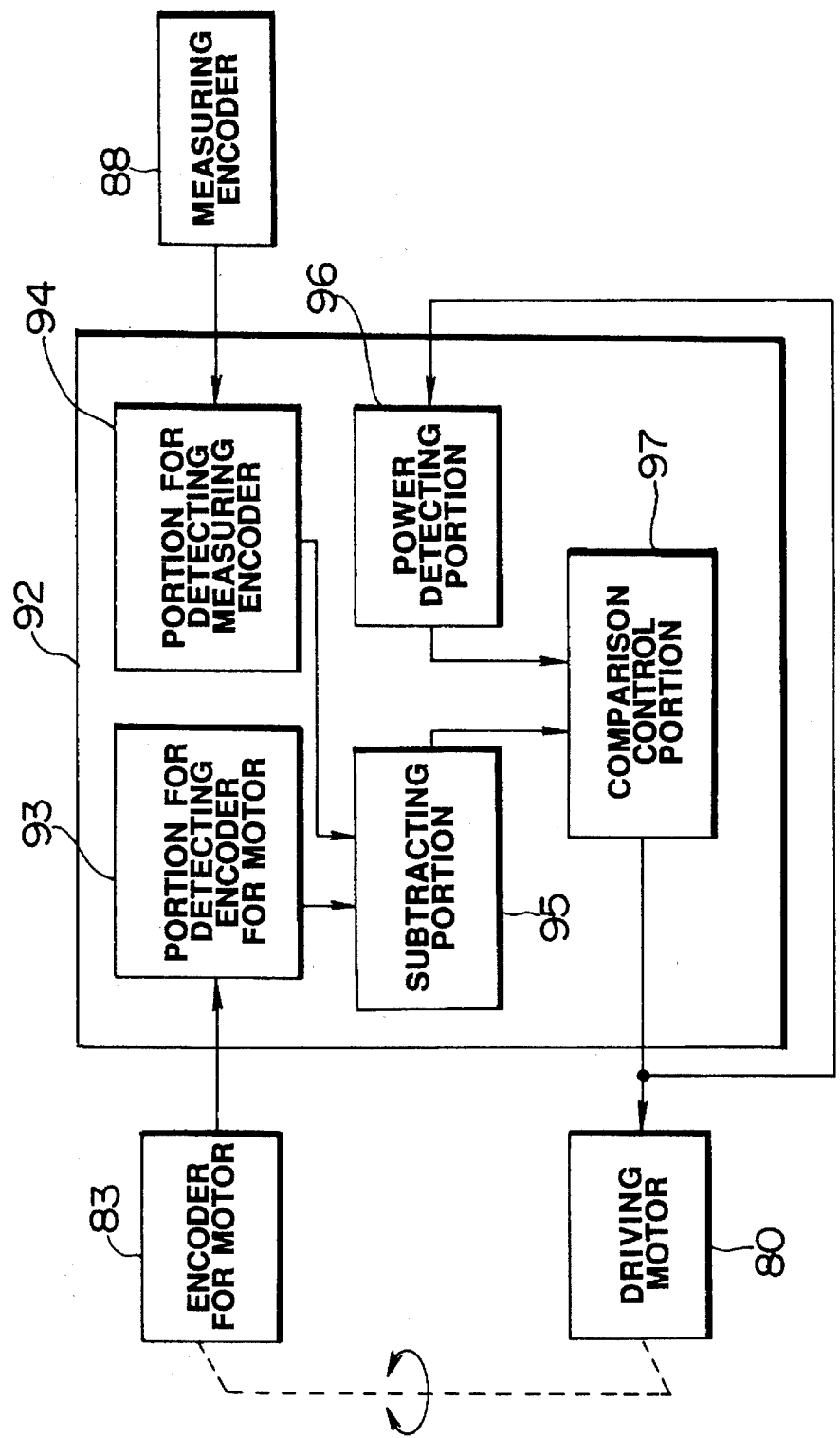

FIGS. 27 to 30 illustrate a sixth embodiment of the present invention. FIG. 27 is an overall structural view which illustrates an electromotive warping type endoscope apparatus, FIG. 28 is a structural view which illustrates a portion of a warping mechanism, FIG. 29 is a cross-sectional view which illustrates the overall structure of the warping mechanism and FIG. 30 is an electrical block diagram which illustrates portions relating to the warping control operation.

The aforesaid third embodiment is arranged in such a manner that the state of the insertion portion is detected from the relationship between the motor rotation angle and the electric current consumption. However, this embodiment is arranged in such a manner that a measuring wire for detecting the state of a soft portion is provided in addition to the warping operation wires and only the state of the warp-enabled portion is detected from the difference in the quantity of movement between the two wires.

The electronic endoscope 71 shown in FIG. 27 has an operation portion 72 and an insertion portion 73 connected to the operation portion 72 and formed into an elongated shape so as to be inserted into a subject to be inspected. The insertion portion 73 has a soft portion 74, a warp-enabled portion 75 which can be warped and a leading unit 76 in this sequential order when viewed from the operation portion 72.

The warp-enabled portion 75 includes a warping tube constituted by connecting a plurality of warping blocks and can be warped vertically and laterally by a warping operation switch 77 disposed on the operation portion 72. Furthermore, a universal cord 78 is connected to the side portion of the operation portion 72, the universal cord 78 establishing the connection between a motor control device 79 to be described later and a light source device or the like (omitted from illustration).

As shown in FIG. 28, the operation portion 72 includes a DC driving motor 80 for vertically warping the warp-enabled portion 75, a sprocket 82 secured to a drive shaft 81 of the driving motor 80, a motor encoder 83 having a gear engaged with the sprocket 82 and a warping chain 84 engaged with the sprocket 82. Warping operation wires 86 are connected to the end portions of the warping chain 84 via the warping connection members 85.

As shown in FIG. 29, which is an axial directional cross-sectional view of the electronic endoscope 71, the warping operation wires 86 are inserted into the soft portion 74 and the warp-enabled portion 75 and are connected to a front warping block 75a.

A measuring chain 89 is engaged with a measuring encoder 88 having a gear and included in the operation portion 72. Measuring wires 91 are connected to the end portion of the measuring chain 89 via measuring connection members 90. The measuring wires 91 are inserted into the soft portion 74 and are connected to the warping block 75b adjacent to the soft portion 74. The measuring encoder 88 having the gear acts to detect the state of the soft portion 74.

The motor encoder 83 having the gear, the measuring encoder 88 having the gear and the driving motor 80 are electrically connected to a motor control device 92 to be described later.

FIG. 30 schematically illustrates the motor control device 92.

The motor control device 92 includes a motor encoder detecting portion 93 for detecting the quantity of movement of the warping operation wires 86 in accordance with a signal transmitted from the motor encoder 83, a measuring encoder detecting portion 94 for detecting the quantity of movement of the measuring wires 91 in accordance with a signal transmitted from the measuring encoder 88, a subtraction portion 95 for calculating the difference between the two quantities of movement, an electric power detecting portion 96 for detecting the electric power consumption of the driving motor 80 and a comparison control portion 97 for making a comparison between the output signal from the subtraction portion 95 and the electric power detecting portion 96 so as to control the electric power supply to the driving motor 80.

Although description is made about the warping operation device for vertically warping the warp-enabled portion 75, the warp operation device for laterally warping the warp-enabled portion 75 is similarly structured and therefore its descriptions and drawings are omitted from illustration.

In the aforesaid structure, when the warping operation switch 77 is depressed, the driving motor 80 is rotated so as to pull/slacken the warping operation wires 86. As a result, the warp-enabled portion 75 is warped. Therefore, the warping operation wires 86 and the measuring wires 91 inserted into the insertion portion 73 are moved. The quantities of the movements of these wires 86 and 91 are detected by the motor encoders 83 and the measuring encoder 88.

The subtraction portion 95 calculates the difference between the values respectively detected by the motor encoder 83 and the measuring encoder 88, so that the affection of the warp of the soft portion 74 is eliminated and the quantity of movement of the wire in only the warp-enabled portion 75 is obtained. That is, the state of the warp of only the warp-enabled portion can be detected.

The electric power detecting portion 96 detects the electric power consumption of the driving motor 80. The comparison control portion 97 makes a comparison between the quantity of the movement of the wire and the electric power consumption. If the relationship between them is deviated from a normal relationship (a state where the warp-enabled portion is not in contact with the subject to be inspected), for example, and if the value of the ratio is large similarly to the third embodiment, a discrimination is made that it is in contact with the subject to be inspected. As a result, the comparison control portion 97 decreases the acceleration of increase in the supply of the electric current to the driving motor 80 so as to lower the warping velocity. The aforesaid velocity control is given priority to the instruction of the warping operation switch 77.

Since the measuring wires 91 are provided according to this embodiment, the quantity of the warp of only the warp-enabled portion 75 can be accurately discriminated. In a case where the insertion portion and the warp-enabled portion are warped to form a wave, or the insertion portion forms a loop-like shape by employing the Fooking the Fold method and thereby the state of the warp-enabled portion cannot be accurately detected by only the wires 85, the state of the warp of only the warp-enabled portion 75 can be accurately detected and the movement of the warp-enabled portion can be lowered. Therefore, the operability can be improved and the safety of a patient can be secured.

As an alternative to lowering the acceleration of increase in the quantity of the supply of the electric current, control may be performed in such a manner that further supply of the electric current is inhibited and the warping operation is stopped. As a result, a further warping operation is not performed. As an alternative to this, the warping velocity control is performed in such a manner that the warp-enabled portion is moved in a direction which is different from the direction in which the warp-enabled portion is moved, for example, the same is returned in the opposite direction, so that the safety is secured.

Figure 31:
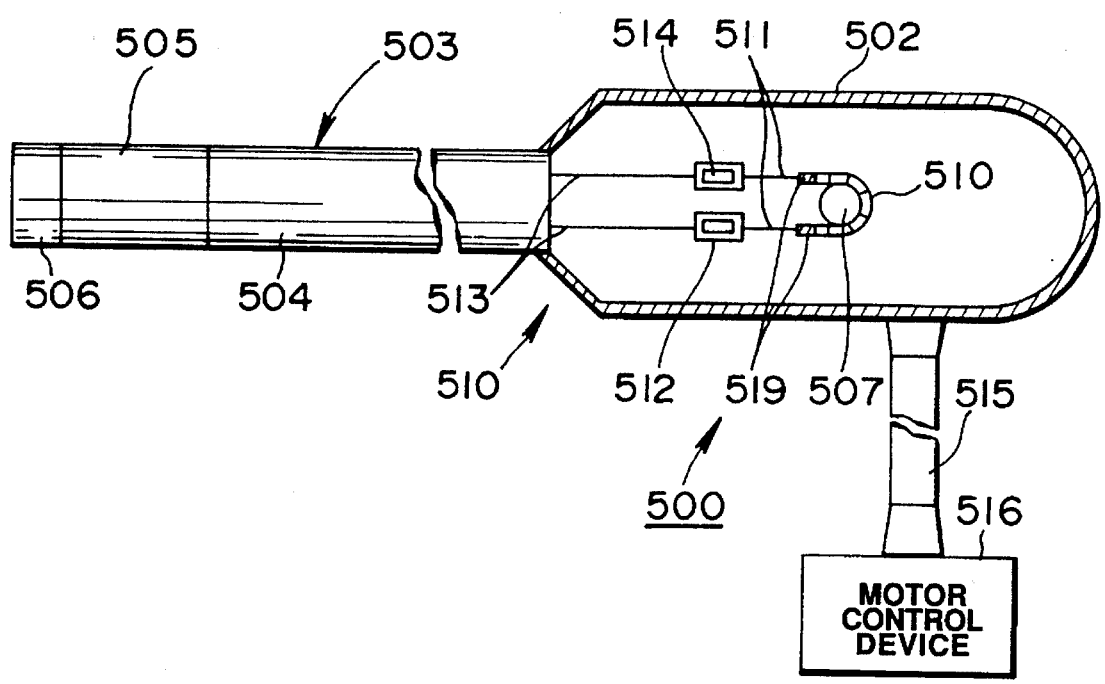
Figure 32:
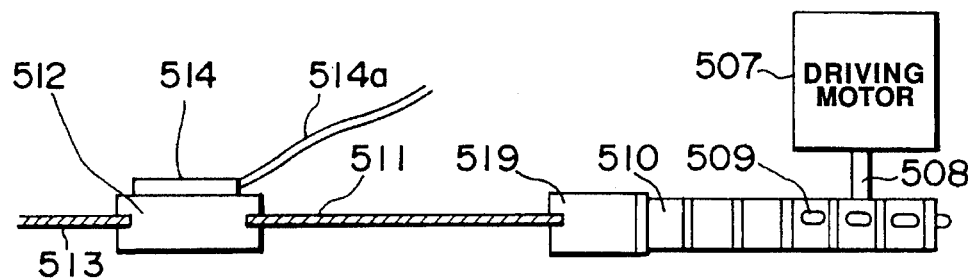
Figure 33:
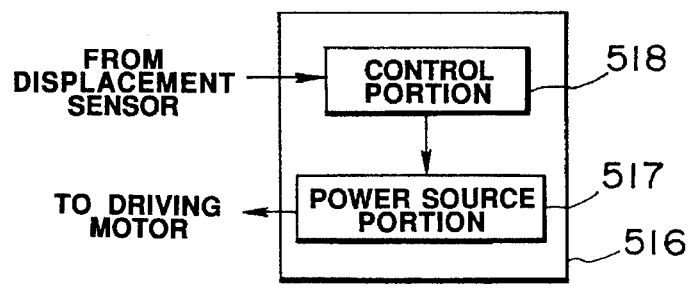

FIGS. 31 to 33 illustrate a seventh embodiment of the present invention. FIG. 31 is an overall structural cross-sectional view which illustrates an electromotive warping type endoscope apparatus. FIG. 32 is a side elevational view which illustrates a portion of a warping mechanism, and FIG. 33 is an electrical block diagram which illustrates a motor control device.

An electromotive warping type endoscope apparatus 500 according to this embodiment has an electromotive warping type endoscope 501, a motor control device 516 and a light source device (omitted from illustration).

The electromotive warping type endoscope 501 has a tension sensor provided for the warping operation wire in place of the pressure sensor according to the second embodiment so as to detect the state of the warp.

FIG. 31 is an axial directional cross-sectional view which illustrates only an operation portion 502 of an electromotive warping type endoscope 501.

An insertion portion 503 is connected to the operation portion 502 of the electromotive warping type endoscope 501. The insertion portion 503 has a soft portion 504 having flexibility, a warp-enabled portion 505 which can be warped and a leading unit 506 disposed sequentially when viewed from the operation portion 502.

As shown in FIG. 31 or 32, the operation portion 502 includes a DC driving motor 507 for vertically warping the warp-enabled portion 505, a sprocket 509 secured to a drive shaft 508 of the driving motor 507 and a chain 510 engaged with the sprocket 509. Wires 511 adjacent to the operation portion are connected to the two end portions of the chain 510 via connection members 519. The other end portions of the wires 511 adjacent to the operation portion are connected to the wires 513 adjacent to the insertion portion via displacement members 512. The wires 513 adjacent to the insertion portion are inserted into the soft portion 504 and the warp-enabled portion 505 and are connected to the front warping block (omitted from illustration) of the warp-enabled portion 505.

Displacement sensors 514 made of, for example, piezoelectric ceramics, are secured on the surfaces of the displacement members 512 by bonding or the like.

The driving motor 507 and the displacement sensor 514 are electrically connected to the motor control device 516 via corresponding signal lines passing through a universal cord 515 connected to the side portion of the operation portion 502.

A motor control device 516 shown in FIG. 33 includes a power source portion 517 for supplying electric power to the driving motor 507 and a control portion 518 for controlling the output from the power source portion 517. The displacement sensor 514 and the control portion 518 are electrically connected to each other by signal lines 514a (only one of them is illustrated) covered with material such as an ETFE resin which is durable against bending. Also, the power source portion 517 and the driving motor 507 are electrically connected to each other by the aforesaid signal line.

Although only the warping mechanism and the control device for vertically warping the warp-enabled portion 505 are described here, the warping mechanism and the control device for laterally warping it are structured similarly.

In the aforesaid structure, when a warping operation switch (omitted from illustration) disposed on the operation portion 502 is depressed, the rotational shaft 508 of the driving motor 507 is rotated. As a result, the wire 513 adjacent to the insertion portion is pulled and the warp-enabled portion 505 is therefore warped. If the resistance force of the warp-enabled portion 505 is enlarged because the warp-enabled portion 505 comes in contact with the body wall or the like, the tension of one of the wires 513 adjacent to the insertion portion is raised and therefore also the tension applied to the displacement member 512 is raised. Also the tension applied to the displacement sensor 514 secured to the displacement member 512 is raised, causing the displacement sensor 514 to be displaced. The displacement sensor 514 converts the quantity of displacement into an electric signal so as to transmit it to the control portion 518. The control portion 518 receives the electric signal. If the level (the quantity of displacement) of the electric signal is higher than a predetermined level, the control portion 518 reduces the electric power to be supplied from the power source portion 517 to the motor 507. As a result, the rotation speed of the driving motor 507 is lowered and the warping velocity of the warp-enabled portion 505 is lowered. The warping velocity control to be performed in a case where the quantity of displacement exceeds a predetermined value is given priority to the instruction made with the warping operation switch.

The control may be performed in such a manner that the warp-enabled portion 505 may be stopped, or the warping is performed in a direction which is different from the direction in which the warp-enabled portion is moved; for example, it is returned in the opposite direction.

If the displacement sensor 514 is moved, the flexible signal line 514a is then employed as the signal line, and the breakage of the signal line can be prevented.

Since the displacement sensor is disposed in the operation portion according to the present invention, the diameter of the insertion portion can be narrowed as compared with the second embodiment in which the pressure sensor is provided on the outer surface of the insertion portion. Furthermore, according to this embodiment, the contact of the warp-enabled portion with the tract of a subject to be inspected is detected depending upon the change in the quantity of displacement of the displacement sensors 514 and the warping velocity of the warp-enabled portion can be controlled; for example, the warping velocity can be lowered. Therefore, the operability and the safety of the warping operation can be improved.

Figure 34:
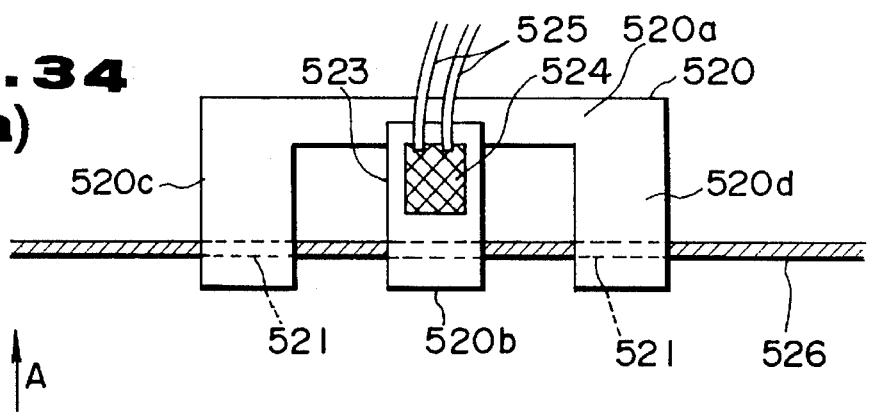
FIGS. 34(a) and 34(b) show structural views illustrating a first modification of the seventh embodiment.
Figure 34:
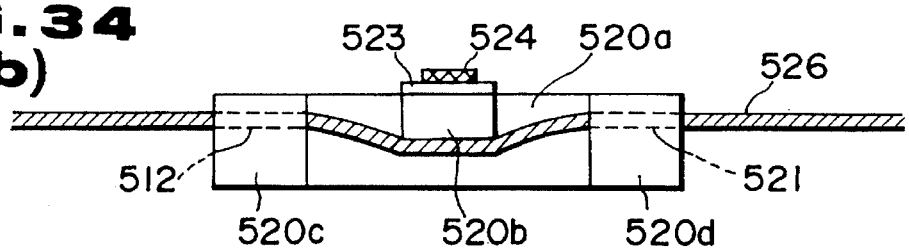

FIGS. 34(a) and 34(b) show a structural view which illustrates a first modification to the seventh embodiment featuring an essential portion.

The first modification is arranged in such a manner that the wires 511 and 513 connected to the displacement member 512 according to the seventh embodiment are replaced by one wire and the shape of the displacement member is changed. Since the other factors such as the positions and the number of the displacement members are the same, descriptions of the other portions are omitted here.

FIG. 34(a) illustrates a displacement member 520 and a warping operation wire 526. FIG. 34(b) is a cross-sectional view taken along line A of FIG. 34(a). FIGS. 34(a) and 34(b) illustrate one side of the displacement member 520 and the warping operation wire 526 and the like. The other side of them are the same and therefore their illustrations are omitted.

The E-shaped displacement member 520 is formed basing upon a body portion 520a and having a projecting thin portion 520b at the central portion thereof and thick projecting portions 520c and 520d formed on the two sides of the thin portion 520b. The projecting portions 520c and 520d have holes 521 through which the warping operation wire 526 passes and which run parallel to the body portion 520a.

Displacement sensors 524 made of high molecular piezoelectric sensors or the like are secured to the two sides of the thin portion 522b with an adhesive or the like via insulating members 523 made of rubber or the like. Signal lines 525 capable of satisfactorily withstanding bending as described in the seventh embodiment are electrically and mechanically connected to the displacement sensors 524 by soldering or the like. These signal lines 525 are connected to the control portion 518 included in the motor control device 516.

The warping operation wire 526 is inserted into the holes 521 while pressing the thin portion 520b.

In the aforesaid structure, when the warping operation wire 526 is applied with tension, it presses the thin portion 520b of the displacement member 520. As a result, the displacement sensor 524 secured to the thin portion 520b is deformed and it transmits an electric signal corresponding to the quantity of deformation to the control portion 518. The control portion 518 reduces electric power supplied from the power source portion 517, causing the rotation speed of the motor to be lowered. As a result, the warping velocity is lowered.

According to the first modification, the number of the warp operation wires can be decreased to one and the quantity of displacement can be enlarged as compared with the seventh embodiment. Therefore, accurate detection can be performed. Since the other structures, operations and effects are the same as those according to the seventh embodiment, their descriptions are omitted here.

Figure 35:
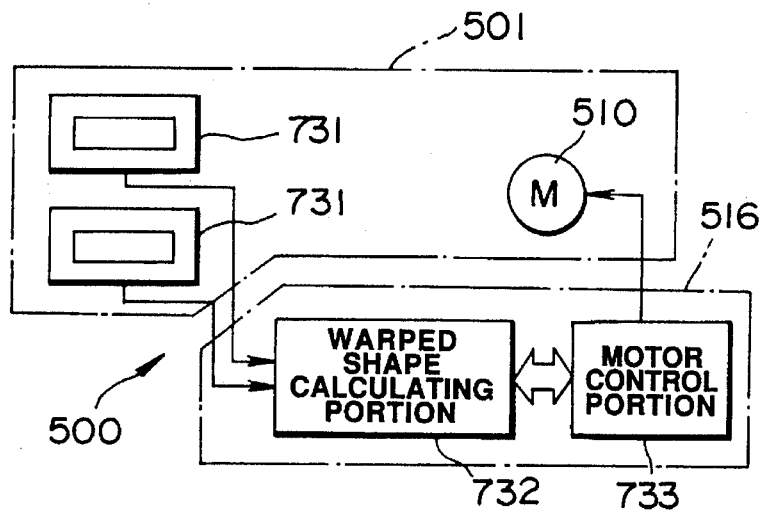
FIGS. 35 and 36 illustrate a second modification to the seventh embodiment of the present invention, where
Figure 36:
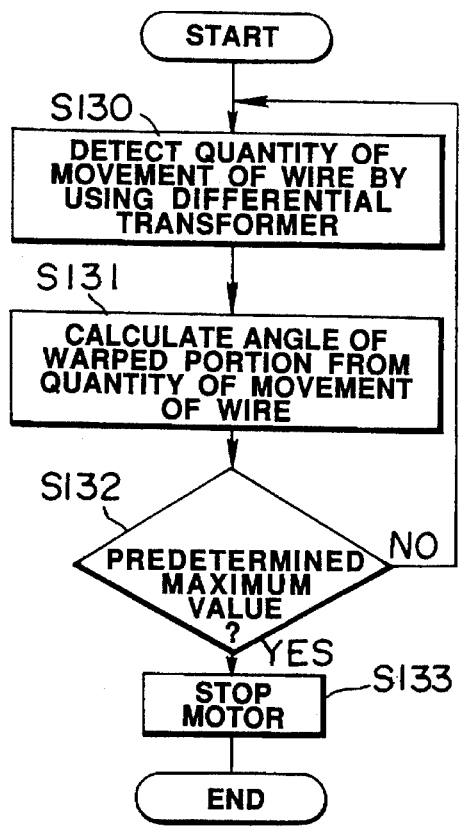

FIGS. 35 and 36 illustrate a second modification of the seventh embodiment. FIG. 35 is an electrical block diagram which illustrates the warping operation section of an electromotive warping type endoscope apparatus and FIG. 36 is a flow chart which illustrates the warp control operation.

The electromotive warping type endoscope apparatus according to this embodiment has a differential transformer in place of the displacement sensor according to this embodiment. Furthermore, according to this modification, a warped shape calculating portion for calculating the angle of warp from the quantity of movement of the wire detected by the differential transformer and a motor control portion for controlling a warping motor are provided. The structures and operations similar to those according to the seventh embodiment are given the same reference numerals, and their descriptions are omitted here.

As shown in FIG. 35, the electromotive warping type endoscope 501 comprises differential transformers 731 for detecting the quantity of movement of each of the wires 513.

On the other hand, a motor control device 516 comprises a warped shape calculating portion 732 for calculating the quantity of movement of each of the wires 513 from signals detected by the differential transformers 513 and a motor control portion 733 for controlling the electric power to be supplied to the motor 510 according to the quantity of movement obtained by the warped shape calculating portion 732.

The operation of this modification will now be described with reference to the flow chart shown in FIG. 36.

In step S130, the differential transformers 731 detect the quantity of movement of each of the wires 513. In step S131, the warped shape calculating portion 732 calculates the angle of warp of the warp-enabled portion 505 on the basis of the aforesaid quantity of movement. In step S132, the motor control portion 733 stops the motor 510 in step S133 when the angle of warp is a predetermined maximum angle of warp.

Figure 37:
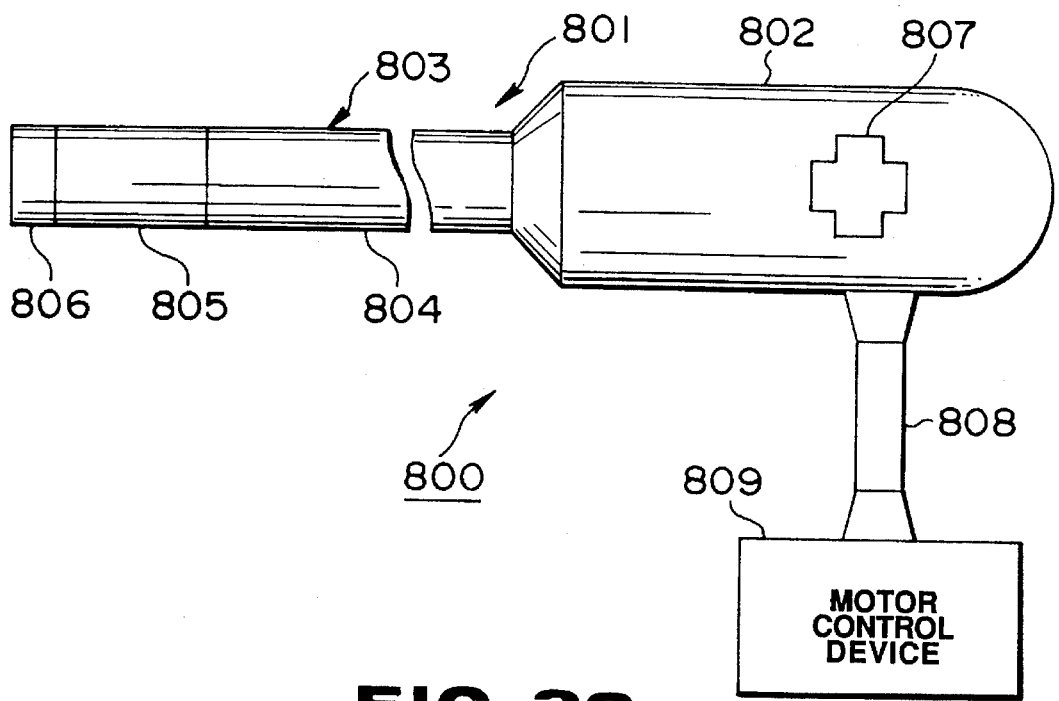
FIGS. 37 to 40 illustrate an eighth embodiment of the present invention.
Figure 38:
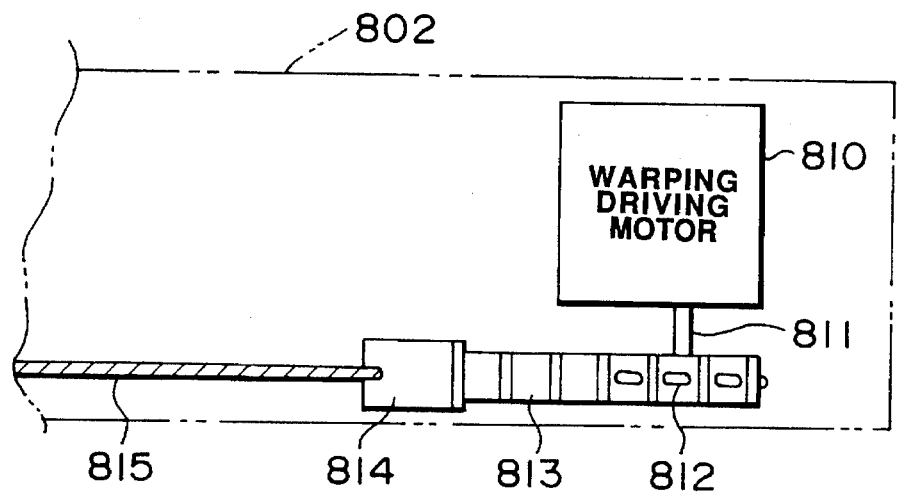
Figure 39:
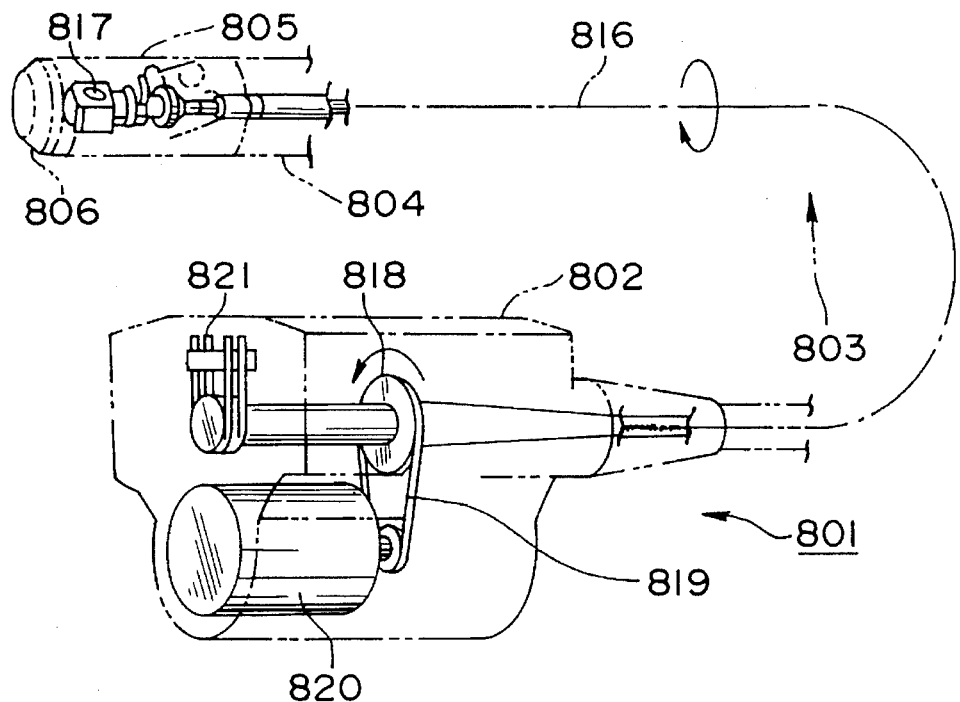
Figure 40:
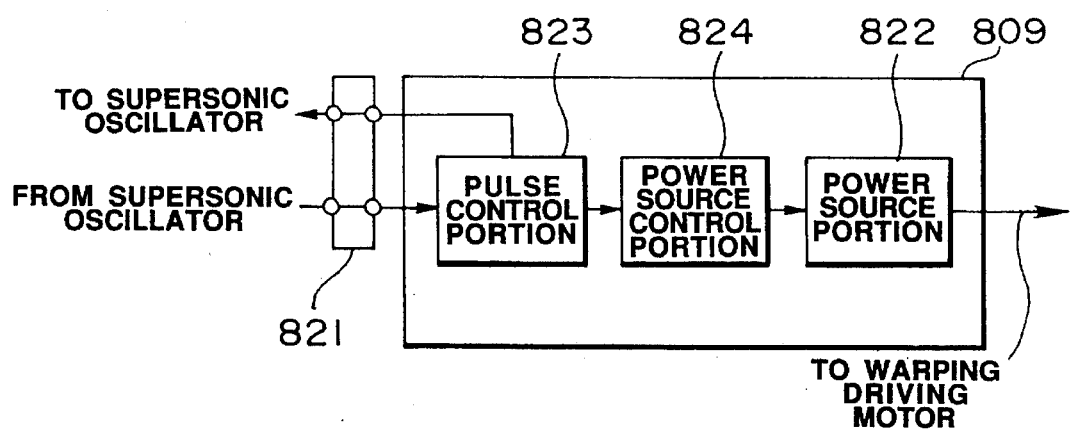

FIGS. 37 to 40 illustrate an eighth embodiment of the present invention. FIG. 37 is an overall structural view which illustrates an electromotive warping type endoscope apparatus. FIG. 38 is a structural view which illustrates a portion of a warping mechanism. FIG. 39 is a perspective view which illustrates the endoscope featuring a supersonic driving system. FIG. 40 is an electric block diagram which illustrates a motor control device.

This embodiment is arranged in such a manner that a supersonic sensor is used in place of the pressure sensor according to the second embodiment.

An electromotive warping type endoscope apparatus 800 shown in FIG. 37 comprises an electronic endoscope 801, a motor control device 809 and a light source device (omitted from illustration).

The electronic endoscope 801 has an operation portion 802 and an insertion portion 803 connected to the operation portion 802 and formed into an elongated shape so as to be inserted into a subject to be inspected. The insertion portion 803 has, when viewed from the operation portion 802, a soft portion 804 having flexibility, a warp-enabled portion 805 structured in such a manner that it can be warped and a leading unit 806 connected sequentially.

The warp-enabled portion 805 is constituted by connecting a plurality of warping blocks (omitted from illustration) so as to be warped vertically/laterally when a warping operation switch 807 disposed in the operation portion 802 is operated. A universal cord 808 is connected to the side portion of the operation portion 802 and the motor control device 809 is connected to the universal cord 808.

The operation portion 802 includes a DC warping motor 810 for vertically warping the warp-enabled portion 805, a sprocket 812 secured to a drive shaft 811 of the warping motor 810 and a chain 813 engaged with the sprocket 812. Wires 815 are connected to the two end portions of the chain 813 via connection members 814 (one of them is illustrated). The wires 815 are inserted into the soft portion 804 and the warp-enabled portion 805 and are connected to the front warping block (omitted from illustration) of the warp-enabled portion 805.

Although a mechanism for laterally warping the warp-enabled portion 805 is also disposed, it is formed into a similar structure and therefore its description is omitted here.

FIG. 39 is a schematic view which illustrates a supersonic sensor and a supersonic driving system. In FIG. 39, the aforesaid driving motor and the like are omitted for convenience.

The insertion portion 803 has a rotatable, flexible and coil-like flexible shaft 816 inserted thereto. The aforesaid leading unit 806 includes a fixed supersonic oscillator 817 which is rotated by the flexible shaft 816. A stepped gear 818 is secured to a portion of the flexible shaft 816 adjacent to the operation portion 802, so that the stepped gear 818 is rotated in synchronization with a motor 820 for the supersonic sensor via a stepped motor belt 819. A slip ring mechanism 821 is disposed in the end portion of the side portion of the flexible shaft 816. Electric wires (omitted from illustration) connected to the supersonic oscillator 817 pass through the central portion of the flexible shaft 816 until it reaches the slip ring mechanism 821. Electric wires pass through the inside portion of the universal cord 808 so as to be introduced from the slip ring mechanism 821 to the inside portion of the motor control device 809. As a result, the supersonic oscillator 817 and the motor control device 809 can be electrically connected to each other regardless of the rotation of the flexible shaft 816.

The motor control device 809 shown in FIG. 40 includes a power source portion 822 for supplying electric power to the warping motor 810, a pulse control portion 823 for transmitting driving pulses to the supersonic oscillator 817 and also receiving reflected echo signal and a power source control portion 824 for receiving an output from the pulse control portion 823 denoting information about the time taken between the signal transmission and the receipt, the power source control portion 824 further performing control to reduce the electric power supplied from the power source portion 822 depending upon an assumption made that the distance to the subject of the inspection, for example, to the body wall is short if the aforesaid time is shorter than a predetermined time.

In the structure thus arranged, the pulse control portion 823 included in the motor control device 809 transmits the driving pulses to the supersonic oscillator 817. As a result, the driving pulses are introduced to the supersonic oscillator 817 via the slip ring mechanism 821. The supersonic oscillator 817 emits supersonic beams. The supersonic beams are reflected by the body wall and return to the supersonic oscillator 817. The reflected echo signal received by the supersonic oscillator 817 is returned to the pulse control portion 823 via the slip ring mechanism 821. If the time taken for the aforesaid process is shorter than a predetermined time, that is, if the distance from the body wall is shorter than a predetermined length, the pulse control portion 823 transmits a control signal to the power source control portion 824. As a result, the power source control portion 824 reduces electric power to be supplied from the power source portion 822 to the driving motor 810. Thus, control is performed in such a manner that the warping velocity of the warp-enabled portion 805 is lowered. The velocity control is given priority to the instruction made with the warping operation switch 807.

Since the supersonic oscillator 817 is rotated to perform radial scanning by the supersonic sensor motor 820, the distance in all of the directions covering 360° can be measured.

The structure comprising the supersonic oscillator 817 for mechanically performing the radial scanning operation may be replaced by a structure in which a plurality of fixed type supersonic oscillators are disposed in the warp-enabled portion or the soft portion so as to perform an electric scanning operation.

According to this embodiment, the supersonic oscillator 817 radially scanned and rotated by the supersonic sensor motor 820 is able to measure the distance in all of the directions covering 360°. Furthermore, the distance can be measured according to this embodiment as compared with the aforesaid embodiments in which the safety securing operation is performed in only a case in which the warp-enabled portion comes in contact with the body wall or the like. Therefore, a fact that the body wall is close to the warp-enabled portion can be confirmed prior to the contact with the body wall or the like. As a result, a safety securing operation such as lowering the warping velocity can be performed in advance (for example, by setting a predetermined distance). Therefore, the operability and safety in performing the warping operation can be improved.

The control of the warping velocity may be performed by another method in place of lowering the warping velocity in such a manner that the warping is stopped or the warp-enabled portion is moved in a different direction; for example, it is moved rearward.

Figure 41:
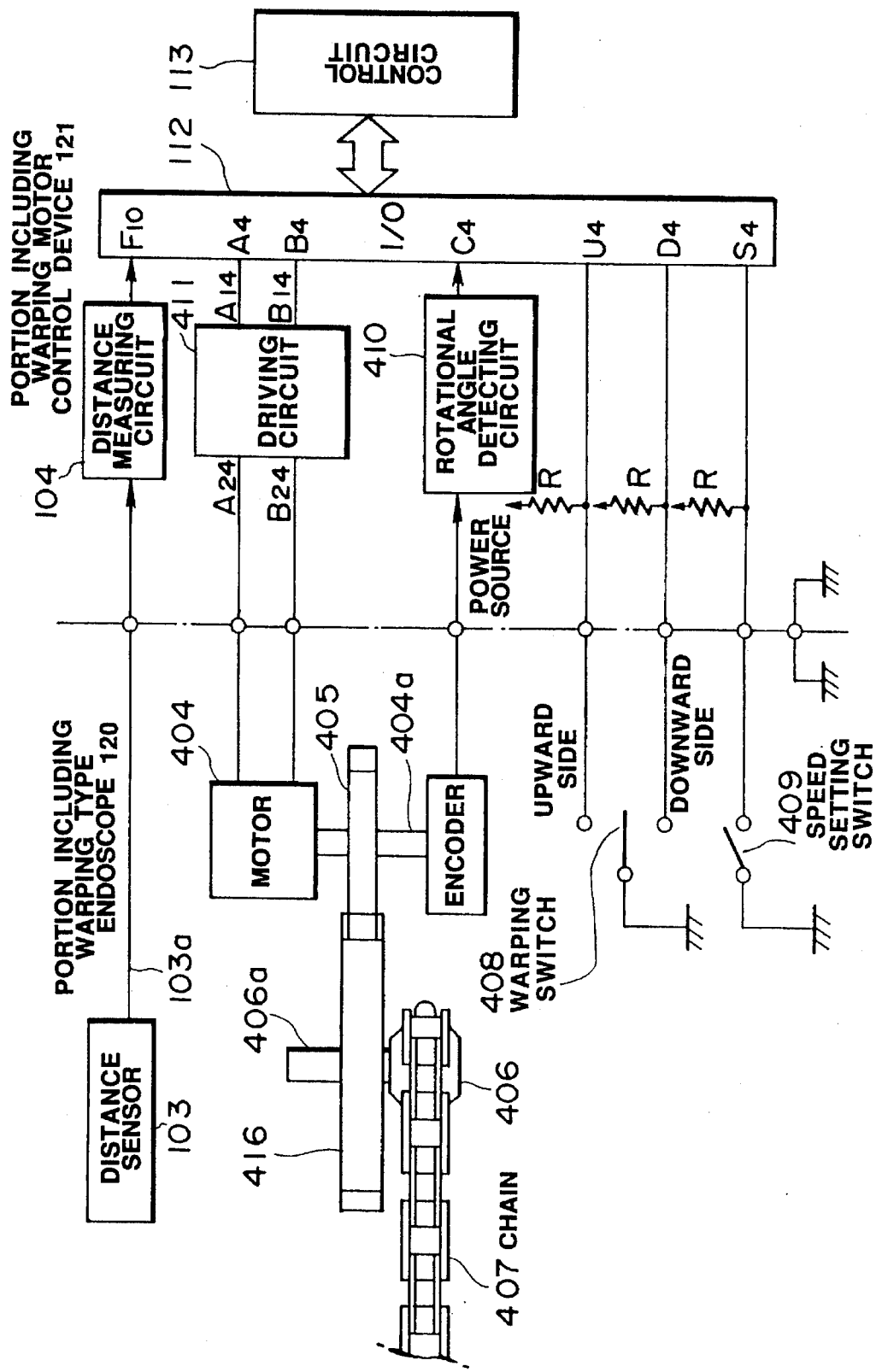

FIGS. 41 to 43 illustrate a ninth embodiment of the present invention. FIG. 41 is a structural view which illustrates an electromotive warping type endoscope apparatus featuring an essential portion. FIG. 42 is a structural view which illustrates the leading portion of an endoscope. FIG. 43 is a flow chart which illustrates a warping velocity control operation.

The overall structure of the electromotive warping type endoscope apparatus according to this embodiment is structured similarly to the electromotive warping type endoscope apparatus 301 shown in FIG. 1. However, it has an electromotive warping type endoscope 120 shown in FIG. 41 in place of the endoscope 302 and has a warping motor control device 121 shown in FIG. 41 in place of the warping motor control device 314 shown in FIG. 1. Since the overall structure of the electromotive warping type endoscope apparatus according to this embodiment is structured similarly to the electromotive warping type endoscope apparatus according to the first embodiment, its illustration and description are omitted here.

The electromotive warping type endoscope 120 has a proximity sensor such as an infrared-ray sensor in place of the pressure sensor according to the second embodiment so as to control the warping velocity.

FIGS. 42(*a*) and 42(*b*) illustrate only a leading unit 101 and a warp-enabled portion 102 of the insertion portion of the electromotive warping type endoscope 120.

The leading unit 101 has a proximity sensor 103 on the front surface thereof, the proximity sensor 103 having a signal line 103*a* inserted into the insertion portion in the axial direction so as to be electrically connected to the warping motor control device 121. In a case where the proximity sensor 103 is an infrared-ray sensor, it irradiates infrared rays from the front surface of the leading unit 101 and also receives the infrared rays reflected by a subject of the inspection so as to measure the distance to the subject of the inspection.

Referring to the drawings, reference numerals 122 and 123 represent the emission ends of a light guide fiber, 124 represents an incident end of an image guide fiber, 125 represents a forceps channel port and 126 represents an air/water supply nozzle.

FIG. 41 illustrates an electrical connection established between the electromotive warping type endoscope 120 and the warping motor control device 121 and also illustrates a portion of a warping mechanism.

The warping motor control device 121 shown in FIG. 41 has a distance-measuring circuit 104 for receiving an output signal transmitted from the proximity sensor 103, the distance-measuring circuit 104 being used in place of the resistance-detecting circuit 414. The warping motor control device 121 has an I/O 112 in place of the I/O 412 according to the second embodiment shown in FIG. 10 and has a control circuit 113 in place of the control circuit according to the second embodiment shown in FIG. 10.

The same structures and operations as those according to the second embodiment are given the same reference numerals and their descriptions are omitted here.

In the thus arranged structure, since the warping operation and the operation for switching the warping velocity are the same as those according to the second embodiment and therefore their descriptions are omitted here.

The proximity sensor 103 always measures the distance and the distance-measuring circuit 104 converts the output signal transmitted from the proximity sensor 103 into distance data so as to output distance data to the control circuit 113 via a terminal F10 of the I/O 112. The control circuit 113 always makes a comparison between a predetermined distance and the present distance measured by the proximity sensor 103. The control circuit 113 discriminates that the present state is a dangerous state if the measured distance is shorter than the predetermined distance in step S52 according to the flow shown in FIG. 43. In step S53, the control circuit 113 stops the warping operation.

In a case where the discrimination is made that the present state is a dangerous state, the warping velocity may be lowered to one-half or less of a predetermined warping velocity; for example, "1" to slow the warping operation. As an alternative to this, if the measured distance is zero, the control may be performed in such a manner that the warp-enabled portion is moved in a different direction from the direction in which the warp-enabled portion is moved; for example, it may be returned in the opposite direction.

If the measured distance is longer than the predetermined distance in step S52, the control circuit 113 discriminates that the present state is a safe state and causes the warping operation to be continued in step S53.

According to this embodiment, the distance can be measured and therefore a fact that the body wall is positioned close to the warp-enabled portion can be confirmed prior to its contact with the body wall. Therefore, a safety securing operation such as stopping the warp-enabled portion can be performed as compared with each of the aforesaid embodiments (except for the eighth embodiment) in which the safety securing operation can be performed in only the case where the warp-enabled portion comes in contact with the body wall or the like. As a result, the operability and safety in the warping operation can be improved with the apparatus according to this embodiment.

Figure 44:
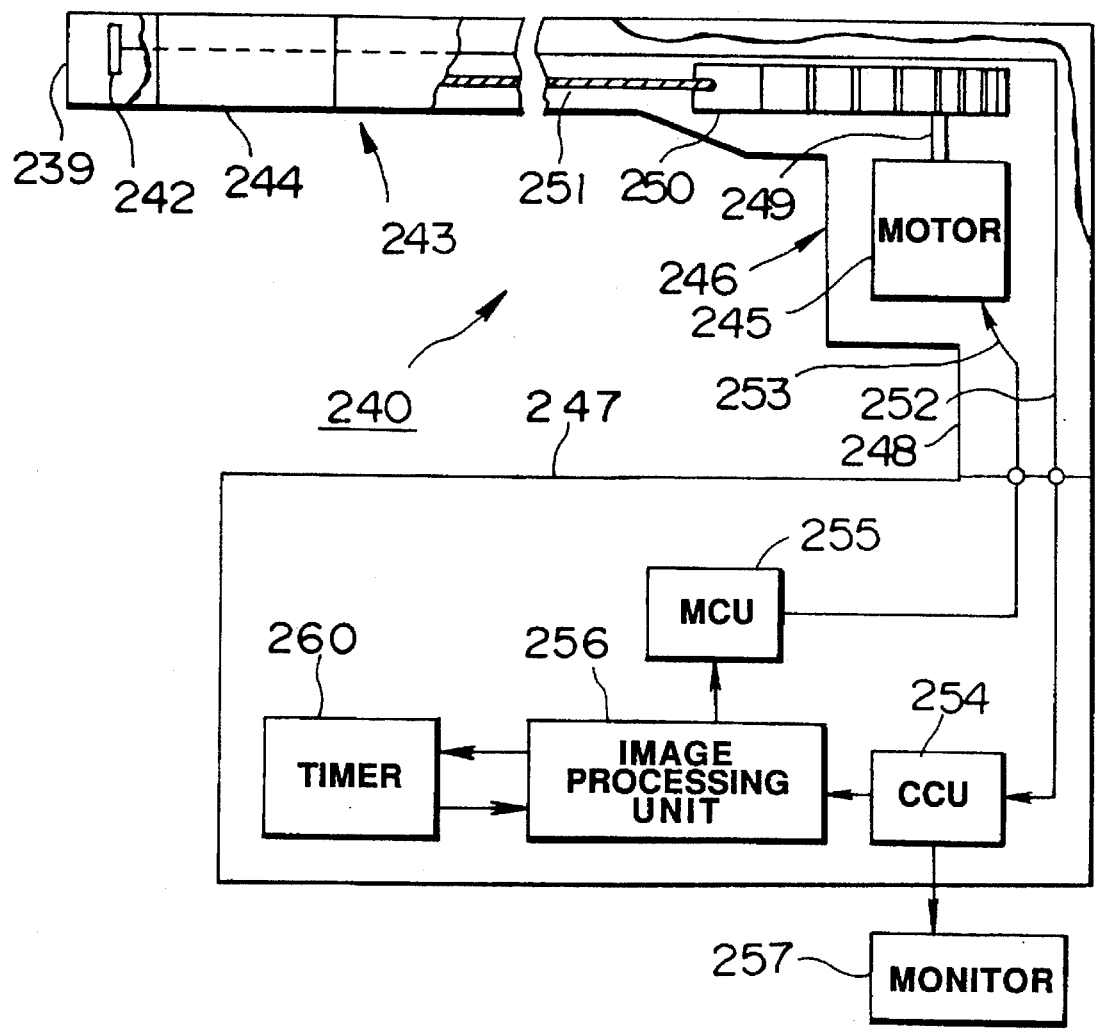
FIGS. 44 to 46 illustrate a tenth embodiment of the present invention, where
Figure 45:
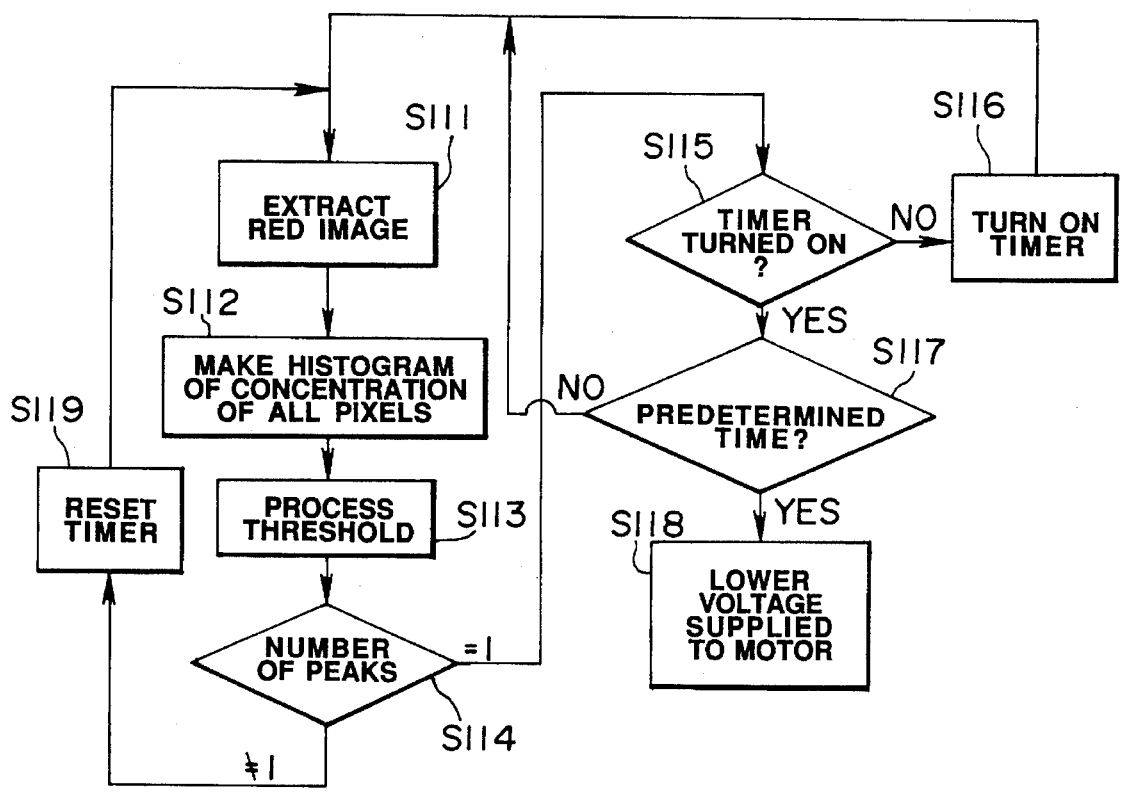
Figure 46:
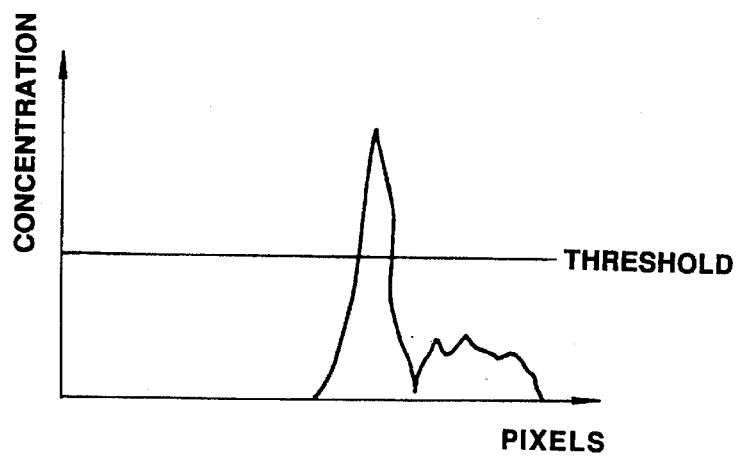

FIGS. 44 to 46 illustrate a tenth embodiment of the present invention. FIG. 44 is an overall schematic structural view which illustrates the electromotive warping type endoscope apparatus, FIG. 45 is a flow chart which illustrates the operation of controlling the warping velocity, and FIG. 46 is a histogram which illustrates the pixel density.

The electromotive warping type endoscope apparatus 240 according to the embodiment shown in FIG. 44 comprises an electromotive warping type electronic endoscope 241, an external control device 247 for controlling the warping operation of the endoscope 241, as well as processing signals imaged by the endoscope 241, a monitor 257, and a light source device (omitted from illustration).

The endoscope 241 comprises an insertion portion 243 having a leading portion 239, which includes a CCD 242 for image-sensing the inside portion of a subject to be inspected, and a warp-enabled portion 244 disposed adjacent to the leading portion 239, the insertion portion 243 being arranged in such a manner that it can be inserted into the subject of the inspection. The endoscope 242 further comprises an operation portion 246 including a motor 245 for warping the warp-enabled portion 244 and a connection portion 248 connected to the operation portion 246 and the external control device 247.

A sprocket (omitted from illustration) is secured to the motor shaft 249 extending from the motor 245, and a chain 250 is wound around the sprocket. Warping operation wires 251 (one of which is illustrated here) secured to the front warping block (omitted from illustration) of the warp-enabled portion 244 are secured to the two end portions of the chain 250. When the warping operation wires 251 are pulled/slackened, the warp-enabled portion 244 can be warped.

A CCD signal cable 252 extending from the CCD 242 passes through the connection portion 248 and is electrically connected to a camera control unit (hereinafter abbreviated as "CCU") 254 disposed in the external control device 247 and acting to control the operation of the CCD 242 and to process an imaged signal into a standard video signal. On the other hand, a motor cable 253 extending from the motor 245 passes through the connection portion 248 and is electrically connected to a motor control unit (hereinafter abbreviated as "MCU") 255 disposed in the external control device 247 and acting to control the operation of the motor 245.

The external control device 247 has an image processing unit 256 which generates the histogram of the density of each pixel from the standard video signal transmitted from the CCU 254 and makes a comparison between the obtained histogram and a predetermined threshold so as to control the MCU 255. The image processing unit 256 detects a "red image" to be described later and transmits a control signal to the MCU 255 if the time measured by a timer, which measures the time in which the aforesaid state continues, is longer than a predetermined reference time.

An external monitor 257 is connected to the CCU 254 so as to display an image supplied from the CCD 254.

The operation of this embodiment will now be described with reference to the flow chart shown in FIG. 45. If the insertion portion 243 of the endoscope 241 is inserted into a human being's colon, for example, the tract of the colon is bent and complex, causing the leading portion of the endoscope to easily come in contact with the tract wall of the colon. If the leading portion 239 of the insertion portion 243 is introduced and it comes in contact with the tract wall, a full red image (a so-called "red image") can be displayed on the monitor 257. The reason for this lies in that the focus cannot be adjusted and the overall scope becomes reddish in a state where the leading portion 239 comes in contact with the tract wall or it is positioned close by it, since the tract wall of a living body such as the colon is reddish in general.

According to this embodiment, the "red image" is detected and therefore the leading portion of the insertion portion detects a dangerous state in which the leading portion of the insertion portion comes in close contact with the tract wall of the colon or the like. The operation of detecting the "red image" and the warping velocity control will now be described with reference to the flow chart shown in FIG. 45.

In step S111 shown in FIG. 45, the image processing unit 256 included by the external control device 247 extracts an R (red) component of the image signal supplied from the CCD 242. In step S112, its density histogram is made. Then, the obtained density histogram is subjected to a threshold process by using a predetermined threshold in step S113. The "threshold process" is a process of counting the number of peaks in the density histogram which exceed the threshold.

Since all of the pixels are composed of uniform R components in the case of the "red image", the density histogram is made in such a manner that one peak is generated when the density is at a predetermined level as exemplified in FIG. 46. In other cases, for example, the density histogram of a diseased part has a plurality of peaks, each of which does not exceed the threshold.

As described above, only one peak is observed after the threshold process has been completed. Therefore, if the number of the peaks is one in step S114, a discrimination is made that the present state is the state of the "red image".

In order to discriminate whether or not the state of the "red image" continues over a predetermined reference time in step S115, the image processing unit 256 discriminates whether or not the timer 260 is turned on. If it is negated, the image processing unit 256 turns on the timer 260 in step S116. Then, the timer 260 starts counting the continuation time of the state of the "red image".

The aforesaid image processing unit 256 processes the image in succession. Therefore, if a discrimination of YES (if the timer 260 is turned on) is made, whether or not the time in which the number of the peaks reaches the predetermined reference time is discriminated in step S117, so that a discrimination is made whether or not the change in control of the warping velocity of the warp-enabled portion is performed.

If it reaches the predetermined time, a discrimination is made that the state of the "red image" has been continued and the present state is a dangerous state. Therefore, the image processing unit 256 transmits a control signal for lowering the voltage supplied to the motor 245 to the MCU 255 in step S118. The MCU 255 lowers the voltage supplied to the motor 245 in response to the control signal supplied from the image processing unit 256. Therefore, the warping velocity of the warp-enabled portion 244 is lowered and, in addition, it cannot be warped strongly. As a result, an excessive warping operation by an operator is forcibly inhibited.

If the number of the peaks is 1 in step S114, the present state is not the state of the "red image". Therefore, the timer is reset in step S119.

According to this embodiment, in a case where the state of the "red image" has been continued, a discrimination is made that the warp-enabled portion is in contact with the tract wall or the same is close to the tract wall and the warping velocity is forcibly lowered so as to inhibit strong warping. Therefore, the accident due to the warping operation can be prevented. Furthermore, since the normal warping operation can be performed until the predetermined time in which the state of the "red image" is continued is passed, a blind operation which is required to complete the insertion technique can be performed. The insertion feasibility is not hindered. As described above, according to this embodiment, the operability and the safety of the warping operation can be improved.

Furthermore, according to this embodiment, the aforesaid density analysis may be replaced by the chromaticity analysis which is used as the basis of the warping velocity control. The control of the warping velocity is not limited to the deceleration and it may be performed in such a manner that the warping operation is stopped or the warp-enabled portion is moved in a direction which is different from the previous direction in which the warp-enabled portion was moved.

In addition, the electronic endoscope may be replaced by an optical fiber endoscope having a camera mounted on the outer surface thereof which supplies a video signal.

Figure 47:
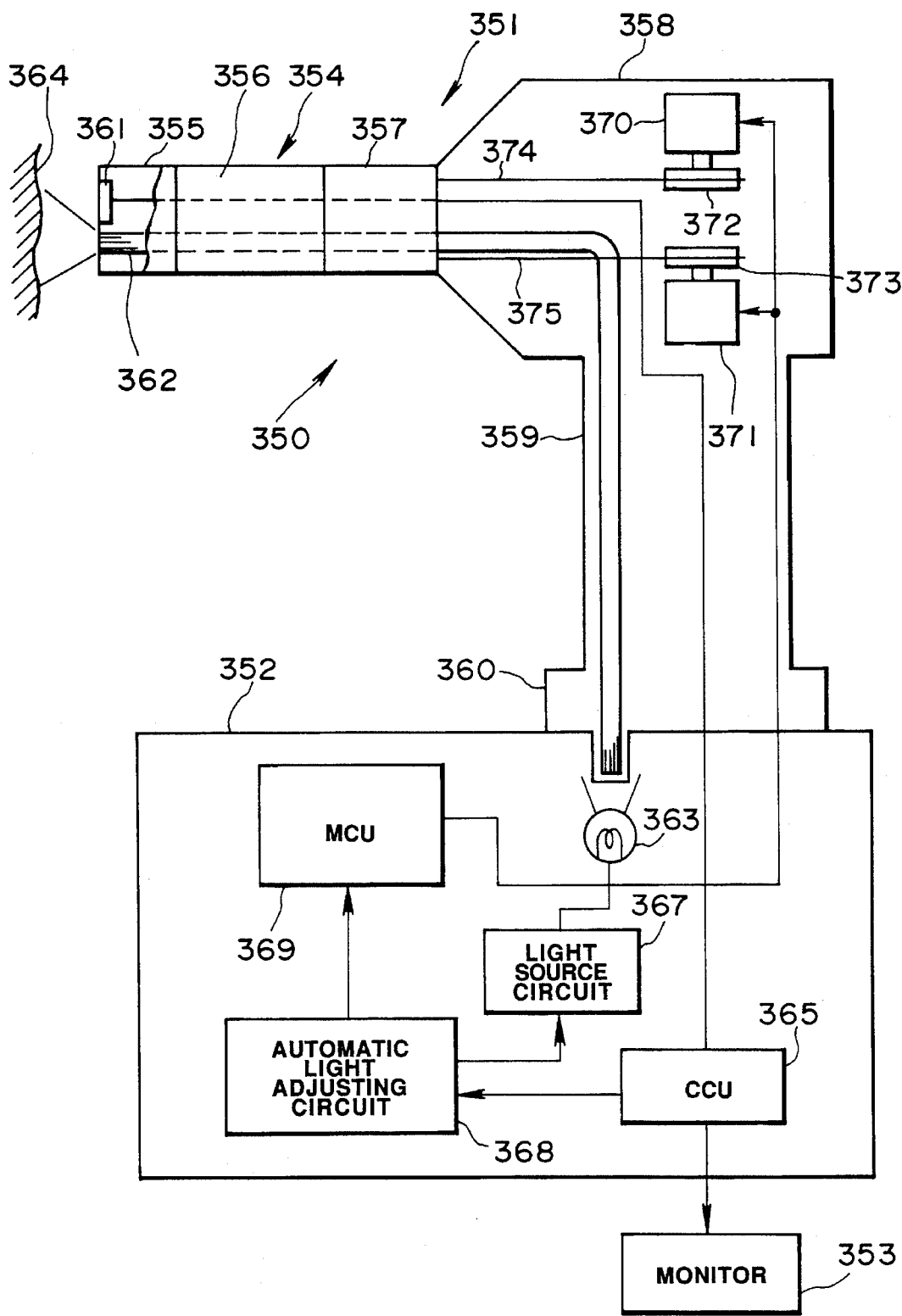
FIG. 47 is a structural view which illustrates the electromotive warping type endoscope apparatus according to an eleventh embodiment of the present invention.

FIG. 47 is a structural view which illustrates an electromotive endoscope apparatus according to an eleventh embodiment.

An electromotive warping type endoscope 350 shown in FIG. 47 comprises an endoscope 351, an external control device 352 and a monitor 353.

The endoscope 351 has an elongated insertion portion 354. The insertion portion 354 comprises, from the leading portion, a leading unit 355, a warp-enabled portion 356 which can be warped and a soft portion 357 having flexibility, which are sequentially disposed. The insertion portion 354 has, in the base portion thereof, an operation portion 358. A universal cable 359 extends from the side portion of the operation portion 358. The universal cable 359 has a connector 360 fastened to the leading portion thereof, so that the universal cable 359 is detachably connected to the external control device 352.

A light guide 355 for transmitting illuminating light is inserted into the insertion portion 354. Furthermore, the leading unit 355 of the insertion portion 354 has a solid-state imaging sensing device 361. In addition, the leading portion of the light guide 362 is disposed at the leading unit 355. The rear end portion of the light guide 362 is inserted into the operation portion 358, the universal cord 359 and the connector 360.

The endoscope 351 is detachably connected to the external control device 352 via the connector 360, so that illuminating light emitted from a light source 353 disposed in the external control device 352 is transmitted to the leading portion of the insertion portion via the light guide 362. As a result, a subject 364 of the inspection is irradiated with the illuminating light.

The solid-state image sensing device 361 is connected to a CCU 365 included in the external control device 352, so that a video signal imaged by the solid state image sensing device 361 is processed by the CCU 365 before it is transmitted to the monitor 353.

The operation portion 358 of the endoscope 351 includes warping motors 370 and 371. Furthermore, angle wires 374 and 375 are wound around pulleys 372 and 373 connected to the warping motors 370 and 371. The warping motors 370 and 371 are connected to an MCU 369 included by the external control device 352, so that the warping motors 370 and 371 are rotated by driving electric power supplied from the MCU 369.

The external control device 352 has a light source circuit 367 for operating the light source 363 and an automatic light adjusting circuit 368 for controlling the light quantity to be emitted from the light source 363 in response to an output video signal supplied from the CCU 365. The automatic light adjusting circuit 368 detects the brightness level of an observed image in response to the output video signal supplied from the CCU 365 and adjusts the light to be emitted from the light source 363 by controlling the light source circuit 367 according to the aforesaid level. The automatic light adjusting circuit 368 also transmits a brightness level signal to the MCU 369. In response to the brightness level signal, the MCU 369 discriminates that the subject is positioned closely if the brightness level of light reflected by the subject 364 to be inspected is high and lowers the motor driving electric power. If the brightness level is low, it discriminates that the subject is positioned away from the insertion portion and raises the level of the motor driving electric power. As described above, it supplies driving electric power corresponding to the distance from the subject 364 to be inspected to each of the warping motors 370 and 371.

According to this embodiment, when the leading unit 355 approaches the subject 364 to be inspected, the quantity of illuminating light irradiated from the leading portion of the light guide 362 and reflected from the subject 364 to be inspected is increased. As a result, the light quantity to be made incident upon the solid-state image sensing device 361 is increased. Therefore, the brightness level of the video signal processed by the CCU 365 is raised and the automatic light adjusting circuit 368 transmits a brightness level signal to the light source circuit 367 so as to reduce the light quantity. The brightness level signal is simultaneously transmitted to the MCU 369. As a result, the MCU 369, which has received the aforesaid signal, switches the electric power level to a low level. Thus, the rotation speed of the motor is lowered in proportion to the distance between the moving leading unit 3 and the subject 364 to be inspected, causing the warping velocity of the warp-enabled portion to be lowered.

If the leading unit 355 moves away from the subject 364 to be inspected, the level of the aforesaid brightness level signal is lowered and therefore the MCU 369 switches the motor driving electric power level to a high level. That is, the rotation speed of the motor is raised in proportion to the distance from the leading unit 355 to the subject 364 to be inspected, causing the warping velocity of the warp-enabled portion to be raised.

As described above, according to this embodiment, the warping velocity is controlled in accordance with the distance from the subject to be inspected. Therefore, the warping velocity can be lowered when a portion adjacent to the body wall is observed, causing the high velocity alternation of the observed image to be inhibited. As a result, the observation can be performed easily. Also according to this embodiment, the warping velocity can be raised in a case where the warping is performed at a position away from the body wall. Therefore, the warping to an arbitrary position can be quickly performed and therefore the operability can be improved.

Figure 48:
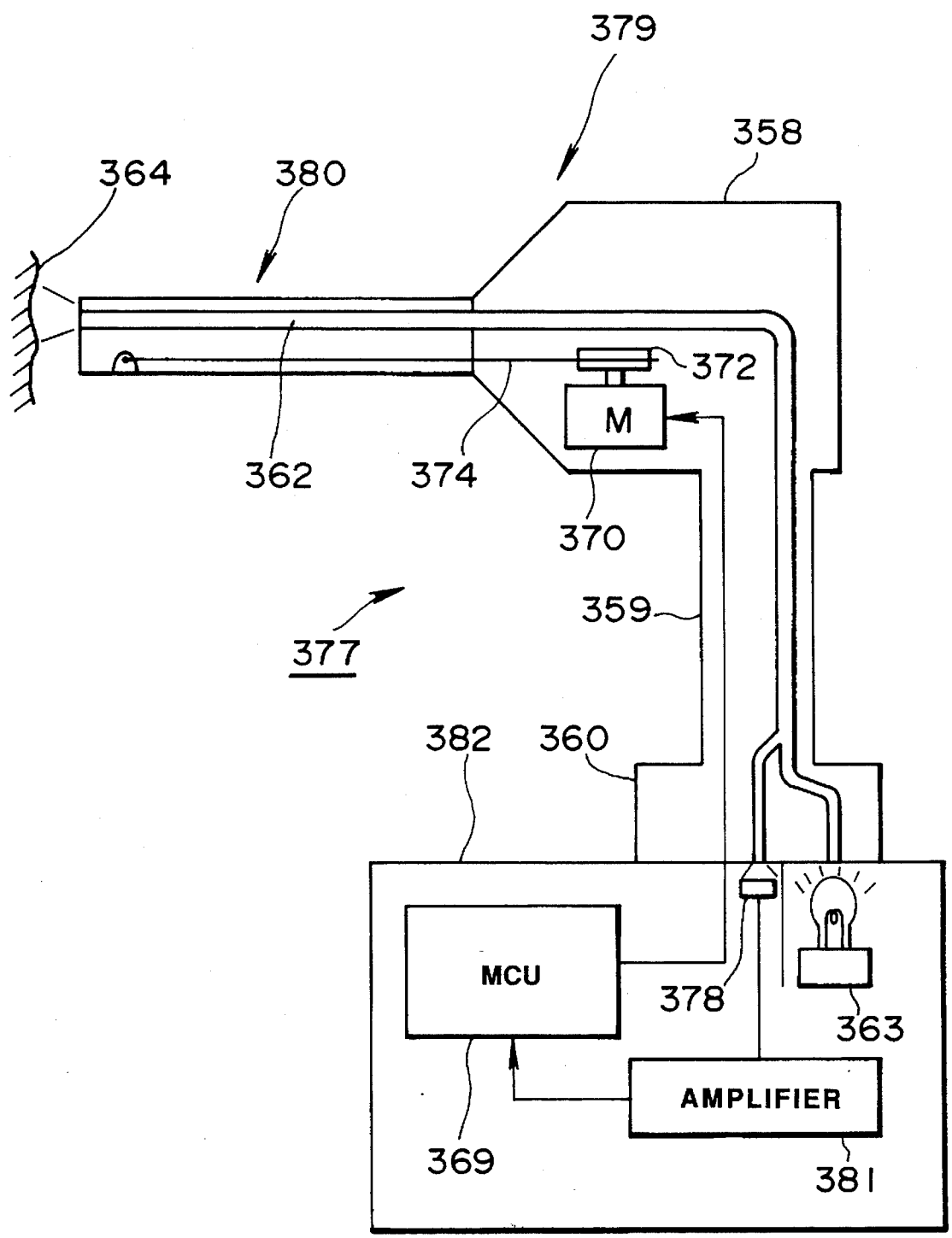
FIG. 48 is a structural view which illustrates the electromotive warping type endoscope apparatus according to a twelfth embodiment of the present invention.

FIG. 48 is a structural view which illustrates an electromotive warping type endoscope apparatus according to a twelfth embodiment of the present invention.

An endoscope device 377 according to this embodiment uses a portion of the light guide to introduce reflected light as an alternative to using the CCU and the automatic light adjusting circuit according to the eleventh embodiment for the purpose of detecting the quantity of light reflected from a subject to be inspected. Furthermore, a photosensor 378 made of, for example, a Cd-S cell or the like for receiving reflected light and an amplifier 375 for amplifying an output signal from the photosensor 378 are provided.

A light guide 362 is inserted into an insertion portion 380 of the endoscope 379 similarly to the eleventh embodiment. The rear end portion of the light guide 362 is inserted into an operation portion 358, a universal cord 359 and a connector 360, the light guide 362 being branched into two portions in the connector 360. The end portion of one of the two portions of the branched light guide 362 is disposed to face a light source 363 included by an external control device 382, while another end portion being disposed to face the photosensor 378 provided for the external control device 382.

The operation portion 358 has a warping motor 372 similar to that in the eleventh embodiment. Furthermore, an angle wire 362 inserted into the insertion portion 380 is wound around a pulley 372 disposed on the rotational shaft of the warping motor 372.

The photosensor 378 is connected to the amplifier 381 and an output signal from the photosensor 378 is amplified and supplied to the MCU 369. The MCU 369 controls the driving electric power according to the level of an output signal from the amplifier 381 and also drives the warping motor 370 according to the quantity of light reflected by the subject 364 to be inspected.

In a case where the warp-enabled portion of the insertion portion 380 is warped in, for example, downward direction, a warping switch (omitted from illustration) is switched on in the downward direction, causing the MCU 369 to supply driving electric power to the warping motor 370. As a result, the warping motor 370 is rotated and the angle wire 374 is pulled, causing the warp-enabled portion to be warped in the downward direction.

When the leading unit of the insertion portion 380 has approached the subject 364 to be inspected, the quantity of light emitted from the leading portion of the light guide 362 and reflected by the subject 364 to be inspected is increased. Also, the quantity of reflected light introduced through one of the branched portions of the light guide 362 is increased. As a result, the level of the output from the photosensor 378 is raised. When an output signal transmitted from the photosensor 378 is supplied to the MCU 369 via the amplifier 381 and the level of the input has exceeded a predetermined value, the MCU 369 reduces the value of the electric power to be supplied to the motor. As a result, the rotation speed of the motor is lowered in proportion to the distance between the moving leading unit and the subject 364 to be inspected. Therefore, the warping velocity of the warp-enabled portion is lowered.

If the leading unit has moved away from the subject 364 to be inspected, the rotation speed of the motor is raised and the warping velocity of the warp-enabled portion is raised.

As described above, also according to this embodiment, the warping velocity is controlled according to the distance from the subject to be inspected similarly to the eleventh embodiment. Therefore, observation can be performed easily.

Figure 49:
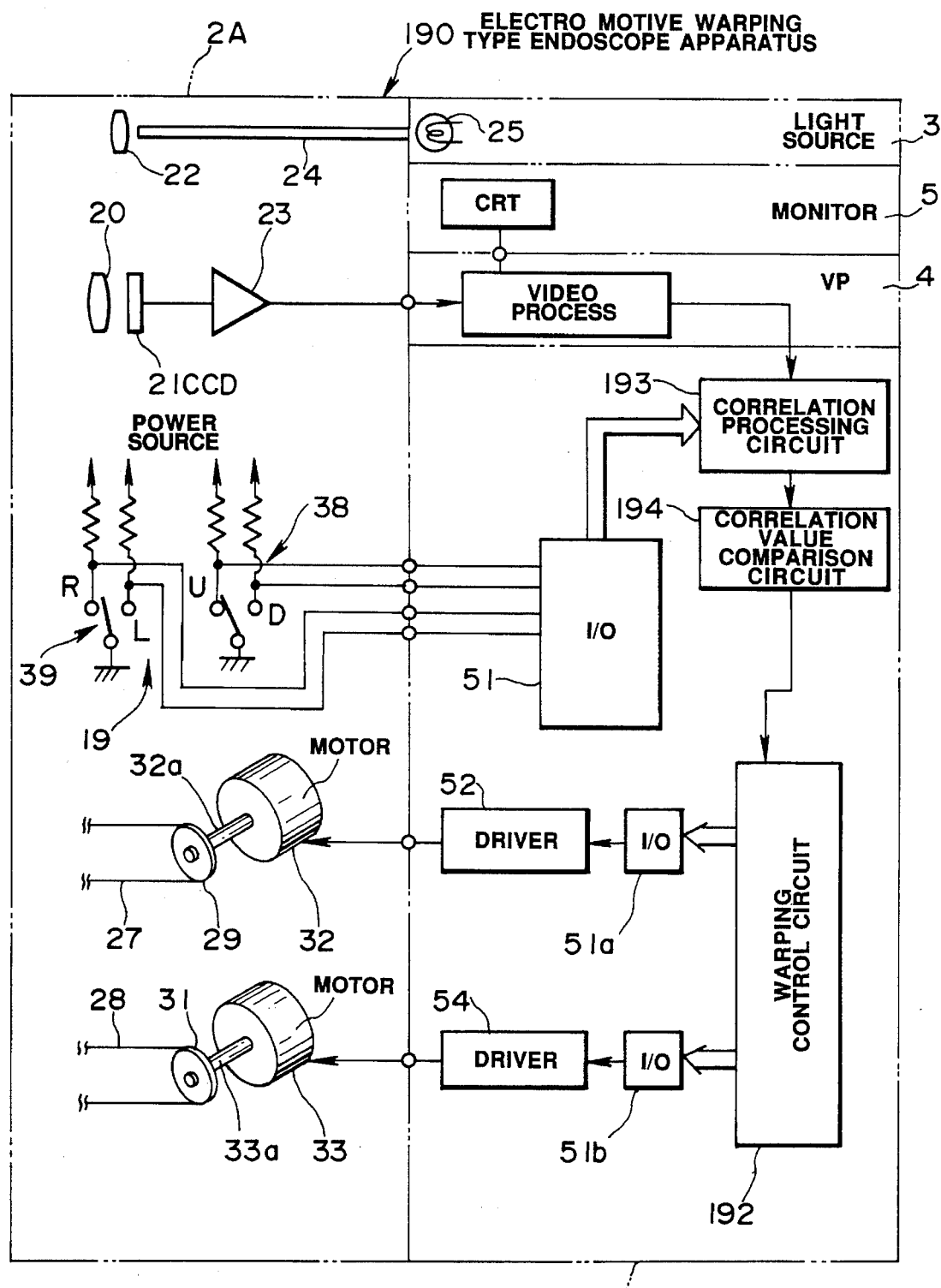
FIGS. 49 to 51 illustrate a thirteenth embodiment of the present invention, where
Figure 50:
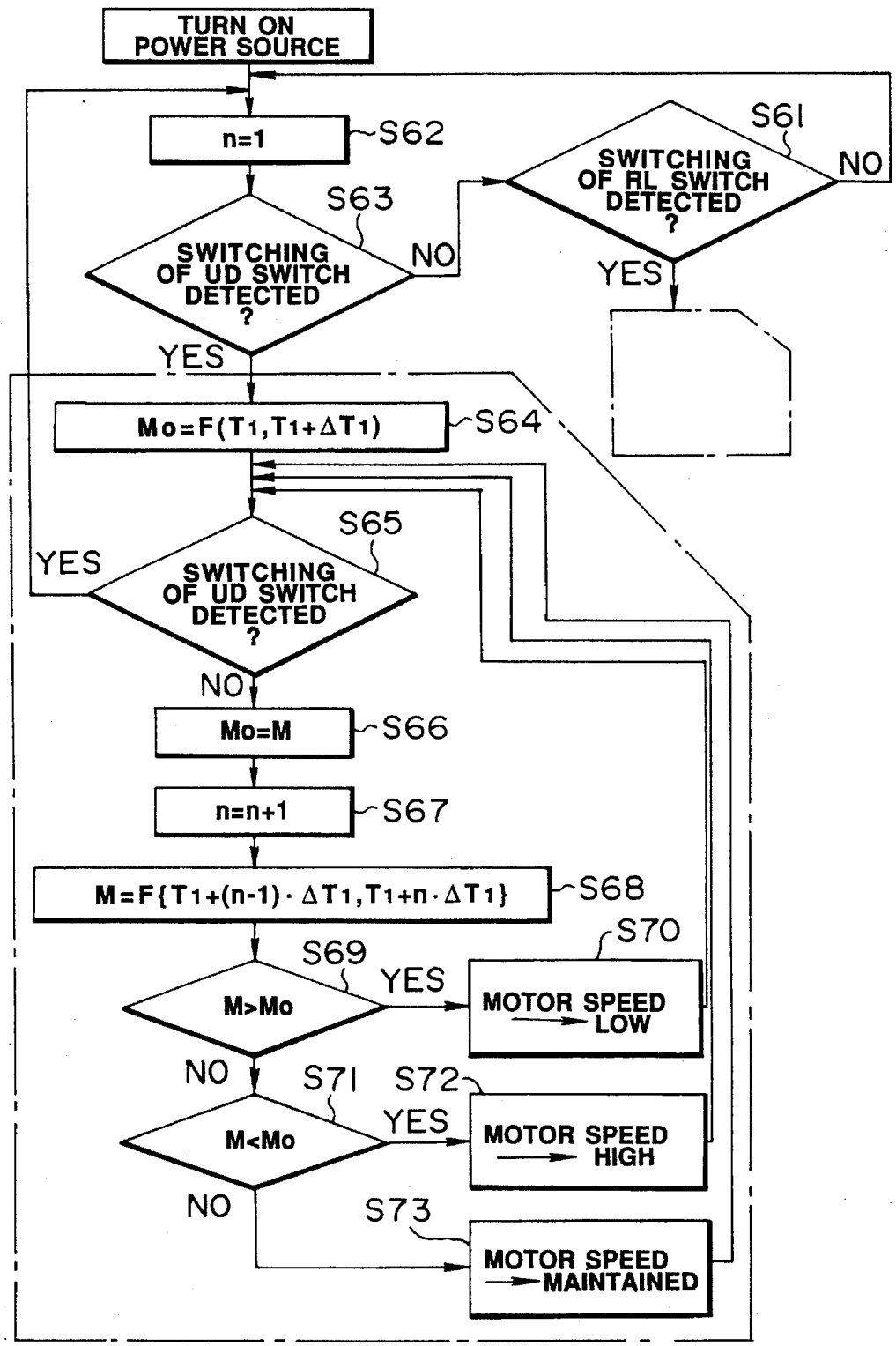
Figure 51:
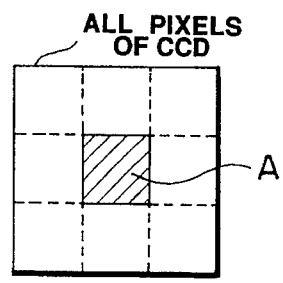

FIGS. 49 to 51 illustrate a thirteenth embodiment of the present invention. FIG. 49 is a structural view which illustrates an electromotive warping type endoscope apparatus featuring an essential portion, FIG. 50 is a flow chart which illustrates control of the warping velocity and FIG. 51 illustrates an image region for making an image correlation.

Since the electromotive warping type endoscope apparatus according to this embodiment has the same overall structure as that of the electromotive warping type endoscope according to the third embodiment shown in FIG. 16, the overall structural view is omitted here.

As shown in FIG. 49, an electromotive warping type endoscope apparatus 190 according to this embodiment comprises an electronic electromotive warping type endoscope 2A, a motor control device 191, the light source device 3, the video processor 4 and the monitor 5.

The electromotive warping type endoscope 2A is structured in such a manner that two encoders are omitted from the electromotive warping type endoscope 2 according to the third embodiment shown in FIG. 15. The motor control device 191 is structured in such a manner that two electric current detecting circuits, two A/D converters and two warping angle detecting circuits are omitted from the motor control device 6 according to the third embodiment shown in FIG. 15. The motor control device 191 has a warping control circuit 192 in place of the control device 48 of the electromotive warping type endoscope 2 according to the third embodiment shown in FIG. 15. The motor control device 191 has a correlation processing circuit 193 and a correlation value comparison circuit in addition to the electromotive warping type endoscope 2 according to the third embodiment shown in FIG. 15.

The thus structured apparatus according to this embodiment is arranged in a manner different from the apparatus according to the third embodiment, the apparatus according to this embodiment detecting the quantity of movement due to warping by using a video signal obtained by the video processor 4. The structures and the operations similar to those according to the third embodiment are given the same reference numerals and their descriptions are omitted here.

The electromotive warping type endoscope apparatus 190 shown in FIG. 49 uses an image obtained by the CCD 21 as detected information. According to the thus obtained detected information, the rotation speed of the warping motors 32 and that of the warping motor 33 are controlled. That is, the apparatus according to this embodiment controls the warping velocity of the warp-enabled portion 10 on the basis of the image.

The correlation processing circuit 193 shown in FIG. 49 receives the video signal transmitted from the video processor 4 so as to obtain the quantity of movement which becomes the maximum correlation between images at predetermined time intervals. The correlation processing circuit 193 is connected to the warping operation switch 19 via the I/O 51. The correlation processing circuit 193 obtains the maximum correlation between the images in period in which the warping operation switch 19 is switched on.

The correlation value comparison circuit 194 receives the quantity of movement at predetermined time intervals transmitted from the correlation processing circuit 193. The correlation value comparison circuit 194 makes the comparison between the quantity of the previous movement and the quantity of the movement after a predetermined time has passed.

Furthermore, the warping control circuit 192 controls the rotation speed of the warping motor 32 and that of the warping motor 33 on the basis of the result of the comparison transmitted from the correlation value comparison circuit 194.

Then, the operation of this embodiment will now be described with reference to the flow chart which illustrates the warping velocity control shown in FIG. 50.

Since the method of controlling the vertical warping motor 32 and that of controlling the lateral warping motor 33 are the same, the method of controlling the lateral warping motor 33 is omitted here. A flow chart continued from step S61 shown in FIG. 50 and surrounded by an alternate long and short dash line is omitted.

First, the power source is turned on, and n, which is the counted value of the time, is set to "1" in step S62 shown in FIG. 50. Then, in step S63, the correlation processing circuit 193 repeatedly performs confirmations according to external clocks (omitted from illustration) until the vertical warping switch 38 of the warping operation switch portion 19 detects a state where the switch is switched on.

In step S62, whether or not the lateral warping switch 39 is switched on is detected if the vertical warping switch 38 is switched off in step S61. Therefore, the detection whether or not the switch is switched on is always performed. In a case where the vertical warping switch is switched on, the flow proceeds to step S64. In a case where the lateral warping switch is on in the aforesaid state, the flow proceeds to steps surrounded by the alternate long and short dash line. The operations surrounded by the alternate long and short dash line are arranged to be similar to the operations in steps S64 to S73.

Then, description will be made about only the case in which the vertical warping switch 38 is switched on.

In step S64, the correlation processing circuit 193 obtains the correlation between an image at time T1 and an image at time (T1+ΔT1) after predetermined time ΔT1 has passed. As the at time image T1, an image obtained from the central pixel group A of 9 pixel groups formed by dividing all of the pixels of the CCD 21 by three in the longitudinal and lateral directions is used, the central pixel group A being designated by diagonal lines. Similarly, an image at time (T1+ΔT1) has the same window size as that of the central pixel group A. The image is determined while shifting the window in the direction of Y-axis and making the quantity of shift to be a variable. In the process of obtaining the correlation value between the two images, the quantity of shift is made to be a variable and the quantity of shift M0=F (T, T1+ΔT1) capable of obtaining the maximum correlation value is obtained. By also moving the window in the direction of X-axis and Z-axis as well as moving in the direction of Y-axis, the maximum correlation can be obtained further satisfactorily.

Then, in step S65, whether or not the vertical warping switch 38 is switched on is detected. If it is switched off, the warp-enabled portion 10 is in a stationary state and therefore the flow returns to initial step S62. If the state where the warping switch 38 is switched on is continued, M0 is set to M in step S66. Then, in step S67, setting is made that n=n+1, that is, n="2".

In step S68, the correlation processing circuit 193 obtains the correlation between an image at time (T1+T1) and that at time (T1+2ΔT1) after a predetermined time has passed. However, as the image at time (T1+ΔT1), an image obtained from the central pixel group A of 9 pixel groups formed by dividing all of the pixels of the CCD 21 by three in the longitudinal and lateral directions is used, the central pixel group A being designated by diagonal lines. Similarly, an image at time (T1+ 2ΔT1) has the same window size as that of the central pixel group A. The image is determined while shifting the window in the direction of the Y-axis and making the quantity of shift to be a variable. In the process of obtaining the correlation value between the two images, the quantity of shift is made to be a variable and the quantity of shift M0=F (T1+ΔT1, T1+2ΔT1) capable of obtaining the maximum correlation value is obtained.

In step S69, the correlation value comparison circuit 194 makes a comparison between shift quantities M0 and M. If M>M0,the movement of the image (that is, the warping velocity) becomes that the velocity in a period from T1 to (T1+ΔT1) is larger than that in a period from (T1+ΔT1) to (T1+2ΔT1). Therefore, control is performed via the warping control circuit 192 in such a manner that the rotation speed of the motor 32 is lowered.

In a case where a discrimination of NO is made in step S71, M=M0 and therefore the image is moving at a constant velocity. In this case, the rotation speed of the motor is not changed.

Then, whether or not the vertical warping switch 38 is switched off at time (T1+3ΔT1) is discriminated. If it is switched on, shift quantity M is substituted into M0 and the similar flow is repeated.

As a result of the aforesaid control, the image moving velocity becomes constant.

The electronic endoscope may be replaced by an optical fiber endoscope having an external camera mounted on the outer surface thereof, the external camera acting to supply video signal to be utilized.

According to this embodiment, the image moving velocity can be made constant regardless of the operation of the warping operation switch 19, that is, the quantity of the operation of the switch or the operation velocity. Therefore, the relationship between the warping operation and the quantity of warp can be easily recognized and therefore the operability can be improved.

Figure 52:
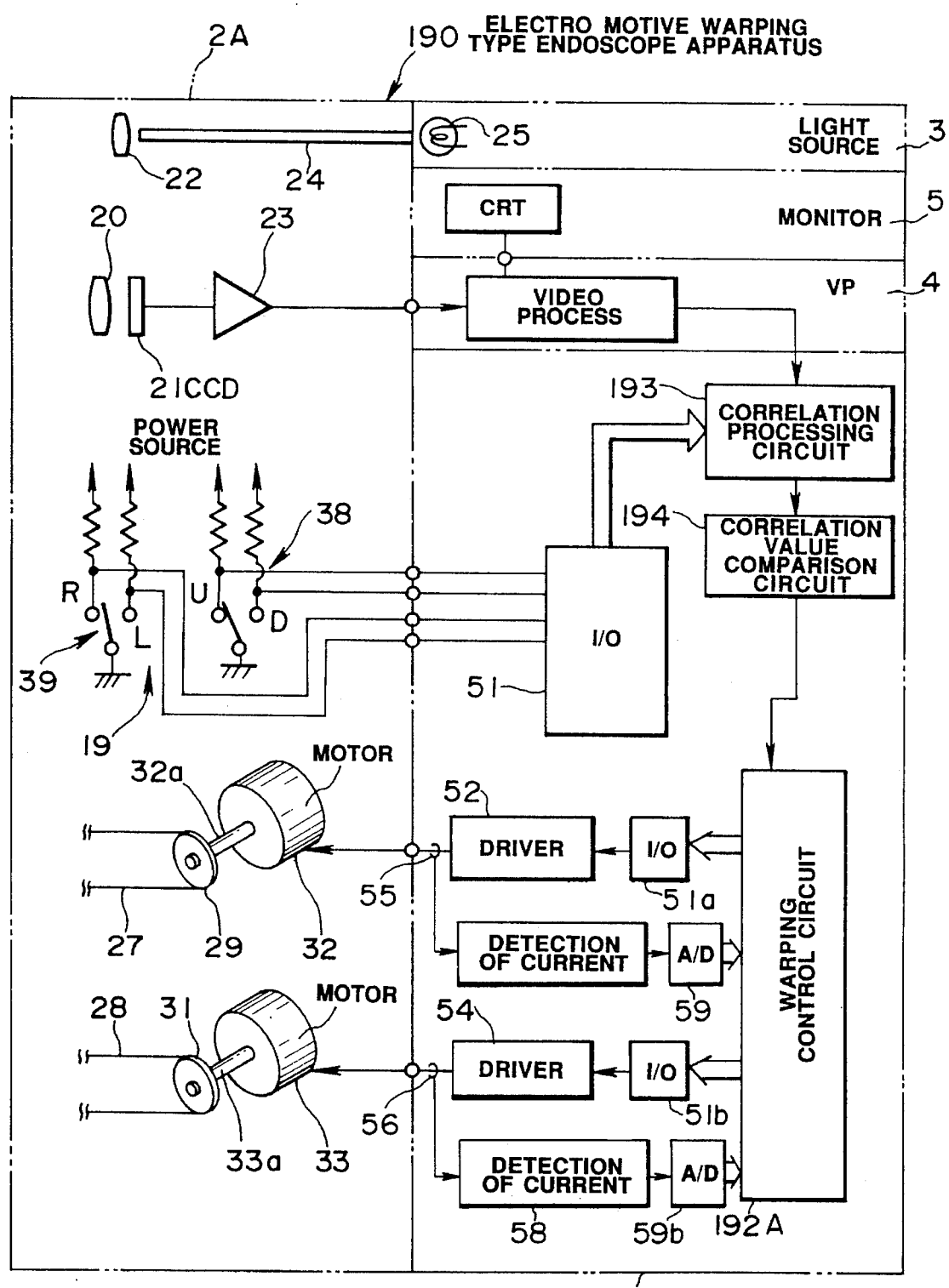
FIGS. 52 and 53 illustrate a modification to the thirteenth embodiment, where
Figure 53:
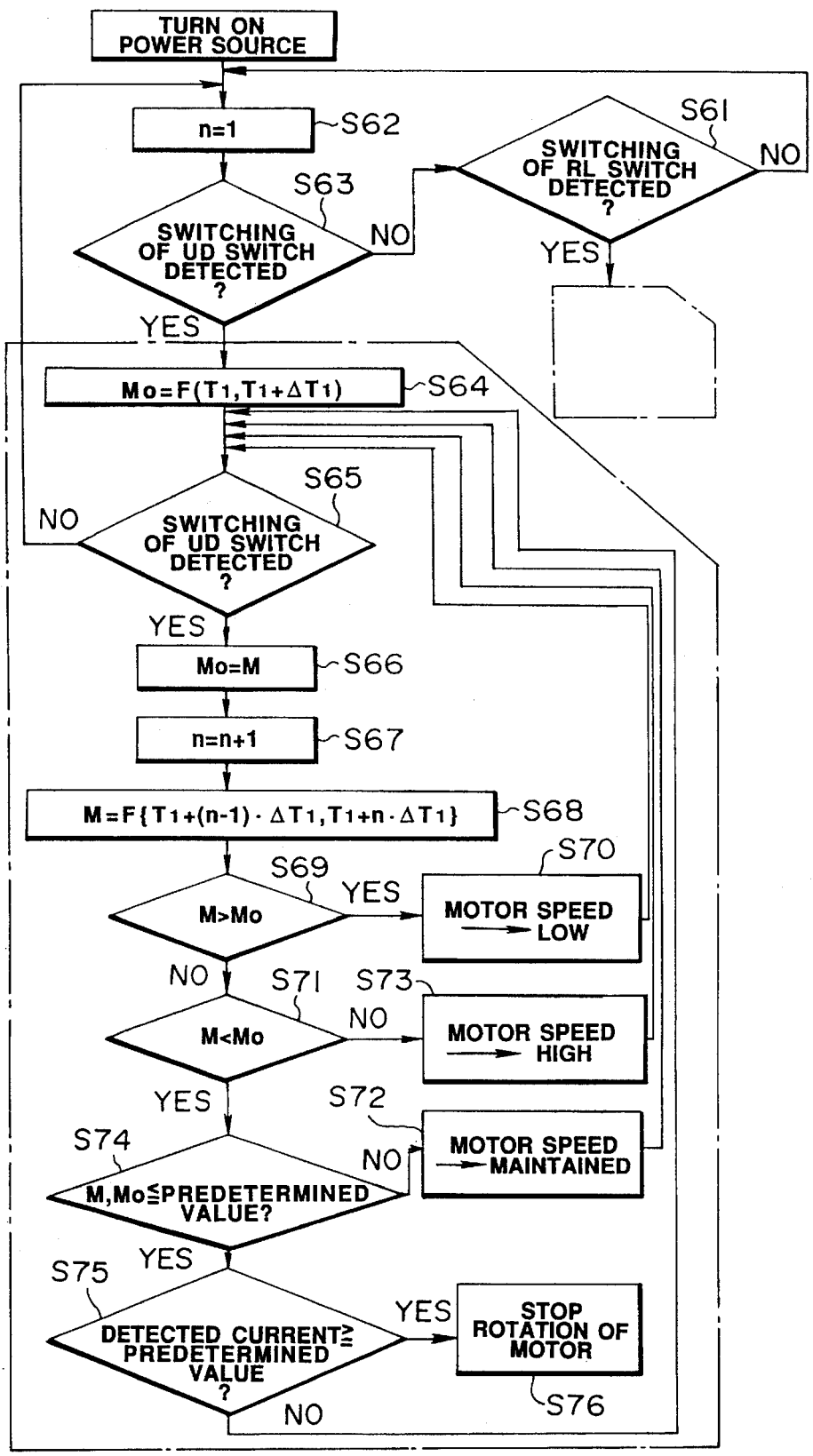

FIGS. 52 and 53 illustrate a modification of a thirteenth embodiment. FIG. 52 is a structural view which illustrates an electromotive warping type endoscope apparatus featuring an essential portion. FIG. 53 is a flow chart which illustrates control of the warping velocity.

In addition to the structure according to the thirteenth embodiment shown in FIG. 49, this modification comprises the electric current probes 55 and 56, the electric current detecting circuits 50 and 58 and the A/D converters 59a and 59b similarly to the third embodiment. The A/D converters 59a and 59b are respectively connected to a control circuit 192A. According to this modification, the warping control circuit 192A controls the velocity of the warp-enabled portion on the basis of the driving electric current value of the motor detected by the electric current detecting circuits 50 and 58 as well as having the same structure and the operation as those of the thirteenth embodiment. The same structures and operations as those or the thirteenth embodiment are given the same reference numerals and their descriptions are omitted here.

Since the flow chart shown in FIG. 53 is substantially the same as the flow chart shown in FIG. 50, the same reference numerals are given and their descriptions are omitted here. Then, description will be made about the different portions. In a case where a discrimination of YES is made in step S71 shown in FIG. 53, the control circuit 192A discriminates whether or not M and M0 are smaller than a predetermined value in step S74. If a discrimination of NO is made, the process in step S72 is performed. If a discrimination of YES is made, whether or not the aforesaid detected value of the electric current is larger than the predetermined value is discriminated in step S75. The predetermined value is set to, for example, zero with which M and M0, which are the quantity of shift in the predetermined time, are not changed considerably. If a discrimination of YES is made, the control circuit 192A stops the rotation of the motor in step S76. If a discrimination of NO is made, the flow proceeds to the process in step S65.

In addition to the effect obtainable from the thirteenth embodiment, according to this modification, a discrimination is made that the present state is a dangerous state because the insertion portion is in contact with the subject to be inspected in a case where M and M0≦a predetermined value and as well as the detected value of the electric current detecting circuit is larger than a predetermined value and the warping operation can be stopped. The warping velocity control may be performed in such a manner that a movement is made in a direction different from a direction in which the warp-enabled portion is moved or the warping velocity is decelerated. If there is a desire of elongating the time in which the comparison is made with the aforesaid predetermined value, the number of the shift quantities to be compared may be increased.

According to this modification, the operability and the safety of the warping operation can be improved. The other operations and effects are the same as those obtainable from the third and the thirteenth embodiments.

Figure 54:
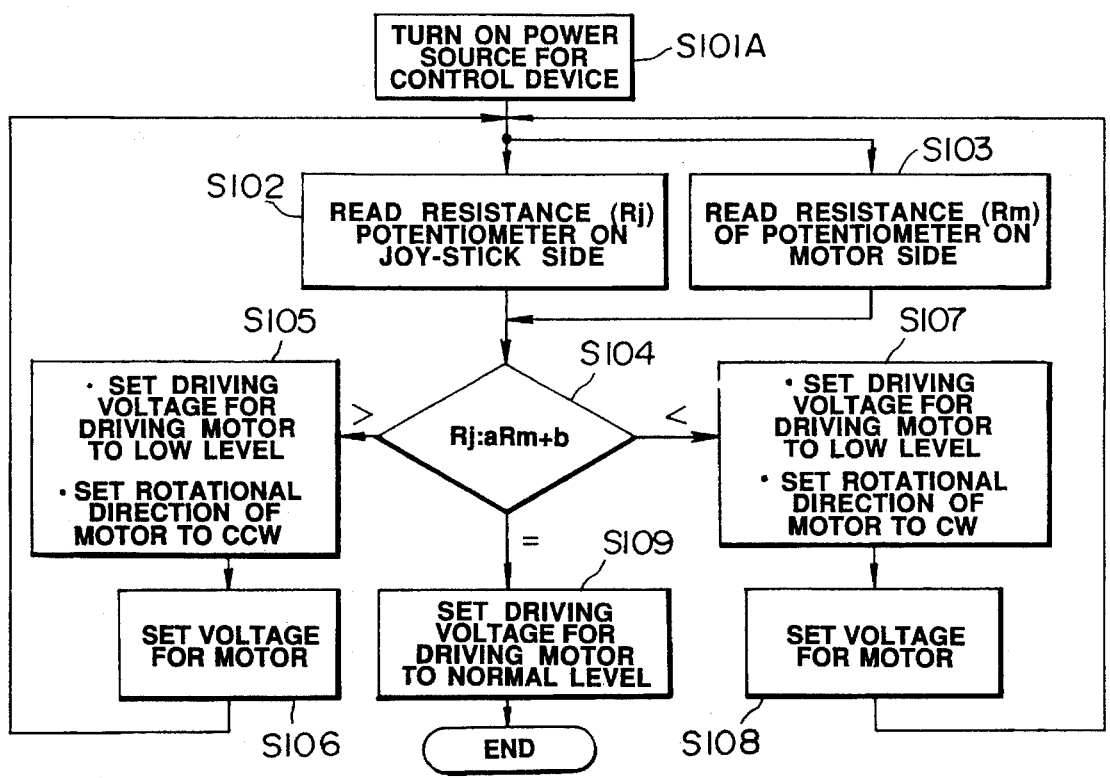
FIGS. 54 to 56 illustrate a fourteenth embodiment of the present invention, where
Figure 55:
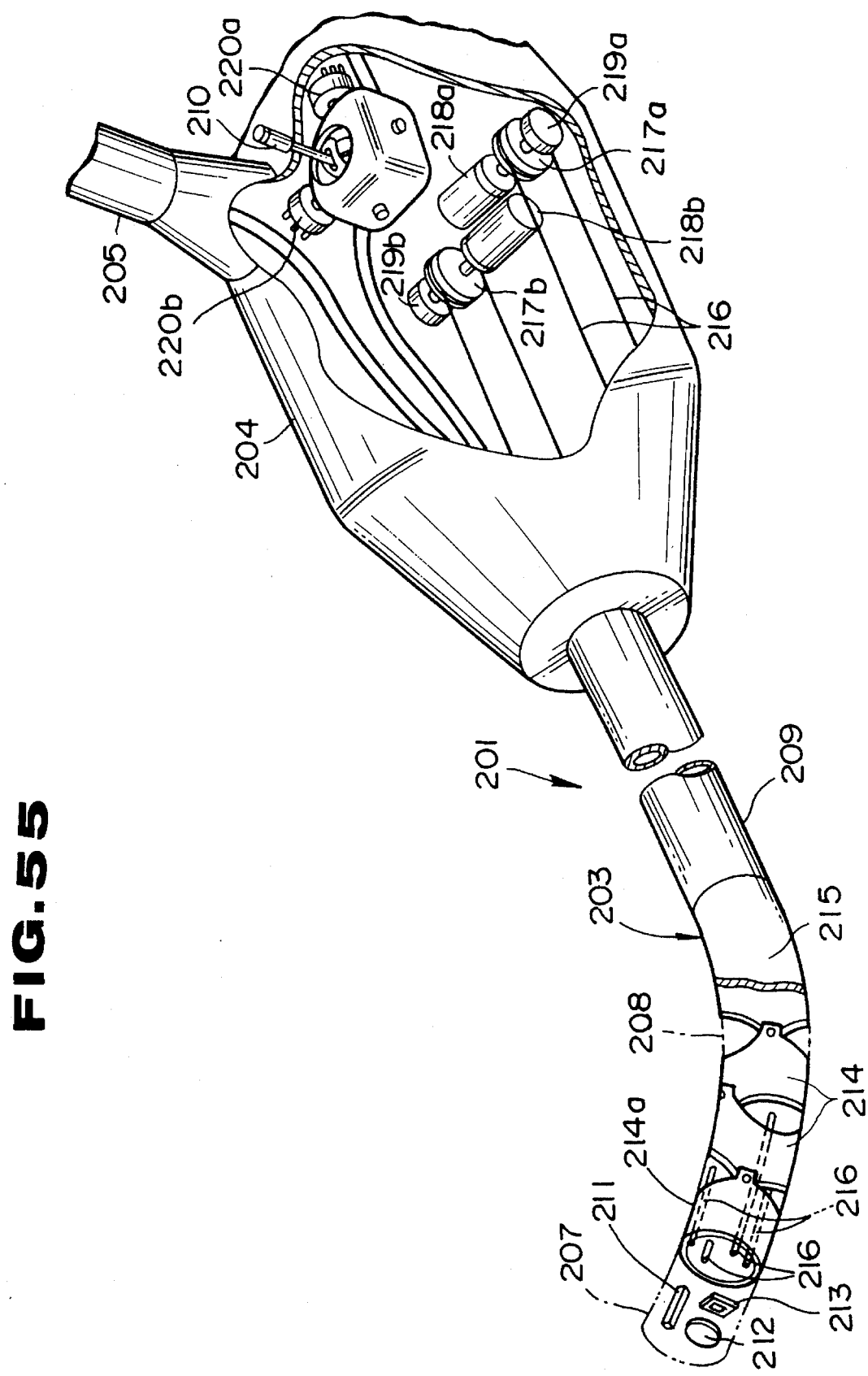
Figure 56:
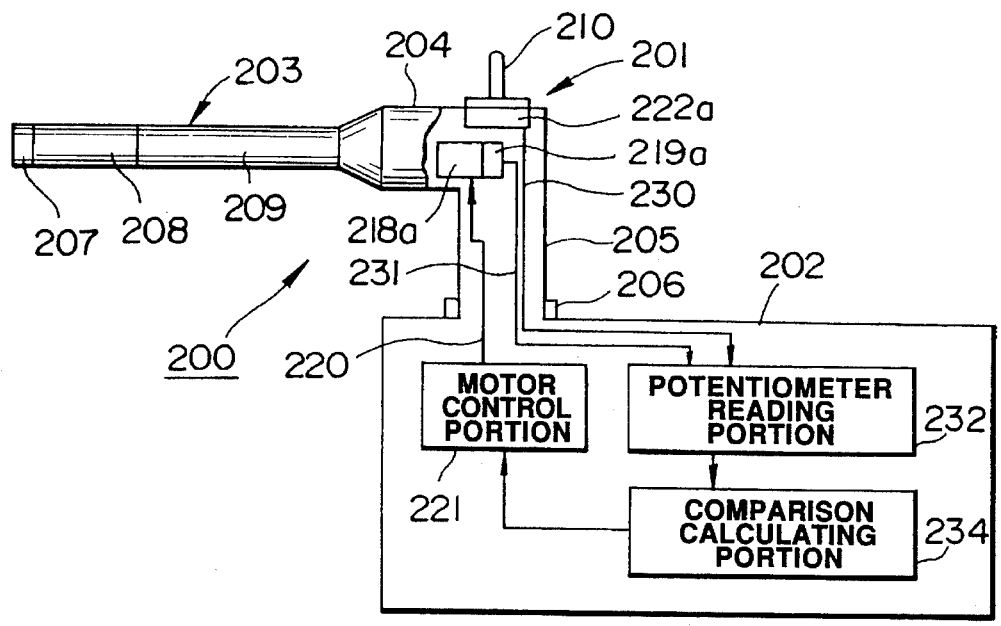

FIGS. 54 to 56 illustrate a fourteenth embodiment of the present invention. FIG. 54 is a flow chart of the control of the warping velocity. FIG. 55 is a structural view which illustrates a warping driving system and the like of the electromotive warping type endoscope apparatus. FIG. 56 is an electrical block diagram which illustrates the warping control to be performed in the electromotive warping type endoscope apparatus.

FIG. 56 illustrates an electromotive warping type endoscope apparatus 200 which is illustrated as an example and which comprises an electromotive warping type electronic endoscope 201, a motor control device 202, a light source device and a video processor and the like which are omitted from illustration.

As shown in FIG. 56, the endoscope 201 comprises an elongated and flexible insertion portion 203 and an operation portion 204 disposed adjacent to the rear end portion of the insertion portion 203. A flexible universal cord 205 extends from the side portion of the operation portion 204 and a connector 206 is disposed at the end portion of the universal cord 205. The connector 206 is connected to the motor control device 202.

The insertion portion 203 of the endoscope 201 is composed of a hard leading portion 207, a warp-enabled portion 208 which can be warped and a flexible tube 209 having flexibility when viewed from the leading portion.

An end portion of the operation portion 204 is disposed adjacent to the read end portion of the flexible tube 209. The operation portion 204 has, on the side portion thereof, a joy-stick unit 210 for enabling warping.

As shown in FIG. 55, the leading portion 207 of the endoscope 201 has an illuminating window, an observing window and a forceps channel port (omitted from illustration) at the leading portion thereof. The illuminating window has a light distribution lens (omitted from illustration). A light emission side of a light guide 211 made of a fiber bundle is disposed on the back side of the light distributing lens. The light guide 211 is inserted into the insertion portion 203, the operation portion 204 and the universal cord 205 so as to be connected to the connector 206. The light incident end of the light guide 211 is arranged to receive illuminating light emitted from a light source lamp included by the light source device.

Furthermore, an objective optical system 212 and a solid-state image sensing device 213 are disposed inside the observing window in this order when viewed from the leading portion. A signal line (omitted from illustration) is connected to the solid-state image sensing device 213, the signal line being arranged to pass through the insertion portion 203, the operation portion 204, the universal cord 205, the connector 206 and a signal cord (omitted from illustration) before it is connected to the video processor.

On the other hand, the warping portion 208 of the endoscope 01 has a warping tube formed by rotatively connecting a multiplicity of cylinder-like joint blocks 214 by using joint shafts. The warping tube is covered with a warping rubber 215. The front portion of a leading joint block 214a is connected to a leading portion 207 of the endoscope 201, while the rear end portion of the tailing joint block (omitted from illustration) is connected to the flexible tube 209.

Two pairs each of which is composed of angle wires 216 are inserted into the insertion portion 203, the front end portion of each of the angle wires 216 is connected to the leading joint block 214a. The rear end portions of the angle wires 216 of one of the two pairs are wound around a pulley 217a provided for the operation portion 204. Also the rear end portions of the angle wires 216 of the other pair are wound around another pulley 217b. The pulleys 217a and 217b are secured to rotational shafts of motors 218a and 218b secured to the operation portion 204. Motor side potentiometers 219a and 219b for detecting the rotational angle of each of the motors 218a and 218b are secured to the rotational shafts of the motors 218a and 218b.

When the motors 218a and 218b are rotated, the pulleys 217a and 217b are rotated to pull one of each of the two pairs of the angle wires 216 and as well as slackening the other angle wires 16. The motor 218a vertically warps the warp-enabled portion 208, while the motor 218b laterally warps the same. Furthermore, the warp-enabled portion 208 can be warped vertically/laterally when the joy-stick unit 210 is operated.

Two control signal lines 220 (one of them is illustrated in FIG. 56) are connected to the motors 218a and 218b. The control signal lines 220 are inserted into the universal cord 205 and the connector 206 before they are connected to a motor control portion 221 of the motor control device 202. The motors 218a and 18b are rotated by the motor control portion 221 via the control signal line.

The vertical and lateral warping joy-stick side potentiometers 222a and 222b provided for the joy-stick 210 shown in FIG. 55 are arranged in such a manner that the electric resistance value is changed according to the position of the joy-stick. Therefore, the position of the joy-stick 210 can be electrically defined. Furthermore, the motor side potentiometers 219a and 219b are arranged in such a manner that the electric resistance value is changed according to the rotational angle of each of the motor shaft. Therefore, the rotational angle of the motor shaft can be electrically defined.

Two detection signal lines 230 and 231 (one of them is illustrated in FIG. 56) are connected to the potentiometers 219a and 219b and the joy-stick side potentiometers 222a and 222b. The potentiometer 219a and 219b and the joy-stick side potentiometer 222a and 222b are electrically connected to a potentiometer reading portion 232 included in the motor control device 202 via detection signal lines 230 and 231.

The potentiometer reading portion 232 reads the electric resistance value of each of the potentiometers 219a and 219b and the joy-stick side potentiometers 222a and 222b. A comparison calculating portion 234 makes a comparison between the rotational angle of the motor supplied from the potentiometer reading portion 232 and the position of the stick so as to supply a signal corresponding to the result of the comparison to the motor control portion 221. The motor control portion 221 supplies voltage to the warping motors 218a and 218b in response to the signal supplied from the motor control portion 221 so as to rotate the motors 218a and 218b.

The rotational angle of the motor and the angle of tilt of the stick correspond to each other while holding a relationship of 1:1.

In the thus arranged structure, in a case where the endoscope 201 is used in step S101A shown in FIG. 54, a power source SW (omitted from illustration) connected to the motor control device 202 is turned on.

Then, in steps S102 and S103, the electric resistance value of each of the joy-stick side potentiometer 220a for the vertical warping, the joy-stick side potentiometer 220b for the lateral warping, the motor side potentiometer 219a for the vertical warping and the motor side potentiometer 219b for the lateral warping of the joy-stick 210 is read by the potentiometer reading portion 215.

Then, the vertical warping operation will now be described.

Assumptions are made that the electric resistance value of the joy-stick side potentiometer 220a is Rj and that of the motor side potentiometer 219a is Rm.

The fact that the rotational angle of the motor is changed according to the angle of tilt of the stick of the joy-stick means that the following relationship is held:

$$Rj = a\,Rm + b \quad (a \text{ and } b \text{ are coefficients and } a \neq 0)$$

This means that the rotation of the motor is in a proportional relationship in relation to the operation of the stick (angle of tilt). Furthermore, Rj corresponds to the angle of tilt of the joy-stick and (aRm+b) is the rotational angle of the motor, that is, the present angle of warp.

In a case where the angle of tilt of the stick (resistance value Rj) and the angle of warp (that is, resistance value Rm) are different from each other due to the operation of the stick in a state where the power supply is stopped, either Rj or (aRm+b) is larger than the other. Since the operator cannot recognize whether or not the angle of tilt of the stick and the angle of warp are different, a safe warping operation must be performed at the first warping operation after the power has been supplied. Therefore, in a case where the angle of tilt of the stick (resistance value Rj) and the angle of warp (that is, resistance value Rm) are different from each other, the motor is rotated in such a manner that they are made to be the same.

The comparison calculating portion 234 makes a comparison between resistance value Rj and resistance value (aRm+b) in step S104 on the basis of resistance value Rj and resistance value Rm read by the potentiometer reading portion 232.

If Rj≠arm+b, the comparison calculating portion 234 discriminates that the angle of tilt of the stick and the rotational angle of the motor do not coincide with each other. If Rj>aRm+b in this case, the comparison calculating portion 234 causes the motor control portion 221 to set the level of the motor driving voltage to a level lower than a normal predetermined voltage in step S105. Furthermore, it sets that the vertical warping motor 218a rotates in a direction CCW (in a direction in which the angle of tilt of the stick and the angle of warp coincide with each other). In step S106, the motor control portion 221 supplies voltage to the motor 218a.

In a case where Rj<aRm+b, the comparison calculating portion 234 similarly causes the motor control portion 221 to set the motor driving voltage to a level lower than a normal predetermined voltage in step S107. Furthermore, it sets that the vertical warping motor 218*a* rotates in the direction CW (in a direction in which the angle of tilt of the stick and the angle of warp coincide with each other). In step S108, the motor control portion 221 supplies voltage to the motor 218*a*.

In both the aforesaid cases Rj>aRm+b and Rj<arm+b, the aforesaid steps are repeated and setting of the direction, in which Rj=arm+b is held, is performed in step S109.

The supply of the voltage to the motor 218*a* and reading of Rj and Rmare continuously performed until Rj=arm+ b is held. In step S109, the motor control portion 221 sets the motor driving voltage to a normal driving level. Thus, the rotation of the motor is stopped and the sequential control operations are completed.

According to this embodiment, in a case where the angle of tilt of the stick of the joy-stick and the angle of warp are different from each other at the time of supplying power to the motor control device, the motor is rotated slowly with the voltage the level of which is lower than a normal driving level. Furthermore, automatic control is performed in such a manner that the two angles coincide with each other. Therefore, the warping operation can always be performed in a state where the two angles coincide with each other. As a result, a problem of rapid warping of the endoscope which can be easily taken place due to the difference between the two angles or another problem of unexpected movement of it can be prevented. As a result, the operability and safety of the warping operation can be improved.

Figure 57:
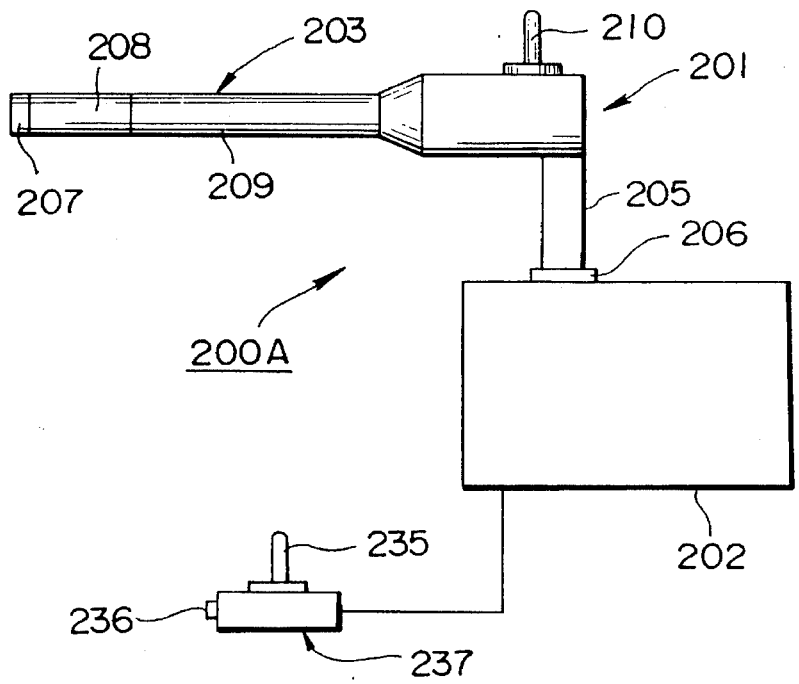
FIGS. 57 and 58 illustrate a modification to the fourteenth embodiment of the present invention, where
Figure 58:
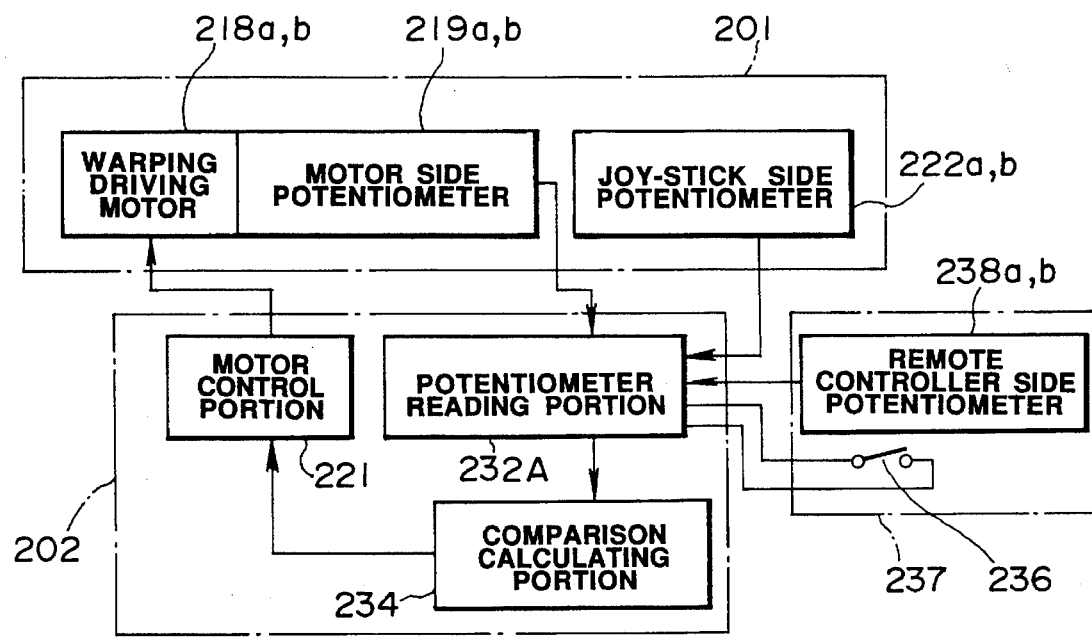

FIGS. 57 and 58 illustrate a modification of the fourteenth embodiment. In addition to the elements according to the fourteenth embodiment, this modification comprises a remote controller 237 having a warping angle controlling joy-stick 235 and an endoscope/remote-controller-joy-stick switch SW 236. The same structures and operations as those according to the fourteenth embodiment are given the same reference numerals and their descriptions are omitted here.

The remote controller 220 is connected to the motor control device 202. The warping angle controlling joy-stick 235 is structured similarly to the aforesaid joy-stick 210 and having potentiometers 238*a* and 238*b*.

As shown in FIG. 58, the motor side potentiometer 219*a* and 219*b*, the joy-stick side potentiometers 238*a* and 238*b* and the remote control side potentiometers 238*a* and 238*b* to a potentiometer reading portion 232A of the motor control device 202. The potentiometer reading portion 232A performing reading the joy-stick side potentiometer or the remote controller side potentiometer according to switching on/off of the endoscope/remote controller-joy-stick SW 236. That is, when the endoscope/remote controller-joy-stick SW 236 is switched on, the control of the warping motor is switched from the endoscope side joy-stick 210 to the joy-stick 235 of the remote controller 237.

According to this embodiment, the endoscope/remote controller-joy-stick SW 236 is switched on in place of switching on the power source switch of the motor control device 202 in step S101A shown in FIG. 54. The ensuing sequential control operations are performed similarly and their descriptions are omitted here.

Since the other structures, the operations and effects are the same as those according to the fourteenth embodiment, their descriptions are omitted here.

When the endoscope is connected to the motor control device which is turned on, the same control may be performed at the time of switching a state in which the warping operation is automatically controlled by the control device to manual control.

Figure 59:
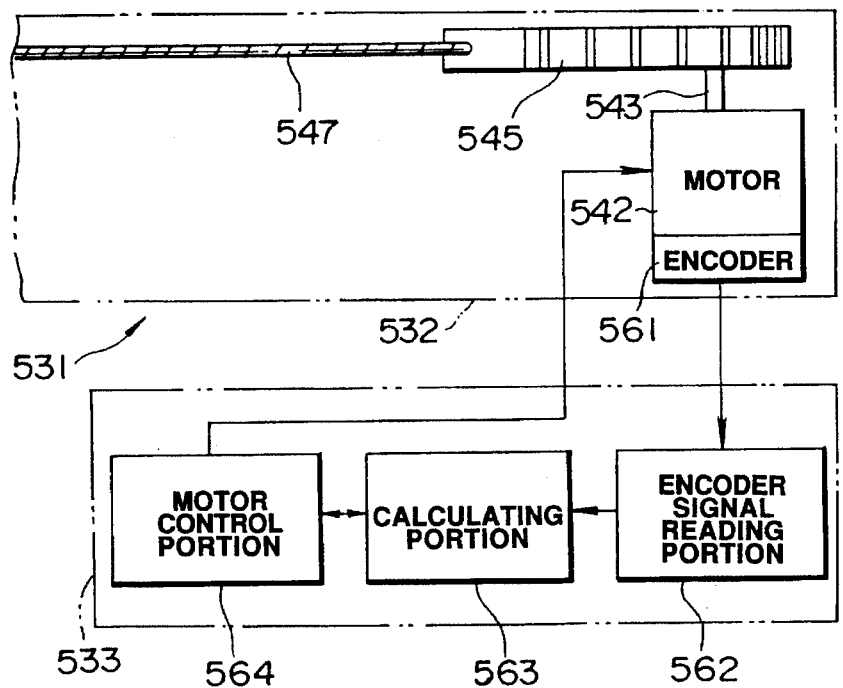
Figure 60:
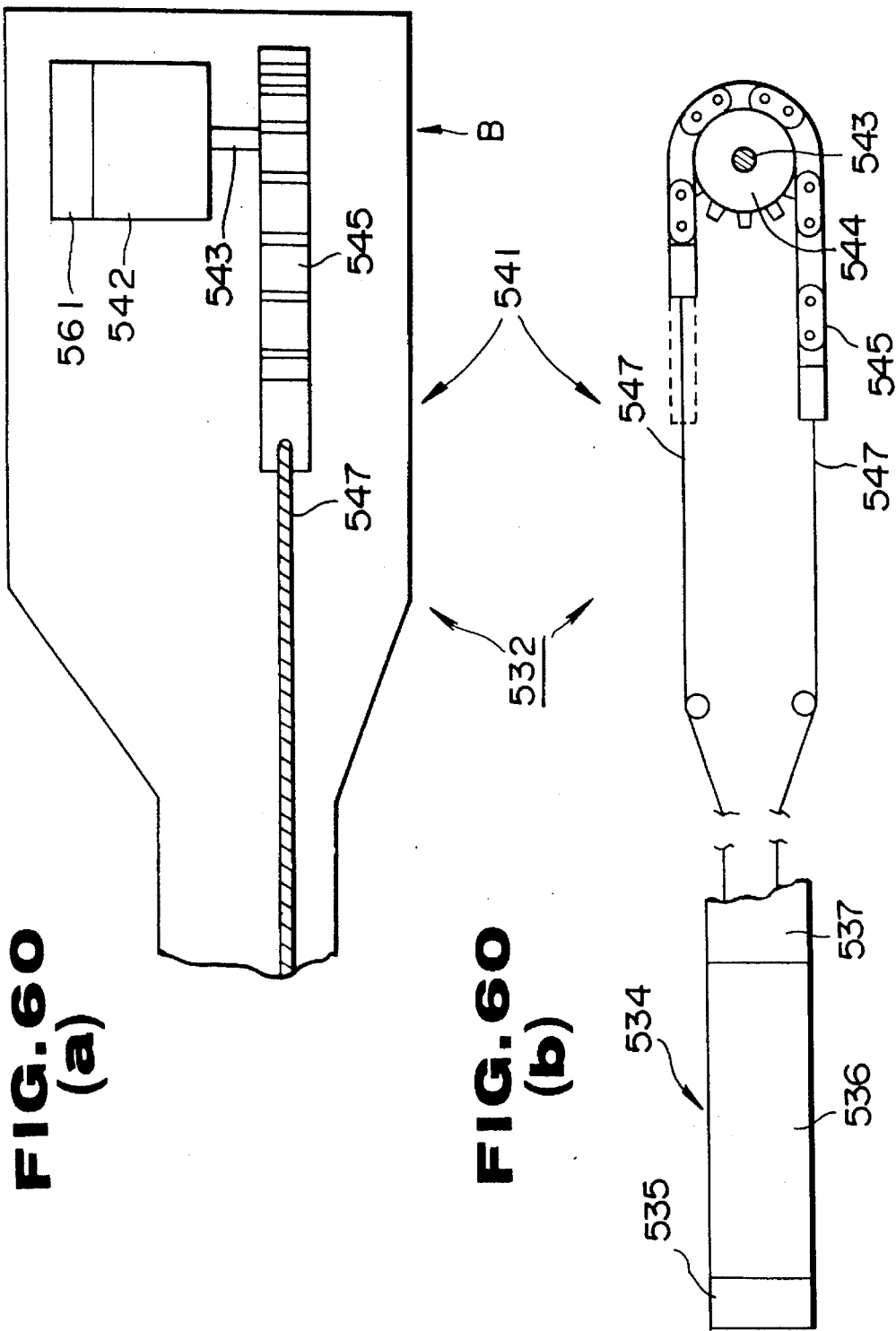
FIG. 60 is a structural view which illustrates a portion of the warping mechanism of the endoscope.

FIGS. 59, 60(*a*) and 60(*b*) illustrate a fifteenth embodiment of the present invention. FIG. 59 is a schematic structural view which illustrates a warping mechanism of the endoscope apparatus and an electric circuit of the control system. FIGS. 60(*a*) and 60(*b*) show a structural view which illustrates a portion of the warping mechanism of the endoscope.

An electromotive warping type endoscope 531 shown in FIG. 59 comprises an electromotive warping type electronic endoscope 532, a motor control device 533, a light source device, a video processor and a monitor (omitted from illustration).

The video processor and the light source device are the same as those according to the third embodiment and the motor control device 533 rotates a motor to be described later according to the operation of a warping operation switch (omitted from illustration) so as to realize a predetermined state of warp.

FIG. 60(*a*) is a cross-sectional view which illustrates an operation portion 541 of the endoscope 532. FIG. 60(*b*) illustrates a portion of the warping mechanism in such a manner that an insertion portion 534 of the endoscope 532 and the operation portion are illustrated in a cut-away drawing.

The insertion portion 534 of the endoscope 532 comprises a leading portion 535, a warp-enabled portion 536 which can be warped and a soft portion 537 in this sequential order when viewed from the leading portion. The soft portion 537 is connected to the operation portion 541.

The operation portion 541 includes a warping motor 542, a motor shaft 543 extending from the warping motor 542, a sprocket 544 secured to the motor shaft 543 and a chain wound around the sprocket 544. The warping motor 542 is controlled by the motor control device 533. Furthermore, an encoder 561 is provided coaxially with the warping motor 542.

End portions of wires 547 are connected to the two end portions of the chain 545, the wires 547 being inserted into the operation portion 541 and the soft portion 537. The other end portions of the wires 547 are secured to the leading operation block of the warp-enabled portion 536. By pulling the wires 547, the warp-enabled portion 536 can be warped.

The motor control device 533 comprises an encoder signal reading portion 562 for reading a signal transmitted from the encoder 561, a calculating portion 563 for calculating the rotational angle of the motor 542 in response to the signal read by the encoder signal reading portion 562 and a motor control portion 564 for controlling the motor 542 according to the result of the calculation performed by the calculating portion 563.

In the thus arranged structure, when the warping motor 542 is rotated, the encoder 561 disposed coaxially with the motor 542 detects a signal which corresponds to the rotational angle. The signal detected by the encoder 561 is supplied to the calculating portion 563 via the encoder signal reading portion 562 included by the motor control device 564, so that the rotational angle is calculated by the calculating portion 563.

In a case where the rotational angle is made at which the warp-enabled portion 536 becomes straight, the motor control portion 561 stops the supply of the voltage to the motor 542 for a predetermined time, for example, several seconds. Therefore, also the warp-enabled portion 536 is stopped for the same time period.

As a result, the operator is able to recognize that the warp-enabled portion 536 is straight depending upon the observation that the display of the endoscope is stopped for the aforesaid time although warping is made.

According to this embodiment, by simply observing the normal endoscope image, the operator is able to recognize the straight state of the warp-enabled portion 536 according to the velocity change of the scope of the monitor, that is, the stoppage. Therefore, the fact that the warp-enabled portion has become straight can be reliably recognized and therefore the warping operation can be performed while recognizing the state of the warp-enabled portion as compared with a conventional apparatus with which the state of the warp-enabled portion cannot easily be recognized. That is, according to this embodiment, the operability and the safety of the warping operation can be improved.

This embodiment may be arranged in such a manner that the electronic endoscope is replaced by an optical fiber endoscope.

Figure 61:
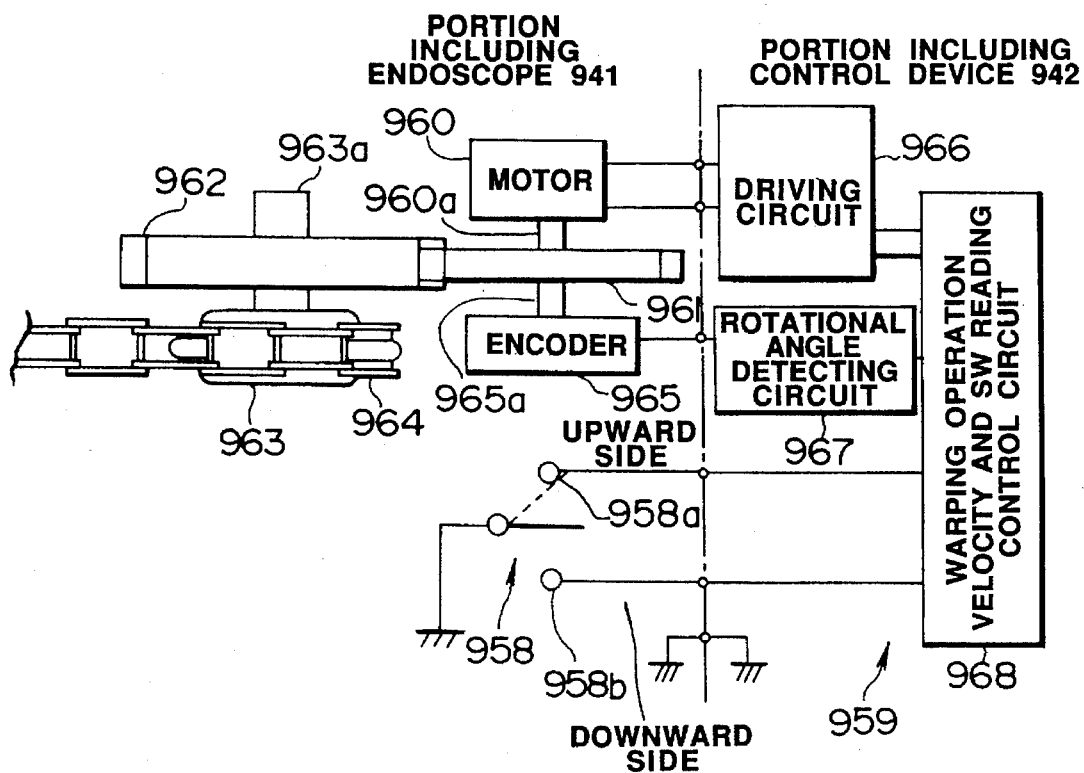
FIGS. 61 to 69 illustrate a sixteenth embodiment, where
Figure 62:
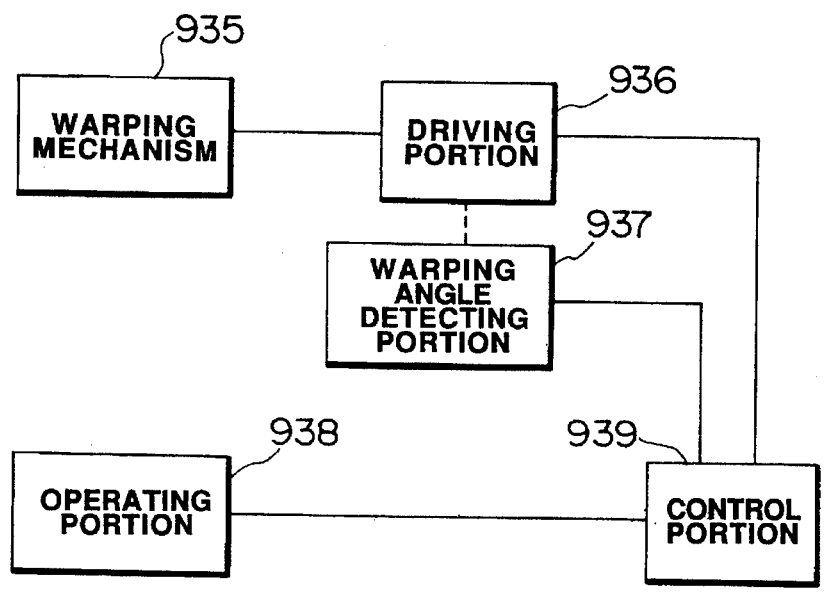
Figure 63:
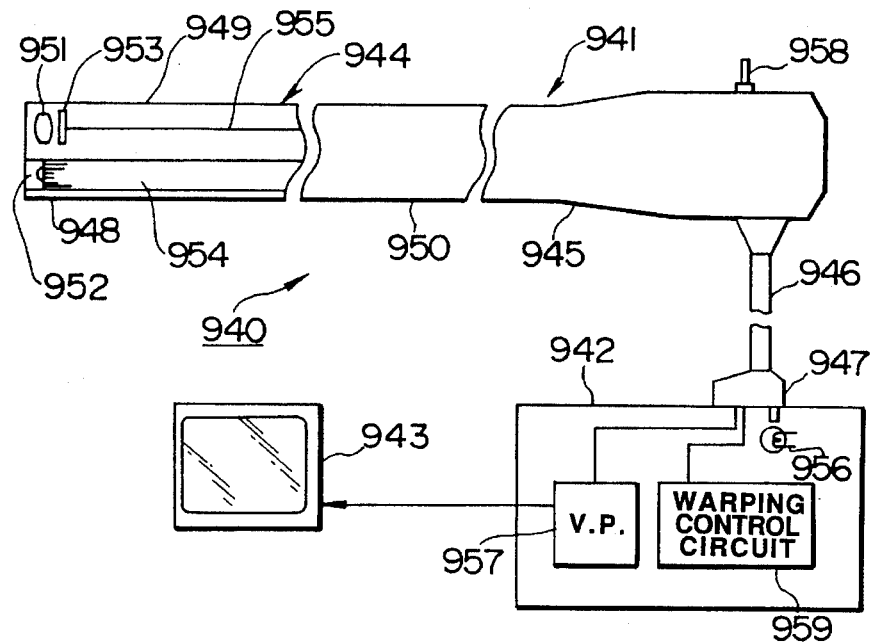
Figure 64:
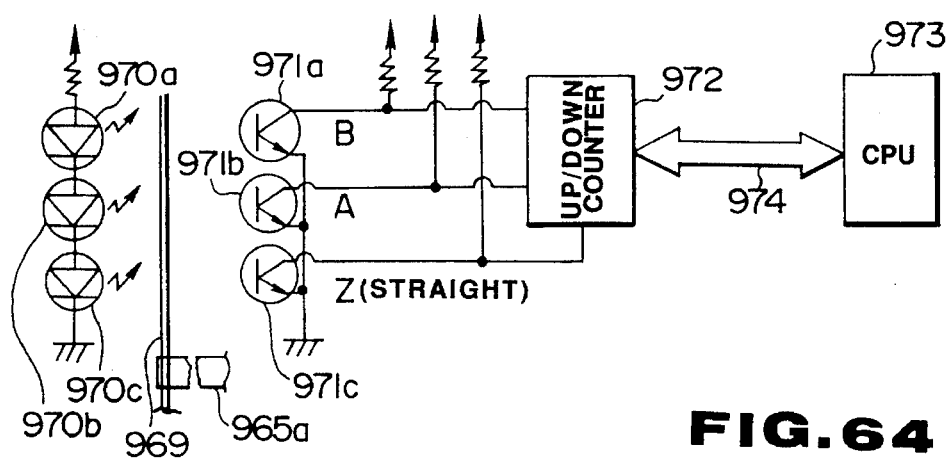
Figure 64:
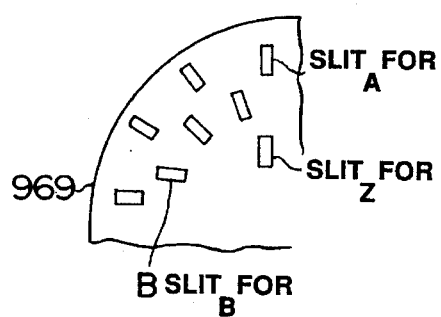
Figure 65:
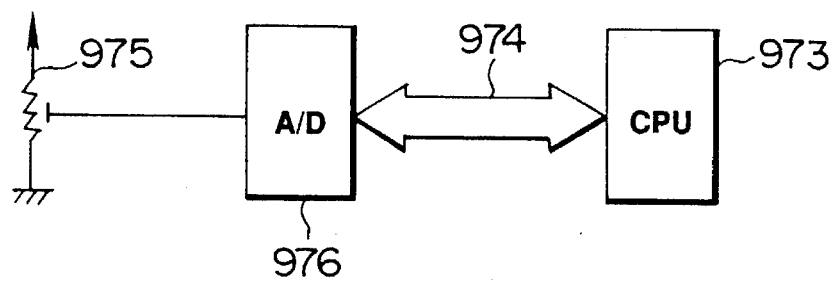
Figure 66:
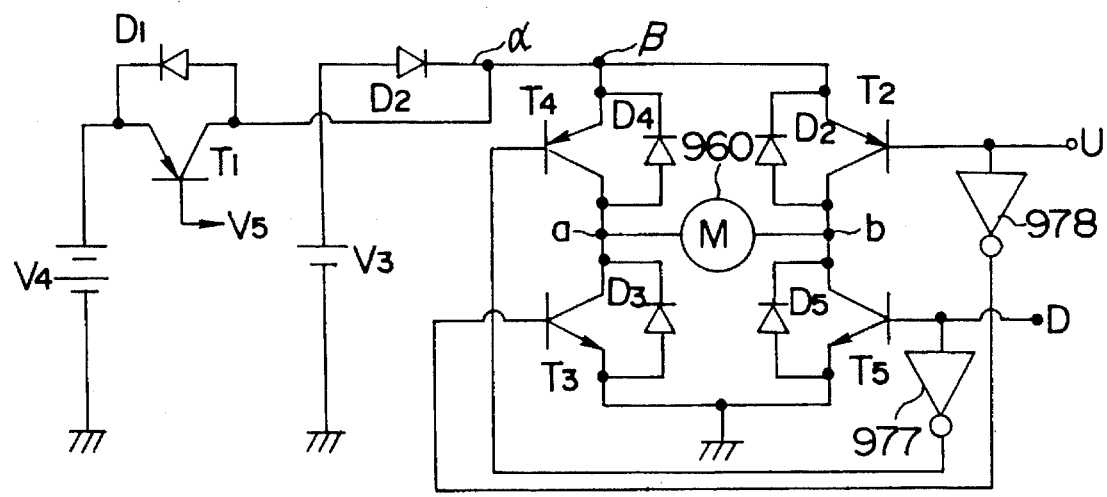
Figures 67, 68:
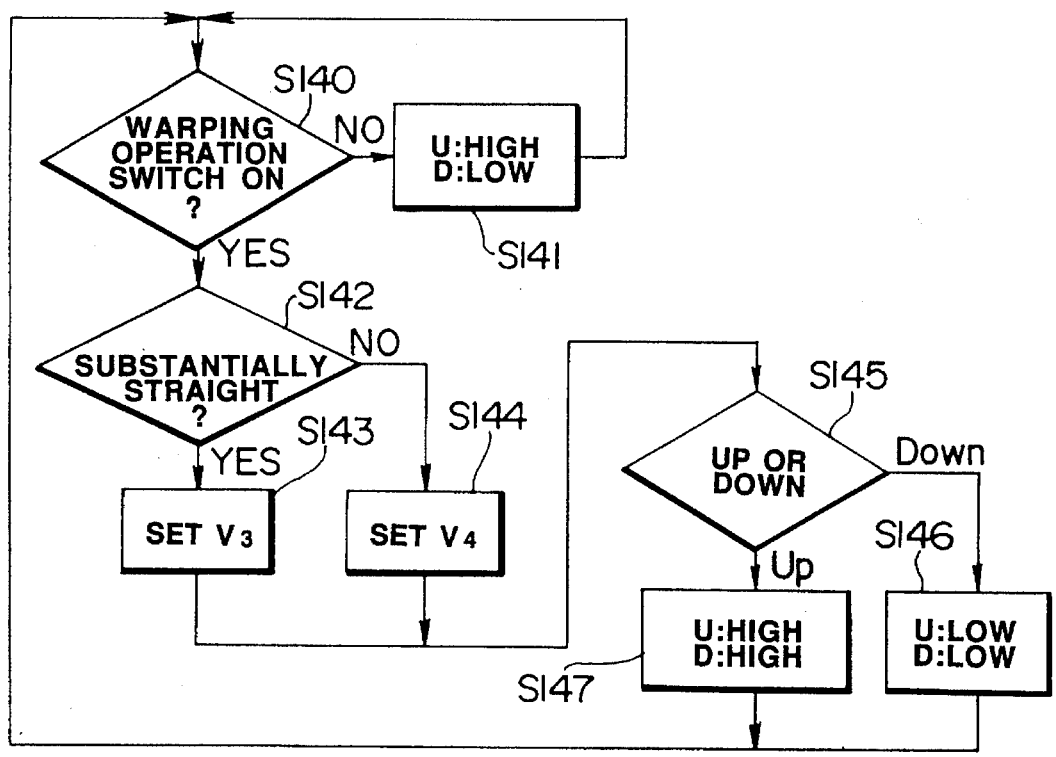
Figure 69:
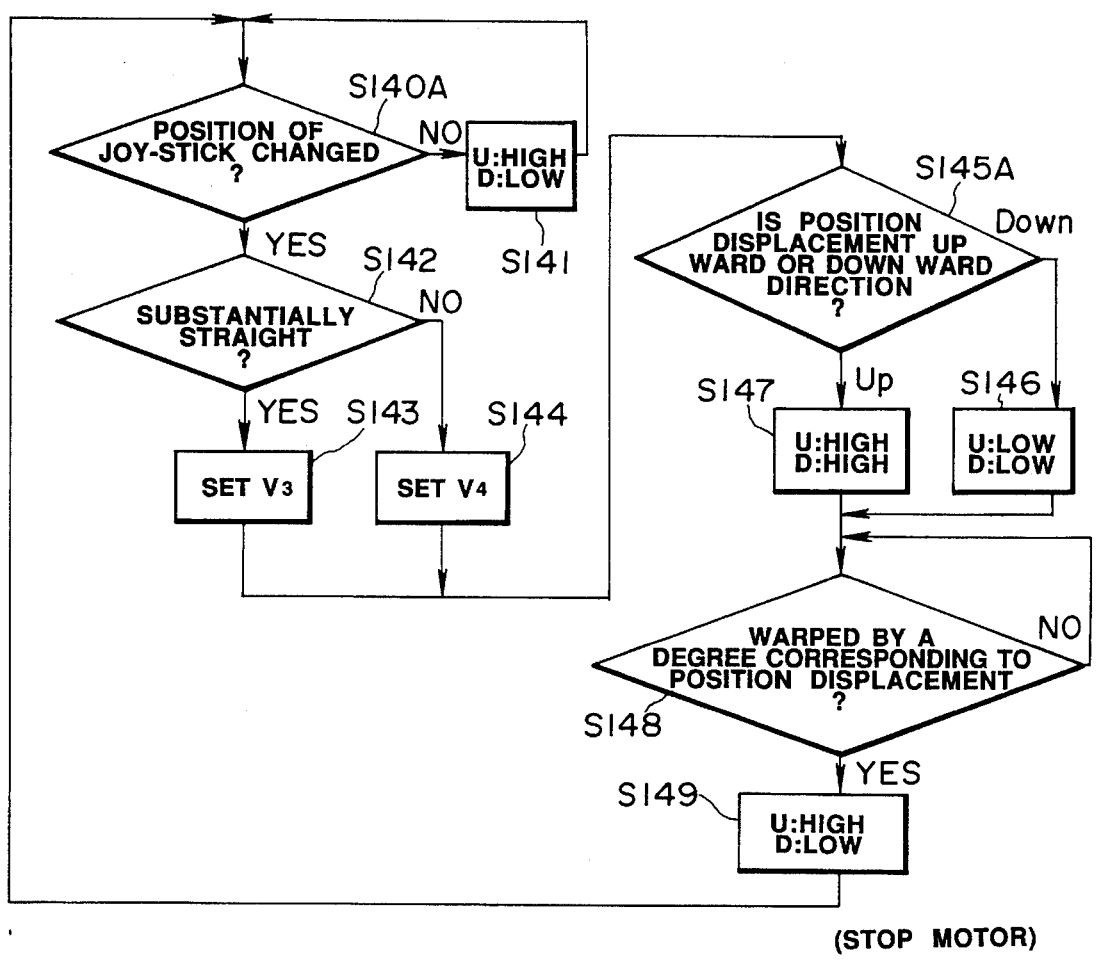

FIGS. 61 to 69 illustrate a sixteenth embodiment. FIG. 61 is a block diagram which illustrates an electromotive warping type endoscope apparatus according to the sixteenth embodiment featuring an essential portion. FIG. 62 is a schematic block diagram which illustrates the electromotive warping type endoscope apparatus according to the sixteenth embodiment. FIG. 63 is a schematic view which illustrates the overall structure of the electromotive warping type endoscope apparatus. FIG. 64(*a*) is a specific structural view which illustrates an example of detecting the angle of the warp and the rotation. FIG. 64(*b*) is a structural view which illustrates a slit plate of an encoder. FIG. 65 is a structural view which illustrates another example of detecting the warping angle. FIG. 66 is a specific structural view which illustrates a drive circuit. FIG. 67 is a truth value table of the circuit shown in FIG. 66. FIG. 68 is a flow chart which illustrates an example of an operation of controlling switch of the warping velocity. FIG. 69 is a flow chart which illustrates another example of the operation of controlling the switch of the warping velocity.

The electromotive warping type endoscope apparatus according to the sixteenth embodiment will be schematically illustrated with reference to a schematic view shown in FIG. 62.

The endoscope apparatus according to this embodiment comprises a warping mechanism 935, a driving portion 946 for warping the warp-enabled portion of the endoscope by means of the warping mechanism 935, a warping angle detecting portion 937 disposed in the driving portion 936 and detecting the warping angle, an operation portion 938 for instructing the warping operation and a control portion 939 for controlling the driving portion 936 in response to the control instruction issued through the operation portion 938.

As assumption is made that an upward warping is instructed by the operation portion 938. The control portion 938 reads the instruction as a signal and instructs the driving portion 936 to perform upward driving (for example, the rotation of the included motor). Since the warping mechanism 935 is connected to the driving portion 936, the leading portion of the endoscope is warped upward.

The quantity of warp of the warp-enabled portion of the endoscope is detected by the warping angle detecting portion 937 and it is supplied to the control portion 939. The control portion 939 supervises the detection signal denoting the warping angle and supplies a control signal to the driving portion 936 to perform a low velocity warping operation (for example, to perform driving with a lower voltage level in a case of a voltage control system) in a case where the straight-like state (for example, in a range of ±10°) is realized. After the leading portion of the endoscope has passed through the portion adjacent to the straight portion, control is performed to cause the normal velocity operation (the voltage is raised to the original level).

As shown in FIG. 63, the electromotive warping type endoscope apparatus 940 comprises an endoscope 941, a control device to which the endoscope 941 is connected and a monitor 943 connected to the control device 942.

The endoscope 941 comprises an elongated insertion portion 944, an operation portion 945 connected to the rear end portio of the insertion portion 944 and a universal cord 946 extending from the side portion of the operation portion 945. A connector 947 detachably connected to the control device 942 is disposed at the end portion of the universal cord 946. The insertion portion 944 comprises a hard leading portions 948, a warp-enabled portion 949 for warping the leading portion 948 into a desired direction and a relatively hard flexible tube portion 950 disposed in this sequential order when viewed from the leading portion. The flexible tube portion 950 is connected to the operation portion 945.

The leading portion 948 of the insertion portion 944 has an objective lens 951 and a light distributing lens 952 disposed thereto. Furthermore, a solid-state image sensing device 953 such as a CCD is disposed at the image forming position of the objective lens 951. In addition, a light emission end of a light guide 954 is disposed at the rear end portion of the light distributing lens 952. A signal line 955 connected to the solid-state image sensing device 953 and the light guide fiber 954 pass through the insertion portion 944, the operation portion 945 and the universal cord 946 before they are connected to the connector 947.

The control device 942 includes a light source 956 for supply illuminating light to the light incident end of the light guide fiber 954 and a video processor 957 connected to the solid-state image sensing device 953 via the signal line 955 and the connector 947. The solid-state image sensing device 953 is operated by the video processor 957. An output signal transmitted from the solid-state image sensing device 953 is processed to be a video signal by the video processor 957 so as to be supplied to the monitor 943. As a result, an image of a subject is displayed on the scope of the monitor 943. Furthermore, a warping operation switch 958 for instructing warping is disposed in the operation portion 945.

The control device 942 includes a warp control circuit 959 for controlling the electromotive warping type endoscope 941.

FIG. 61 illustrates an electrical connection established between the electromotive warping type endoscope 941 and the warp control circuit 959 and a portion of the warping mechanism. The operation portion 945 of the electromotive warping type endoscope 941 includes, for example, a DC motor 960 servicing as a driving portion for warping the warp-enabled portion 949. A rotational shaft 960*a* of the motor 960 has a drive gear 961 secured to an intermediate portion thereof.

A shaft 963*a* of a sprocket 963 is secured to a driven gear 962 engaged with the driver gear 961. A chain 964 is rotatively fastened to the sprocket 963. End portions of two wires (omitted for illustration) are connected to the chain 964 by connection members (omitted from illustration).

The other end portions of the two wires are inserted into a plurality of joint blocks omitted from illustration disposed in the warp-enabled portion 949 and rotatively combined to each other. Each of the wires is secured to the front joint block. The other end portions of the wires are secured to the leading portion 948, so that the wires are pulled/slackened when the Q motor 960 is rotated. As a result, the warp-enabled portion 949 can be warped. Furthermore, an encoder 965 for detecting the rotational angle of the motor 960 is disposed at a position adjacent to the leading portion of the rotational shaft 965*a* of the motor 960.

The warp control circuit 959 comprises a drive circuit 966 for driving the motor 960, a rotational angle detecting circuit 967 for converting an output signal transmitted from the encoder 965 so as to transmit it and a warping operation/velocity/SW reading control circuit (hereinafter called a "control circuit") 968 for controlling the warping operation and the warping velocity and reading the state of the warping operation switch 958.

The control circuit 968 is made of, for example, a CPU so as to control the direction and the speed of rotation of the motor 960 according to the state of the warping operation switch 958.

The operation of this embodiment will now be described with reference to FIG. 61.

Assuming that the warping operation switch 958 is operated and its contact 958a is brought to a GND level. The aforesaid state is identified by the control circuit 968 by, for example, a method in which it is read by a CPU via an I/O port (omitted from illustration). Assuming that it is an operation of instructing an upward warping, the control circuit 968 reads the present position of the leading portion 952 from the rotational angle detecting circuit 967 so as to confirm whether or not the present position is near the straight portion. In a case where the present position is near the straight portion, the control circuit 968 issues a driving velocity instruction to set a low voltage level and also instructs the drive circuit 966 to perform an upward directional operation. When the driving velocity and the direction are instructed, the drive circuit 966 supplies driving voltage V3 to the motor 960, so that the upward directional warping operation is commenced. When the warping angle of the warp-enabled portion 949 becomes enlarged, the fact that the position has deviated from the positions near the straight portion is detected by the rotational angle detecting circuit 967 in response to the position signal of the encoder 965. Then, the control circuit 968 instructs to change setting to a high voltage as the driving velocity instruction.

In a case where the position of the leading portion 948 is not near the straight portion at the time of starting instructing the warping operation, the driving velocity instruction is made with a high voltage level. If the warping operation switch 958 is connected to a contact 958b, the warping direction becomes the downward direction. Although illustration is omitted here, the operation in the R/L (right/left) direction is similarly performed.

According to this embodiment, since the warping velocity is lowered at the positions adjacent to the straight portion and therefore the image moving velocity is lowered on the display scope, the straight position can be confirmed. That is, by simply observing the scope of the monitor on which the image of the endoscope is displayed, the straight state, which is the basic position at the time of the insertion, can be detected. Therefore, the necessity of observing the other display (or example, a sub-scope or a display panel of the control device) can be eliminated and therefore the operability can be improved.

FIG. 64(a) illustrates an example of the rotational angle detecting circuit 967.

As shown in FIG. 64(a), a slit plate 969 is rotatively held by the encoder shaft 965a secured to the motor shaft 960a (the case of the encoder 965 is omitted from illustration). LEDs (Light Emitting Diodes) 970a, 970b and 970c connected in series to the power source while including a resistor as always turned on. Furthermore, phototransistors 971a, 971b and 971c are disposed at positions to face the LEDs 970a, 970b and 970c while interposing the slit plate 969. The slit plate 969 has a plurality of slits as shown in FIG. 64(b). A slit for Z is formed at the innermost portion of the slit plate 969, the slit for Z being formed at the straight position of the leading portion 948. Furthermore, a plurality of slits for A and those for B are formed one round at predetermined intervals outer than the aforesaid innermost portion and the outermost portion, respectively. The slits for A and B are alternately formed in the circumferential direction so as to detect pulses the phase of which are deviated from each other by 180°.

Light emitted from each of the LEDs (Light Emitting Diodes) 970a, 970b and 970c passes through the slits for A, B and C so as to be received by the phototransistors 971a, 971b and 971c. As a result, pulse signals for A, B and Z are generated.

The emitter of each of the phototransistors 971a, 971b and 971c is grounded, while the collector for the same is connected to an up/down counter 972 of the rotational angle detecting circuit 967 and it is pulled up via a resistor. In the rotational angle detecting circuit 967, the up/down counter 972 and a CPU 973 are connected to each other via bus line 974.

When the motor shaft 960a is rotated, the slit plate 969 is rotated. When the slit of the slit plate 34 reaches the straight position, the phototransistor 971c is operated, causing an input to the up/down counter 972 is made. The pulse signals for A, B and Z obtained after they have passed through the slits for A, B and Z respectively are an advance signal, a delay signal and a zero (straight position) signal as an ordinary encoder. The structure is arranged in such a manner that a signal for Z is generated when the endoscope leading portion 948 is in a straight state. This signal brings the up/down counter 972 into a clear state.

The up/down counter 972 increases the count value in the upward direction, while it decreases the same in the downward direction. The count value is read by the CPU 973 via the bus line (an address bus or a data bus). The operation performed by the CPU 973 may be performed by the CPU of the control circuit 968.

FIG. 66 illustrates an example of the drive circuit 966.

In order to simplify description, only the vertical directional warping operation will now be described, while omitting the lateral directional warping operation here.

An H-bridge circuit is connected to the two end portions of the motor 960 shown in FIG. 66, the H-bridge circuit being composed of PNP-type transistors T2 and T4 and NPN-type transistors T3 and T5. An up-side contact 958a and a down-side contact 958b are connected to the base of each of the transistors T2 and T5. On the other hand, the output from an inverter 977 is connected to the base of the transistor T4. The output from an inverter 978 is connected to the base of the transistor T3. The down-side contact 958b (hereinafter called the "D terminal") and the up-side contact 958a (hereinafter called the "U terminal") are connected to the inputs of the inverters 977 and 978.

The collectors of the transistors T2 and T5 are connected to the two end portions of the motor 960, while each emitter is grounded.

The emitters of the transistors T2 and T4 are connected to a power source V3 via a diode D6 and they are also connected to the collector of the PNP-type transistor T1. The base of the transistor T1 is connected to a power source V5 and the emitter of the same is connected to a power source V4.

Diodes D1 to D5 are connected to the transistors T1 to T5 in parallel to the collectors and the emitters. The voltage level V4 and the voltage V3 hold a relationship V4 > V3.

Then, the operation according to this embodiment will now be described with-reference to the flow chart shown in FIG. 68.

First, in step S140, the control circuit 968 supervises whether or not the warping operation switch 958 is switched on. If a discrimination of NO is made, the level of the signal of the U terminal is high and that of the signal of the D terminal is low. Therefore, the motor 960 is stopped and the warp-enabled portion 948 is in a stationary state. In this state, all of the transistors T2 to T5 are turned off (refer to truth value table shown in FIG. 67).

If a discrimination of YES is made, the control circuit 968 discriminates whether or not the position is near the straight portion in response to a detection signal supplied by the warping angle detecting circuit 967.

In the case where the position is near the straight portion (YES), the transistor T1 is turned off. In cases where the transistor T1 is turned off, the voltage to be supplied to the motor 960 becomes V3 if the voltage drop at the diode D1 is neglected.

Then, in step S145, the control circuit 968 discriminates whether or not the setting of the warping operation switch 958 is made to an upward direction or a downward direction. In a case where the setting to the downward direction is made, the signal level of the D terminal of the warping operation switch 958 is low and that of the U terminal is low. Therefore, the transistors T2 and T3 are turned on, while the transistors T4 and T5 are turned off. As a result, an electric current passes through the motor 960 in a direction from b to a when viewed in the drawing, causing a downward rotation is made at a velocity in proportion to voltage level V3. The warp-enabled portion 949 is warped in the downward direction.

On the other hand, if a discrimination of "UP" is made in step S147, the signal level at each of the U and D terminals becomes different (that of each of them is high) from the aforesaid case. Therefore, the motor 960 is rotated in an upward direction in contrast to the aforesaid case. At this time, the transistors T2 and T3 are turned off, while the transistors T4 and T5 are turned on. As a result, an electric current passes through the motor 960 in a direction from a to b when viewed in the drawing.

If a discrimination is made in step S142 that the position is not near the straight portion (NO), the transistor T1 is turned on in step S144 and therefore voltage V4 is applied. Since voltage level V4 is higher than voltage level V3, the rotation speed of the motor is raised. The control of switching the rotation speed may be performed by controlling the signal level at the terminal V5 by the control circuit 968. Although the operations in steps S145 to S147 are performed similarly to the case in which voltage level V3 is applied, the warping velocity becomes higher by a degree corresponding to the voltage which is higher than voltage level V3.

As described above, when the constant voltage level V3 and V4 are switched to rotate the motor 960, causing the leading portion 948 to reach the position near the straight portion. In this case, the warping velocity is lowered. On the other hand, when the angle of warp becomes large since the position has been moved away from the straight portion, the warping velocity is raised. As a result, the velocity of moving the scope is lowered on the image, so that whether or not the position has reached the position near the straight portion can be confirmed. That is, the straight (or the straight-like) state, which is the basic state, can be discriminated from the display on the scope. As a result, the operator is able to recognize the state of the leading portion of the insertion portion. Therefore, according to this embodiment, the operability of the warping operation can be improved.

If the load is increased due to contact with the colon or the like, the value of the electric current increases or the warping velocity is lowered. It leads to a fact that the scope moving velocity is lowered on the image and therefore the increase in the load of the warping operation can be confirmed on the image.

As shown in FIG. 66, a resistor for detecting the driving current is inserted in series into a portion between $\alpha$ and $\beta$ so as to detect the value of the passing electric current according to the generated voltage. A structure may be arranged in such a manner that, if an electric current larger than a predetermined value which corresponds to V3 and V4 has passed, the transistors (T1 to T5) are turned off. If the structure is arranged as described above, the warping operation can be stopped if an excessive load is applied. Therefore, the safety of the warping operation can be improved.

In a case where, the example, a variable voltage type regulator is used as the power supply voltage, control may be performed in such a manner that, if the warping instruction is made for a long time by an operator or the maximum warp is not realized although voltage V3 or V4 is applied, the level of power supply voltage V3 or V4 is raised and sufficiently large warp is made even if the load is large.

The flow chart for the upward/downward directional control shown in FIG. 69 is periodically (for example, every 10 ms) started. Also the control flow chart for the lateral directional control is arranged similarly and therefore it is omitted from illustration here.

Although the range of the straight-like state is ±10°, the present invention is not limited to this.

The structure according to the sixteenth embodiment is arranged in such a manner that the warping operation switch 958 is used to simply discriminate whether or not switching on/off is made.

A first modification of the sixteenth embodiment may be arranged in such a manner that the endoscope 941 uses a unit composed by combining a slide type knob with the potentiometer 975 in place of the encoder 965 and the rotational angle detecting circuit 967 uses an A/D converter 976 in place of the up/down counter 972. Thus, the angle of warp is read by the CPU 39 via the bus line 974. Since the other structures, operations and effects are the same as those according to the sixteenth embodiment, their descriptions are omitted here.

A second modification is arranged in such a manner that a joy-stick may be provided in place of the warping operation switch 958 according to the sixteenth embodiment or its first modification.

Then, the operation of the second modification will now be described with reference to a flow chart shown in FIG. 69. The same operations as those of the flow chart shown in FIG. 68 are given the same step Nos. and their descriptions are omitted here.

In step S140A, a fact that the joy-stick is at a neutral portion (straight position) or a position change (a quantity of warping operation) is made is discriminated. In step S145A, a fact that the position change is in the upward direction or the downward direction is discriminated. In step S148 after performing the processes in steps S146 and S147, whether or not the warping has been made by a degree corresponding to the position change is discriminated. If the aforesaid change is not made, a predetermined warping operation is continued until the aforesaid change is made. When the quantity of change is made, the warping operation is stopped in step S149 and the flow returns to step S140A.

A third modification may be employed which is arranged in such a manner that a switch for selecting a mode in which the voltage level is switched in the straight state or the like and a mode in which no switching is performed is added to the operation portion 945 in addition to the elements according to the sixteenth embodiment, or the first modification or the second modification. In this structure, in only the mode in which the switching is made, the control circuit 968 discriminates whether or not the leading portion 948 is in the straight state or the like so as to perform control.

Another structure may be employed in which another switch is provided for the operation portion 945 and the control circuit 968 performs control in such a manner that the quantity of warp of the leading portion with respect to the movement of the joy-stick becomes the half (or it may be determined by an operator) after the switch has been depressed. In this case, the positioning of the leading portion by means of the joy-stick can be performed delicately.

Figure 70:
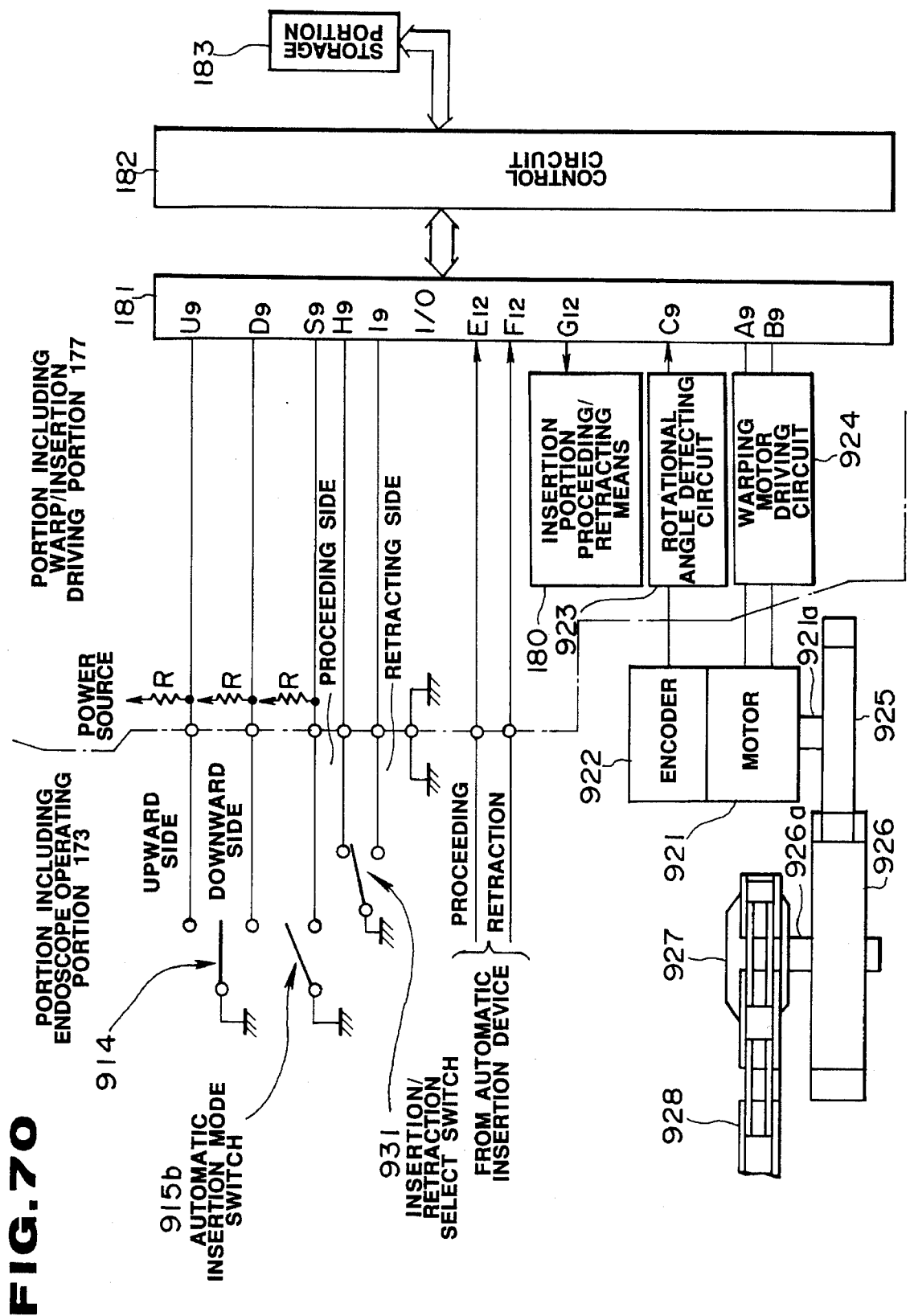
Figure 71:
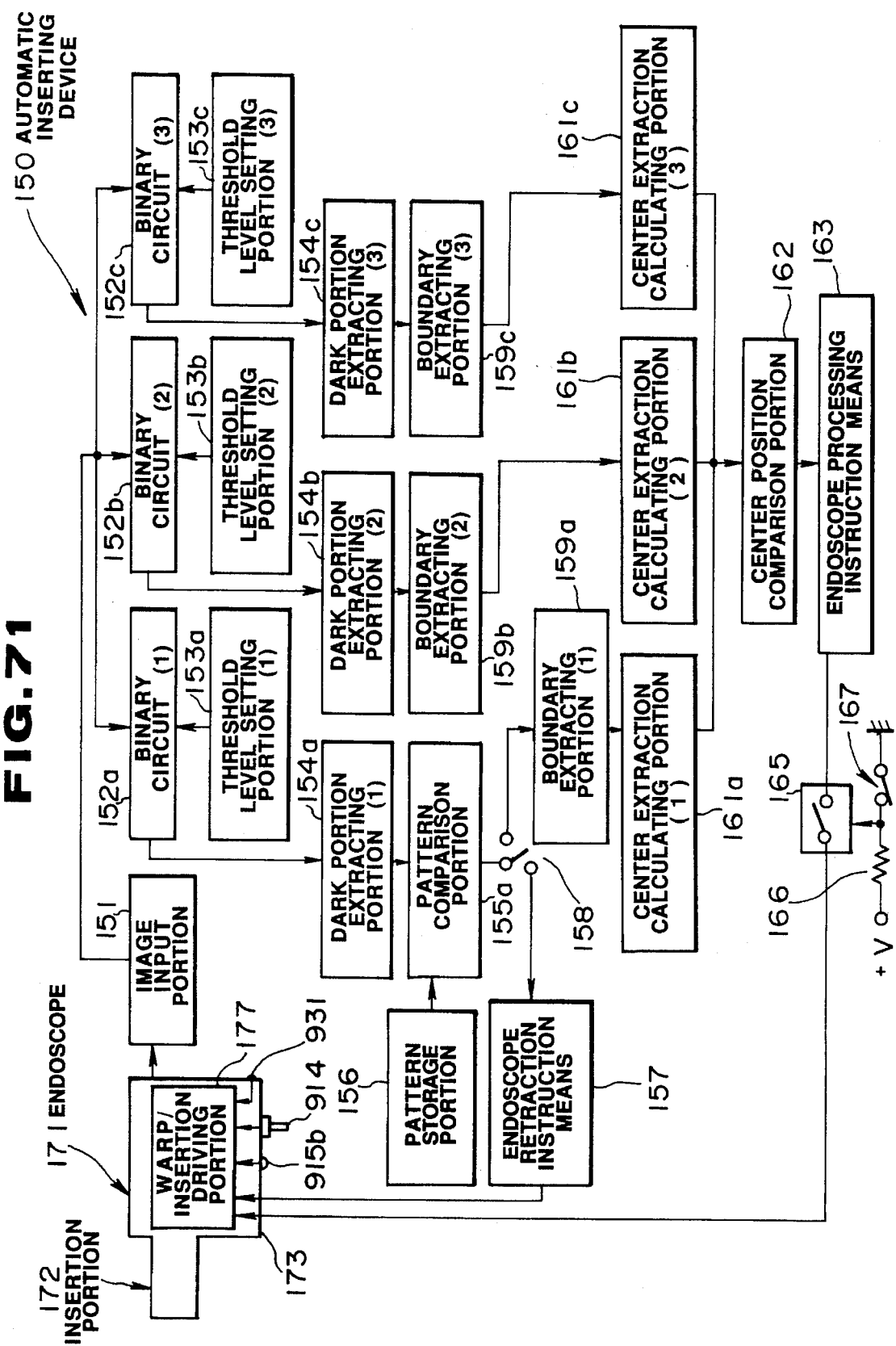
Figure 72:
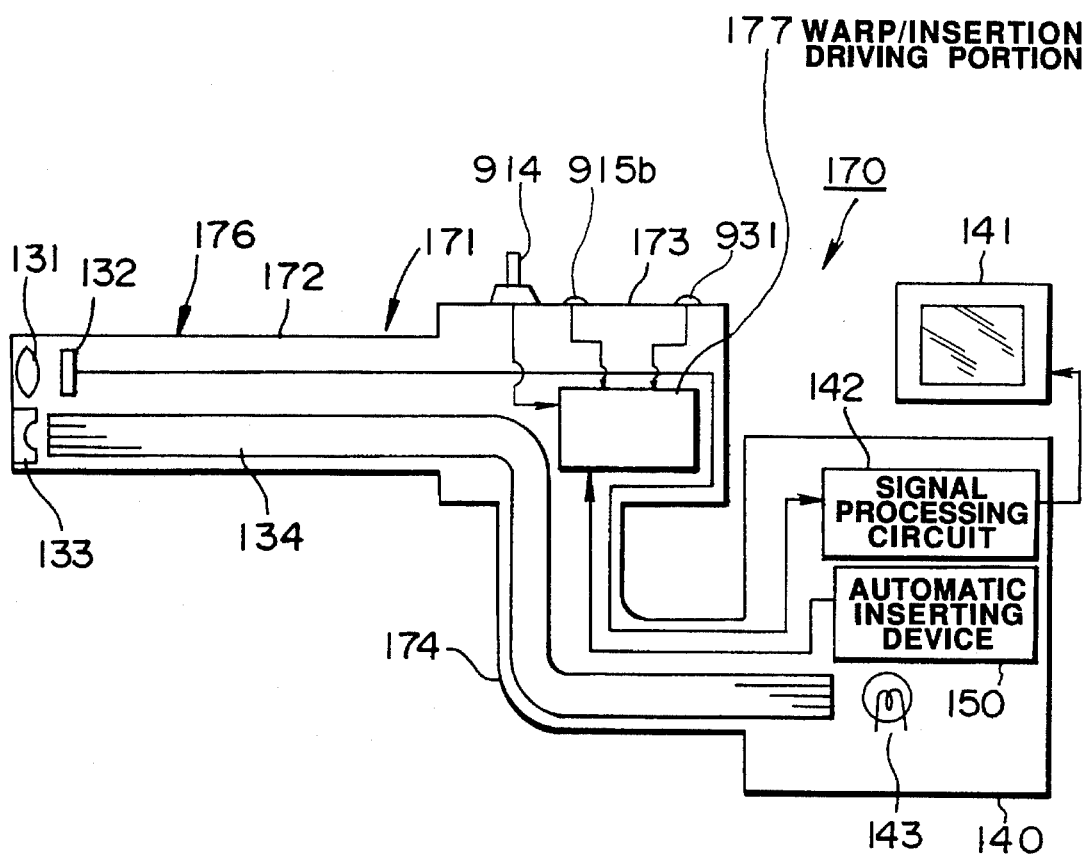
Figure 73:
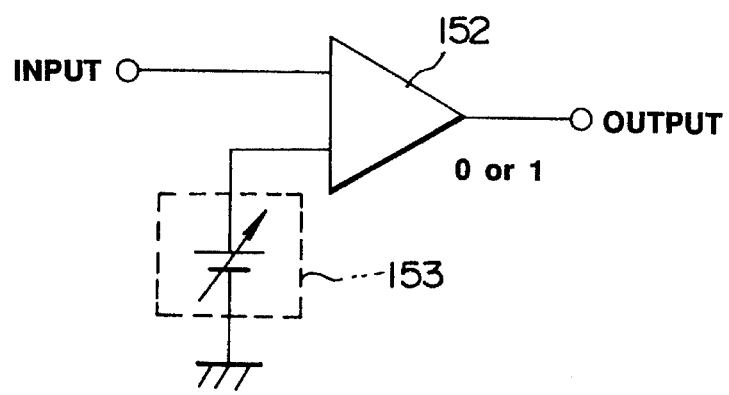
Figures 77, 78, 79:
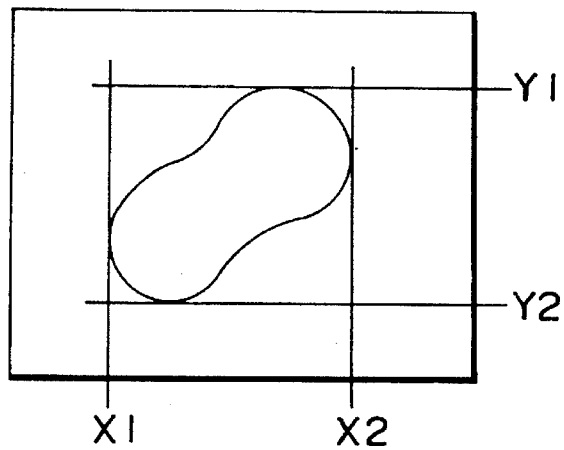
Figure 82:
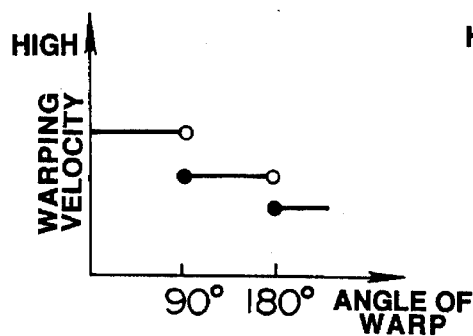
Figure 82:
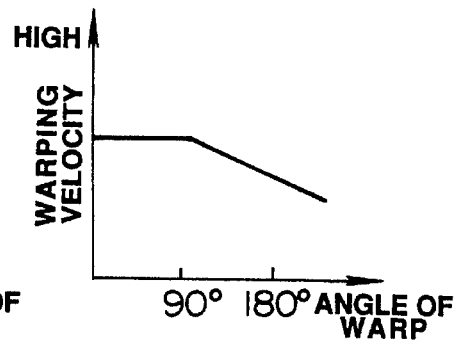
Figure 82:
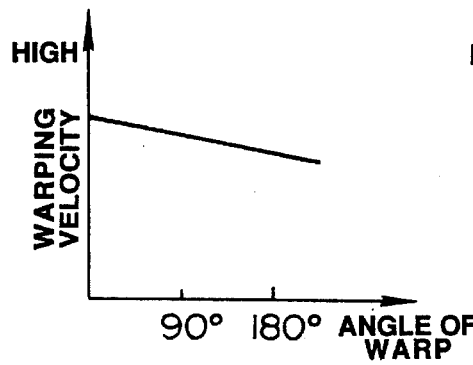
Figure 82:
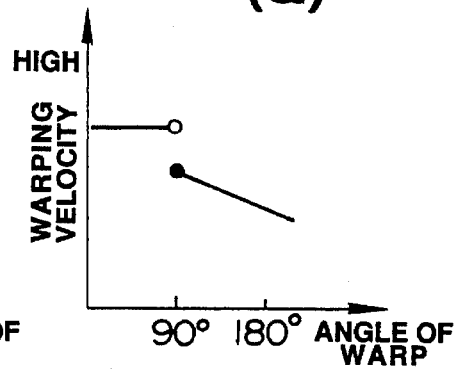

FIGS. 70 to 82 illustrate a seventeenth embodiment of the present invention. FIG. 70 is a schematic structural view which illustrates a warping mechanism and a warping/insertion proceeding and retracting means. FIG. 71 is a block diagram which illustrates the structure of an automatic inserting device of the endoscope. FIG. 72 is a schematic structural view which illustrates the overall structure of an endoscope apparatus. FIG. 73 is a circuit diagram which illustrates a binary circuit and a threshold level setting portion. FIGS. 74(a) and 74(b) illustrate the operation of the dark portion extracting portion. FIG. 75 illustrates a plurality of regions extracted by the dark portion extracting portion. FIG. 76 illustrates an endoscope image formed in a state where the leading portion of the endoscope has excessively approached the subject of the inspection. FIG. 77 illustrates a contrast pattern in a pattern comparison portion. FIG. 78 illustrates the operation of the boundary extracting portion. FIG. 79 illustrates the operation of a center extraction calculating portion. FIG. 80 illustrates the operation of the automatic insertion device to be performed in a case where the tract is straight. FIG. 81 illustrates the operation of the automatic insertion device to be performed in a case where the tract is bent. FIG. 82 illustrates functions relating to the warping control operation.

As shown in FIG. 72, the automatic insertion type electromotive warping type endoscope apparatus 170 comprises an endoscope 171, a control device 140 to which the endoscope 171 is connected and a monitor connected to the control device 140.

The endoscope comprises a flexible elongated insertion portion 172 and an operation portion 173 disposed adjacent to the rear end portion of the insertion portion 172. A flexible universal cord 174 extends from the side portion of the operation portion 173. Furthermore, the end portion of the universal cord is connected to the control device 140. A warp-enabled portion 176 which can be warped is disposed at the leading portion of the insertion portion 172. The warping operation of the warp-enabled portion 176 is controlled by a warp/insertion driving portion 177 provided for the endoscope 171 via the warping mechanism shown in FIG. 70.

The warp/insertion driving portion 177 is able to forwardly move the insertion portion 172 by means of an insertion portion proceeding/retracting means shown in FIG. 70.

As the proceeding/retracting means for the insertion portion 172, for example, means disclosed in Japanese Patent Laid-Open No. 62-41635 may be employed. As an alternative to this, means for forward moving the insertion portion 172 may be provided adjacent to the rear end portion of the insertion portion 172.

A plurality of angle wires (omitted from illustration) are, as the warping mechanism for warping the warp-enabled portion 176, inserted into the insertion portion 172. The leading portions of the angle wires are secured to the leading portion of the warp-enabled portion 176. The rear end portions of the angle wires are connected to the chain 928 shown in FIG. 70. The chain 928 is pulled via the drive gear 925, the driven gear 926 and the sprocket 927 by the rotation of the motor 921 as shown in FIG. 70. As a result, the warp-enabled portion 176 can be warped in an arbitrary direction. The motor 921 has the encoder 922 coaxially so as to detect the rotation angle of the motor 921.

As the warping mechanism, an actuator made of a shape-memory alloy or the like may be provided in the warp-enabled portion 176.

The endoscope operation portion 173 has a warping operation switch 914, an automatic insertion mode selection switch 915b and an insertion proceeding/retracting operation switch 931.

The endoscope operation portion 173 is arranged in such a manner that drums 916a and 916b are connected to a drum drive circuit 919 and a rotation speed sensor 918 is connected to the rotation speed detecting circuit 920.

The warping/insertion driving portion 177 comprises a rotational angle detecting circuit 923 to which the encoder 922 is connected, a warping motor drive circuit 924 and an input/output port (hereinafter called an "I/O") 181 disposed between the aforesaid units and the control circuit 930 and acting to interface the input and the output of signals. The control circuit 182 and the I/O 181 are connected by a bus line.

The warping operation switch 914 is provided for the purpose of warping the warp-enabled portion 909 in the upward or the downward direction. A common terminal of the warping operation switch 914 is grounded. An upward terminal of the warping operation switch 914 is connected to an U9 terminal of the I/O 181 and an end portion of a resistor R having an end which is connected to the power source is connected to the warping operation switch 914.

A terminal of the automatic insertion mode selection switch 15b is grounded and another terminal of the same is connected to an S9 terminal of the I/O 181. Furthermore, a terminal of the resistor R another terminal of which is connected to the power source is connected to the automatic insertion mode selection switch 915b.

Furthermore, an I/O 181 is provided in place of the I/O 929, a control circuit 181 for performing control of the angle of warp and the warping velocity according to a predetermined function when an automatic insertion mode to be described later is selected is provided in place of the control circuit 930 and a storage portion 183 is provided which stores the predetermined function relating to the angle of warp and the warping velocity.

The aforesaid insertion proceeding/retracting operation switch 931 acts to move forwards/rearward the insertion portion 171 and has a common terminal grounded. A forward movement directional terminal of the insertion proceeding/retracting operation switch 931 is connected to the terminal H9 of the I/O 181. Furthermore, a terminal of a resistor R another terminal of which is connected to the power source is connected to it.

In addition to the insertion proceeding/retracting operation switch 931 provided for the endoscope operation portion 173, the warping/insertion driving portion 177 is arranged to supply an output signal from the automatic insertion device to be described later to input terminals E12 and F12 of the I/O 181. The terminal E12 receives an output signal transmitted from an endoscope forward-movement instruction means 163 shown in FIG. 71, while the terminal F12 receives an output signal transmitted from an endoscope rearward-movement instruction means 157 shown in FIG. 71.

The aforesaid warping/insertion driving portion 177 is structured as described above so as to automatically forwards or rearward move the insertion portion 172 in response to the output signal transmitted from the automatic insertion device 150 when the automatic insertion mode selection switch 915*b* is switched on. When the switch 915*b* is switched off, the insertion proceeding/retracting operation switch 931 is operated. As a result, the insertion portion 172 is manually moved forwards or rearward. The warping/insertion driving portion 177 warps the warp-enabled portion 176 at a predetermined warping velocity by means of the control circuit 182 when the switch 915*b* is switched off. When the switch 915*b* is switched on, it controls the warping velocity in accordance with the function stored in the storage portion 183. This embodiment is characterized by the aforesaid control of the warping velocity.

The rotational angle detecting circuit 923 provided for the warp/insertion driving portion 177 detects the rotational angle of the encoder 922. On the other hand, the warping motor drive circuit 924 provided for the warp/insertion driving portion 177 controls the rotation speed of the motor 921, that is, the warping velocity in accordance with an instruction made by the control circuit 182. That is, the control circuit 182 supervises the rotational angle of the encoder 922 so as to cause the warp-enabled portion 176 to be warped at the instructed velocity.

The control circuit 182 controls the insertion portion proceeding/retracting means 180 provided for the warp/insertion driving portion 177 via a terminal G12 of the I/O 181. That is, the control circuit 182 controls the insertion portion 172 to be inserted/retracted at the instructed velocity in response to an output signal transmitted from the automatic insertion device 150 or the operation of the switch 914.

The endoscope insertion portion 172 has an observing window and, for example, two illuminating windows (omitted from illustration) at the leading portion thereof. An objective lens 131 is disposed inside the observing window and a solid-state image sensing device 132 is disposed at the image forming position of the objective lens 131. The solid-state image sensing device 132 is connected to a signal processing circuit 142 provided for the control device 140 via a signal line passing through the insertion portion 172, the operation 173 and the universal cord 174. Furthermore, a light distributing lens 133 is disposed inside the illuminating window and a light guide 134 made of a fiber bundle is connected to the rear end portion of the light distributing lens 133. The light guide 134 is inserted into the insertion portion 172, the operation portion 173 and the universal cord 174 and the light emitting side end of it is connected to the control device 140. Illuminating light emitted from a light source lamp 143 provided for the control device 140 is made incident upon the light incident end of the light guide 134.

The solid-state image sensing device 132 is driven by the signal processing circuit 142 and acts to transmit an output signal which is processed into a video signal in the signal processing circuit 142. The video signal transmitted from the signal processing circuit 142 is supplied to a monitor 141 so that an image of a subject is displayed on the monitor 141.

The present invention is not limited to the endoscope 171 having the solid-state image sensing device 132 at the leading portion of the insertion portion 172 thereof. Another structure may be employed which is composed of a fiber scope for transmitting an image to an ocular portion by an image guide made of a fiber bundle and a TV camera connected to the ocular portion of this fiber scope.

The control device includes the automatic insertion device 150 for controlling the warp/insertion driving portion 177 by discriminating the insertion condition of the endoscope 171. The automatic insertion device 150 is arranged to receive an image signal transmitted from the signal processing circuit 142.

Referring to FIG. 71, the automatic insertion device 150 will now be described.

The automatic insertion device 150 has an image receiving portion 151 for receiving an image signal transmitted from the endoscope 171. The image signal received through the image receiving portion 151 is supplied to a plurality of, for example, three binary circuits (1 to 3) 152*a* to 152*c*. The binary circuits 152*a* to 152*c* convert the endoscope image into a binary image while making the threshold level determined by threshold level setting portions (1 to 3) 153*a* to 153*c* to the threshold. The threshold level setting portions 153*a*, 153*b* and 153*c* respectively have different threshold levels.

The binary circuit 152 (which represents those 152*a* to 152*c*) and the threshold level setting portion 153 (which represents those 153*a* to 153*c*) are structured as shown in FIG. 73. That is, the binary circuit 152 comprises a comparator, while the threshold level setting portion 153 comprises a variable-voltage source. The input terminal of the comparator receives the image signal supplied from the image receiving portion 151 and reference voltage supplied from the variable voltage source. The output from the comparator becomes "0" when the image signal level is higher than the threshold level and becomes "1" when the image signal level is lower than the threshold level.

The output signals from the binary circuits 152*a* to 152*c* are received by dark extraction portions (1 to 3) 154a to 154c. The dark extraction portion 154 (which represents 154*a* to 154c) converts each pixel of the supplied image into binary data. For example, an arrangement is made in such a manner that the threshold level of an image signal having brightness of each pixel formed into numeral data, as shown in FIG. 74(*a*), is made to be 3.5 and "1" is transmitted when it is smaller than 3.5 and "0" is transmitted when it is 3.5. Furthermore, each pixel is converted into binary data, a binary image, as shown in FIG. 74(*b*), is formed.

Referring to FIG. 74(*b*), the region composed of pixel "1" is the dark portion. By setting the threshold level as described above and by extracting region darker than it, an erroneous operation which takes place when there is only a non-clear darkness such as shadow and in which the dark is discriminated as the direction of the movement can be prevented.

Examples of the three dark regions extracted by the three dark portion extracting portions 154*a* to 154*c* are shown in FIG. 75.

As a method of extracting the dark portion, a method disclosed in Japanese Patent Application No. 1-23450 by an applicant of the present invention of Jan. 31, 1989 may be employed.

In order to eliminate a very small dark region generated due to bending of the image guide at the time of extracting the dark portion in a case where the fiber scope and the TV camera are used as the endoscope 171, an average value of data about pixels surrounding a certain pixel may be used as data about the certain pixel. As an alternative to this, a small dark portion may be omitted.

An output signal transmitted from one dark extracting portion (1) 154*a* is received by a pattern comparison portion 155. The pattern comparison portion 155 calculates the correlation between an image obtained by the dark portion extracting portion (1) 154a and a contrast pattern stored in the pattern storage portion 156. If the value of the correlation is larger than a predetermined value, the two patterns are discriminated to be the similar patterns. That is, assuming the binary data is $a_{n'm'}$ the contrast pattern data is $C_{n'm'}$ and a predetermined value is K, the conditions which cause the similar patterns to be realized are expressed by the following equation:

$$\sum_n \sum_m (C_{n'm} - a_{n'm})^2 < K$$

In a case where a pattern as shown in FIG. 76 is formed by dark portion extraction, or in a case where the entire region is darkened, it means a fact that the leading portion of the endoscope 171 has approached excessively the subject of the inspection such as the mucous. Therefore, the pattern comparison portion 155 recognizes the aforesaid pattern and transmits an instruction signal for rearward moving the endoscope. In a case where the leading portion of the endoscope 171 is in contact with the mucous, the overall visual field becomes black. However, if it is moved slightly away from it, light is introduced through two illuminating lenses. Therefore, circular-arc shaped bright portions are formed at the two end portions of the visual field as shown in FIG. 76. Examples of the contrast pattern for recognizing the pattern as shown in FIG. 76 are shown in FIGS. 77(a) and 77(b). A plurality of the contrast pattern of the type as described above may be provided.

An output signal from the pattern comparison portion 155 is selectively supplied to the endoscope rearward movement instruction means 157 and one of the boundary extracting portion (1) 159a via 1-input 2-output switch 158. When the switch 158 recognizes the contrast pattern and the similar pattern according to the result of a comparison made by the pattern comparison portion 155, it is switched to the endoscope rearward movement instruction means 157 and an instruction signal to rearward move the endoscope is supplied from the pattern comparison portion 155 to the endoscope rearward movement instruction means 157. The endoscope rearward movement instruction means 157 controls the warp/insertion driving portion 177 of the endoscope 171 so as to rearwardly move the insertion portion 172.

In a case where the contrast pattern and the similar pattern are not recognized, the switch 158 is switched to the boundary extraction portion (1) 159a, so that a binary image is supplied from the dark portion extracting portion (1) 154a to the boundary extracting portion (1) 159a.

The output signals from the other dark portion extracting portions (2 and 3) 154b and 154c are supplied to the corresponding boundary extracting portions (2 and 3) 159b and 159c. The boundary extracting portion 159 (159a to 159c) obtain coordinates of each line of the binary image at which binary data is changed from 0 to 1 or from 1 to 0. Furthermore, the boundary data of the obtained coordinates is made to be 1 and boundary data of the other coordinates is made to be 0. That is, assuming that binary data of the m-th pixel on the n-th line is boundary data $b_{n'm}$ is given from the following equation:

$$b_{n'm} = |a_{n'm}-1 - a_{n'm}|$$

An example of a binary image which is shown in FIG. 74(b) and the boundary of which has been extracted is shown in FIG. 78. In order to simplify the process, "0" is supplied to the first column.

Output signals from the boundary extracting portions 159a to 159c are respectively supplied to center extraction calculating portions (1 to 3) 161a to 161c. The center extraction calculating portions 161 (which represents 161a to 161c) extracts the central coordinates of an extracted dark portion. That is, for example, data about the extracted dark portion is subjected to a process in which the uppermost row and the lowermost row on which pixels data of which is 1 are present extracted and the average $(Y_1+Y_2)/2$ of the Y-coordinates $Y_1$ and $Y_2$ of the two rows is made to be the central coordinates of Y-axis. Similarly, the left end column and the right end column on which pixels data of which is 2 are present are extracted and average $(X_1+X_2)/2$ of the X-coordinates $X_1$ and $X_2$ of the two rows is made to be the central coordinates of X-axis.

Another method of extracting the central coordinates of the dark portion may be employed in which the number N of pixels included in the dark portion is obtained, the number of the pixels included in the dark portion is sequentially counted from the upper portion in the direction of the X-axis, and the Y-coordinate when the aforesaid number becomes N/2 is made to be the central coordinate of the Y-axis. Similarly, the number of the pixels included in the dark portion is sequentially counted from the left end in the direction of the Y-axis, and the X-coordinate when the aforesaid number becomes N/2 is made to be the central coordinate of the X-axis.

The output signals transmitted from the center extraction calculating portions 161a to 161c are supplied to the center position comparison portion 162. The center position comparison portion 162 calculates $$(X_1, Y_1) = (x_2 - x_1, y_2 - y_1)$$

$$(X_2, Y_2) = (x_3 - x_2, y_3 - y_2)$$

of each of the central coordinates $P_1$ $(x_1, y_1)$, $P_2$ $(x_2, y_2)$ and $P_3$ $(x_3, y_3)$ of the three regions (dark portions) extracted corresponding to the three threshold level.s The aforesaid central coordinates $P_1$, $P_2$ and $P_3$ are arranged in the sequential order of the darkness of the threshold level.

As described above, the center position comparison portion 162 detects the changes in the central coordinates of each region.

The output signal transmitted from the center position comparison portion 162 is supplied to the endoscope forward-movement instruction means 163. The endoscope forward-movement instruction means 163 sets the direction in which the endoscope is moved to be direction $P_3$ $(x_3, y_3)$ and sets the movement velocity of the endoscope according to the following conditions, where $k_1$ and $k_2$ are predetermined values:

If $(X_{12}, Y_{12})1/2 < k_1$ and as well as      (1)

$(X_{22}, Y_{22})1/2 < k_2$, the velocity is high.

If $(X_{12}, Y_{12})1/2 < k_1$ and as well as      (2)

$(X_{22}, Y_{22})1/2 < k_2$, the velocity is medium.

$(X_{22}, Y_{22})1/2 < k_2$, the velocity is low.      (3)

Information about the conditions (the direction of movement and moving velocity) for inserting the endoscope is supplied to the warp/insertion driving portion 177 of the endoscope 171. The warp/insertion driving portion 177 directs the warp-enabled portion 176 of the endoscope 171 and moves the insertion portion 172 at the aforesaid moving velocity according to the aforesaid insertion condition.

The power source the voltage of which is V is connected to a control signal input terminal of the switch 165 via a resistor 166. The aforesaid power source can be grounded via an operator operation switch 167 provided for the operation portion 173 of the endoscope 171. Therefore, the switch 165 is switched on/off when the operator operation switch 167 is switched on/off. When there is a desire for the operator to stop inserting the endoscope and the operation switch 167 is switched off, the switch 165 is switched off and the insertion is stopped.

The warp/insertion driving portion 177 can be manually operated as well as it can be controlled by the automatic insertion device 150. Although this embodiment is described about the number of pixels is 5×5 for convenience, a similar effect can be obtained in a case where a more large number of pixels are present.

The operation of the automatic insertion device 150 will now be described with reference to FIGS. 80 and 81.

An endoscope image taken by the solid-state image sensing device 132 of the endoscope 171 is supplied to the automatic insertion device 150 via the image receiving portion 151. Then, the endoscope image is converted into binary data with three different threshold levels by the binary circuit 152. Then, the dark region corresponding to each threshold is extracted by the dark portion extracting portion 154. The boundary of the regions is extracted by the boundary extracting portion 159 and the center extraction calculating portion 161 is used to obtain the center of each of the regions. The center position comparison portion 162 makes the comparison of the center position of each region. In accordance with the result of the comparison, the endoscope forward movement instruction means 163 sets the endoscope insertion conditions. According to the aforesaid insertion conditions, the warp/insertion driving portion 177 is used to insert the endoscope 171. If the pattern comparison portion 155 recognizes a specific pattern, the endoscope 171 is moved rearward.

In a case where the tract 168 is straight in shape, the endoscope image becomes as shown in FIG. 80(a) and the boundary of each region becomes as shown in FIG. 80(b). The inside portion of the image shown in FIG. 80(b) becomes dark in proportion to the distance from the outer periphery. In this case, centers $P_1$, $P_2$ and $P_3$ of each region substantially coincide with one another. Since the endoscope can be moved at high velocity in the aforesaid case, the endoscope forward movement instruction means 163 sets the moving direction to the direction of $P_3$ and as well as set the moving velocity to high level.

If the tract 168 into which the endoscope 171 is inserted is bent, the endoscope image becomes as shown in FIG. 81(a) and the boundary of each region becomes as shown in FIG. 81(b). The inside portion of the image shown in FIG. 81(b) becomes dark in proportion to the distance from the outer periphery. In this case, centers $P_1$, $P_2$ and $P_3$ of each region becomes deviated in accordance with the state of bending as shown in FIG. 81(c). In this case, the endoscope must be moved according to the state of bending of the tract. Therefore, the endoscope forward movement instruction means 163 sets the moving direction to $P_3$ and the moving velocity is set to the medium or low level according to the aforesaid condition (2) or (3).

If the center of each region is deviated from one another as shown in FIG. 81(c), the moving directions may be deviated in the sequential order to $P_3$, $P_2$ and $P_1$.

As described above, according to this embodiment, the state of the subject of the inspection is discriminated, proper insertion conditions are set according to the state and the endoscope can be automatically inserted. Therefore, the endoscope can be properly inserted according to the state of the subject of the insertion and the endoscope can be easily inserted.

Although the endoscope apparatus according to this embodiment is arranged in such a manner that the endoscope is automatically inserted according to the discriminated endoscope insertion conditions, it may be inserted by the operator by utilizing the discriminated endoscope insertion conditions.

The aforesaid description is made about the automatic insertion when the automatic insertion mode selection switch 915b is switched on. Then, control of the warping velocity of the warp-enabled portion 176 to be performed in such a manner that the warping operation switch 914 is operated when the switch 915b is switched on will now be described.

The control circuit 182 of the warp/insertion driving portion 177 detects information about the angle of warp of the warp-enabled portion 176 by means of the encoder 922 and the rotational angle detecting circuit 923. The control circuit 182 controls the warping velocity of the warp-enabled portion 176 in accordance with a predetermined function stored by the storage portion 183 on the basis of detected information about the angle of warp.

As for the function stored by the storage portion 183, four examples of it are shown in graphs shown in FIGS. 82(a) to 82(d).

The function shown in FIG. 82(a) lowers the warping velocity in a stepped manner while making two points at which the angle of warp is 90° and 180° to be boundaries. Therefore, according to this function, when the angle of warp becomes large, the control circuit 182 lowers the warping velocity in two steps according to function data stored in the storage portion 183 in the automatic insertion mode.

The function shown in FIG. 82(b) holds the warping velocity constant when the angle of warp is ranged from 0° to less than 90° and linearly raises the warping velocity when the angle of warp exceeds 90°. The function shown in FIG. 82(c) linearly lowers the warping velocity when the warping angle is ranged from 0° to the maximum angle of warp (according to the illustrated example, an angle exceeding 180°). The function shown in FIG. 82(d) holds the warping velocity to be constant when the angle of warp ranges from 0° to an angle smaller than 90° and it is further lowered when the angle of warp exceeds 90° and the warping velocity is linearly lowered.

Any one of the functions stored in the storage portion 183 and shown in FIGS. 82(a) to 82(d) may be used or some functions may be switched and selected.

The warp-enabled portion 176 is warped at constant velocity by operating the warping operation switch 914 when the automatic insertion mode selection switch 915b is switched off. Also in this case, control by utilizing the aforesaid function may be performed.

A case where the angle of warp is large will cause a dangerous state for a patient as compared with a case where the same is small. Therefore, according to this embodiment, the warping velocity when the angle of warp is large is set to a low velocity in a case where the insertion portion is automatically driven. As a result, the dangerous state can be avoided when the operator stops warping depending upon a prediction of the dangerous state. As described above, according to this embodiment, the operability and safety at the time of performing the warping operation can be improved.

Figure 83:
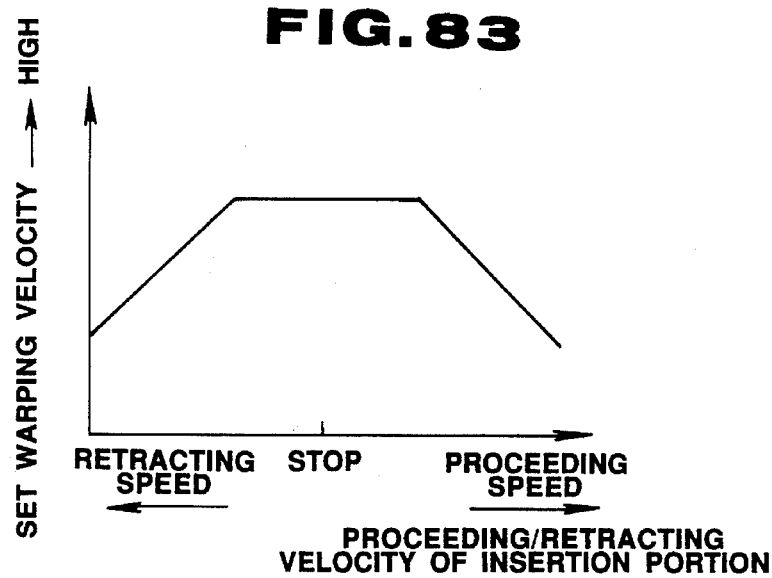
FIGS. 83 to 85 illustrate an eighteenth embodiment, where
Figure 84:
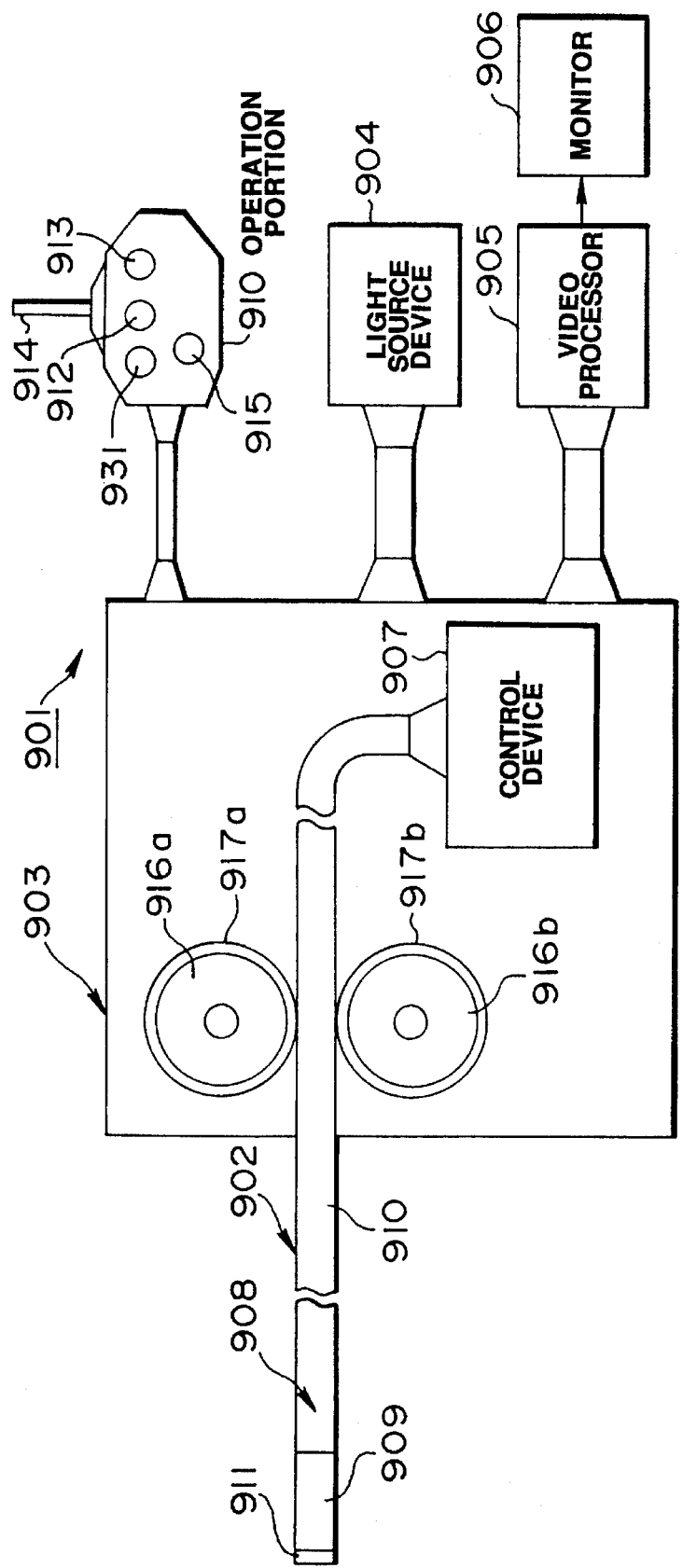
Figure 85:
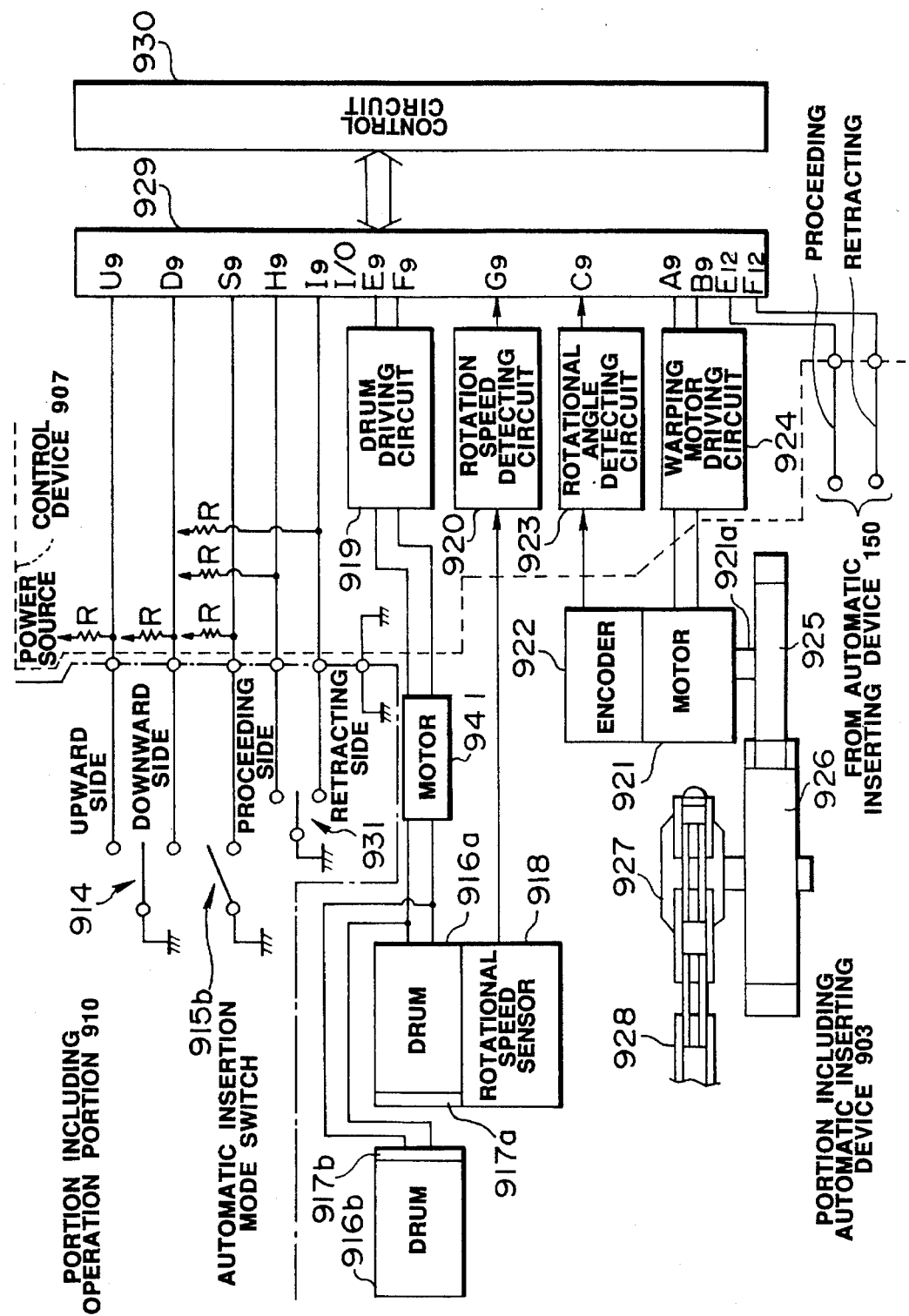

FIGS. 83 to 85 illustrate an eighteenth embodiment of the present invention. FIG. 83 illustrates the relationship between the actual warping velocity and set warping velocity. FIG. 84 is an overall structure view which illustrates an electromotive warping type endoscope apparatus. FIG. 85 is a block diagram which illustrates the electromotive warping type endoscope apparatus featuring an essential portion.

The electromotive warping type endoscope apparatus according to the eighteenth embodiment is arranged in such a manner that the endoscope insertion portion can be automatically inserted and an insertion velocity detecting sensor for detecting the insertion portion is provided for the purpose of varying the warping velocity according to the insertion velocity.

As shown in FIG. 85, an automatic insertion type electromotive warping type endoscope apparatus 901 comprises an electronic type electromotive warping type endoscope 902, an automatic insertion device 903 for automatically inserting/ejecting the electronic type electromotive warping type endoscope 902, a light source device 904 for supplying illuminating light to the electronic type electromotive warping type endoscope 902, a video processor 905 for processing a video signal obtained by the electronic type electromotive warping type endoscope 902 and a monitor 906 for receiving the video signal transmitted from the video processor 905 so as to display an image of a subject.

An insertion portion 908 of the electronic type electromotive warping type endoscope 902 comprises a leading unit 911, a warp-enabled portion 909 and a soft portion 910 when viewed from the leading portion. Furthermore, a control device 907 is connected to the rear end portion of the soft portion 910.

The operation portion 910 comprises an air/water supply button 912, a suction button 913, a warping operation switch 914 and an insertion proceeding/retracting operation switch 931.

The automatic insertion device 903 includes the control device 90 for controlling the forward/rearward movement of the insertion portion 908 and the warping operation of the warp-enabled portion 909 of the electronic type electromotive warping type endoscope 902.

The automatic insertion device 903 comprises the control device 907, a pair of drums 916a and 916b for forward/rearward moving the insertion portion 902 and a motor 915 for rotating the drums 916a and 916b.

As shown in FIG. 84, the control device 907 of the automatic insertion device 903 is electrically connected to the operation portion 910.

The automatic insertion device 903 includes the drums 916a and 916b for forward/rearward moving the insertion portion 908. Furthermore, the automatic insertion device 903 has an operation portion 910 for operating the warp-enabled portion 909 of the electronic type electromotive warping type endoscope 902.

The drums 916a and 916b are connected to a drum drive circuit 919, while the rotation speed sensor 918 is connected to a rotation speed detecting circuit 920.

An absolute type encoder 922 is disposed adjacent to the warping motor 921. The encoder 922 is connected to a rotational angle detecting circuit 923, while the warping motor 921 is connected to the warping motor drive circuit 924.

A drive gear 925 is secured to a shaft 921a of the warping motor 921. A driven gear 926 is engaged with the drive gear 925. A sprocket 927 is secured to a shaft 926a of the driven gear 926. A chain 928 is rotatively fastened to the sprocket 927. End portions of two wires (omitted from illustration) are connected to the end portions of the chain 928 by two connection members (omitted from illustration). The other end portions of the two wires are secured to a front warping block (omitted from illustration) of the warp-enabled portion 909.

The method of controlling the forward/rearward movement of the insertion portion 908 is the same as that according to the seventeenth embodiment in which the control device 907 issues an instruction of the forward/rearward movement of the insertion portion 908 and the drums 916a and 916b are rotated.

On the other hand, the control device 907 includes a control circuit 930 for controlling the warping motor drive circuit 924 on the basis of the rotation speed of the drum detected by the rotation speed detecting circuit 920. The warping operation of the warp-enabled portion 909 is controlled by the control circuit 930. The control device 907 comprises the drum drive circuit 919, the rotation speed detecting circuit 920, the rotational angle detecting circuit 923, and warping motor drive circuit 924 and an input/output port (hereinafter called an I/O) 929 disposed between the aforesaid units and the control circuit 930 and interfacing input/output of signals. The control circuit 930 and the I/O 929 are connected to each other by a bus line.

The warping operation switch 914 acts to upwardly or downwardly warp the warp-enabled portion 909 and has a common terminal grounded. An upward terminal of the warping operation switch 914 is connected to a U9 terminal of the I/O 929 and an end terminal of a resistor R is connected to the warping operation switch 914, another end terminal of the resistor R being connected to a power source. The downward terminal of the warping operation switch 914 is connected to a D9 terminal of the I/O 929 and an end terminal of a resistor R is connected to the down terminal, another end terminal of the resistor R being connected to the power source.

The insertion proceeding/retracting operation switch 931 acts to manually forward or rearward move the insertion portion 908, the insertion proceeding/retracting operation switch 931 having a common terminal grounded. The insertion proceeding/retracting operation switch 931 has a proceeding terminal connected to an H9 terminal of the I/O 929 and an end terminal of a resistor R another terminal of which is connected to the power source is connected to the same. Furthermore, the insertion proceeding/retracting operation switch 931 has a retracting terminal connected to an I9 terminal of the I/O 929 and a terminal of a resistor R another terminal of which is connected to the power source is connected to the same.

Similarly to the seventeenth embodiment, an output signal transmitted from the automatic insertion device 150 is supplied to terminals E12 and F12 of the I/O 929.

The control circuit 930 comprises, for example, a CPU and acts to transmit a control signal via terminals A9, B9, E9 and F9 of the I/O 929.

On the other hand, the rotational angle detecting circuit 923 transmits angular data of the warp-enabled portion 909 to the control circuit 930 via a terminal C9 of the I/O 929. The rotation speed detecting circuit 920 transmits insertion velocity data of the insertion portion 902 to the control circuit 930 via a terminal G9 of the I/O 929.

The control circuit 930 converts rotation speed data of the rotation speed detecting circuit 920 into insertion velocity data and supervises the insertion velocity. The control circuit 930 controls the drum drive circuit 919 and the warping motor drive circuit 929 via the I/O 929 according to the insertion velocity data when the warping operation switch 914 is operated.

Although the warping direction is limited to the upward and downward directions in order to simplify the description, the warping direction may be in all four directions, including the right and left directions. Furthermore, a warping velocity switch may be provided for the operation portion.

First, the power source for the automatic insertion device 903 is turned on. As a result, the levels of the U9, D9, H9 and I9 terminals of the I/O 929 are made to be high ("H") and the control circuit discriminates that the present state is a stationary state. Furthermore, the levels of the E9, F9, A9 and B9 terminals of the I/O 929 are made to be low ("L"). Therefore, the drums 916a and 916b are brought into a stationary state and the insertion portion 908 is maintained at the stationary state. Also, the warping motor 921 is brought into the stationary state, so that the warp-enabled portion 909 is maintained at the stationary state.

When the automatic insertion mode selection switch 915b is switched on and an instruction of forward or rearward movement is supplied from the automatic insertion device 150 to the control circuit 930 via the I/O 929, the insertion portion 908 is moved forwardly or rearwardly according to the forward or rearward movement instruction similarly to the seventeenth embodiment. For example, if a forward movement instruction is issued, the level of the E12 terminal of the I/O 929 is lowered and the control circuit 930 transmits a high level signal to the terminal E9 of the I/O 929 and as well as transmits a low level signal to the terminal F9. When the motor 941, the rotation of which is controlled by the drum drive circuit 919 is rotated, the drums 916a and 916b are respectively rotated in the direction in which the insertion portion 908 is moved forwardly. As a result, the insertion portion 908 is moved forwardly.

If an instruction of stoppage is issued, the levels of the terminals E12 and F12 of the I/O 992 are raised the control circuit 930 transmits low level signals to the terminals E9 and F9. Therefore, the motor 941 is stopped and also the drums 916a and 916b are brought into the stationary state.

If an instruction of the rearward movement is issued, the level of the terminal F112 of the I/O 929 is lowered, that of the terminal F9 is raised and the terminal E9 transmits a low level signal. Since the drums 916a and 916b are respectively rotated in the direction in which the insertion portion 908 is moved rearward, the insertion portion 908 is moved rearwardly.

In the case where the automatic insertion mode selection switch 915b is switched off, the insertion portion 908 is moved forward or rearward in accordance with the instruction of the rearward or forward movement instruction issued through the insertion proceeding/retracting operation switch 931 (manual).

If the operator manually moves the insertion portion 908 forwardly or rearwardly, or the insertion portion 908 is moved forwardly or rearwardly according to the aforesaid automatic insertion mode, the rotation speed detecting circuit 920 transmits data about the insertion portion movement velocity via the rotation speed sensor 918.

The control circuit 930 sets the warping velocity of the warp-enabled portion 909 according to the movement velocity data in accordance with the relationship between the insertion portion movement velocity and the set warping velocity shown in FIG. 83. The control of the warping velocity is performed by the control circuit 930 regardless of a fact whether or not the automatic insertion mode selection switch 915b is switched on.

If the moving velocity of the insertion portion is fast, the state in the vicinity of the warp-enabled portion 909 can be easily rapidly changed. Therefore, a suitable measurement against the rapid alternation of the state cannot be taken if the warping velocity is high, causing danger to arise in that the endoscope comes in contact with the body wall. According to this embodiment, if the movement velocity of the insertion portion is high, the warping velocity is decelerated as shown in FIG. 83 in order to secure safety. Therefore, the warping operation can be performed safely.

Another structure may be employed in which a clutch is disposed between the two drums 916a, 916b and the motor 915. In this state, when the insertion proceeding/retracting operation switch 931 is switched on, the clutch is engaged and the same is released when the switch 931 is switched off.

Figures 86, 87:
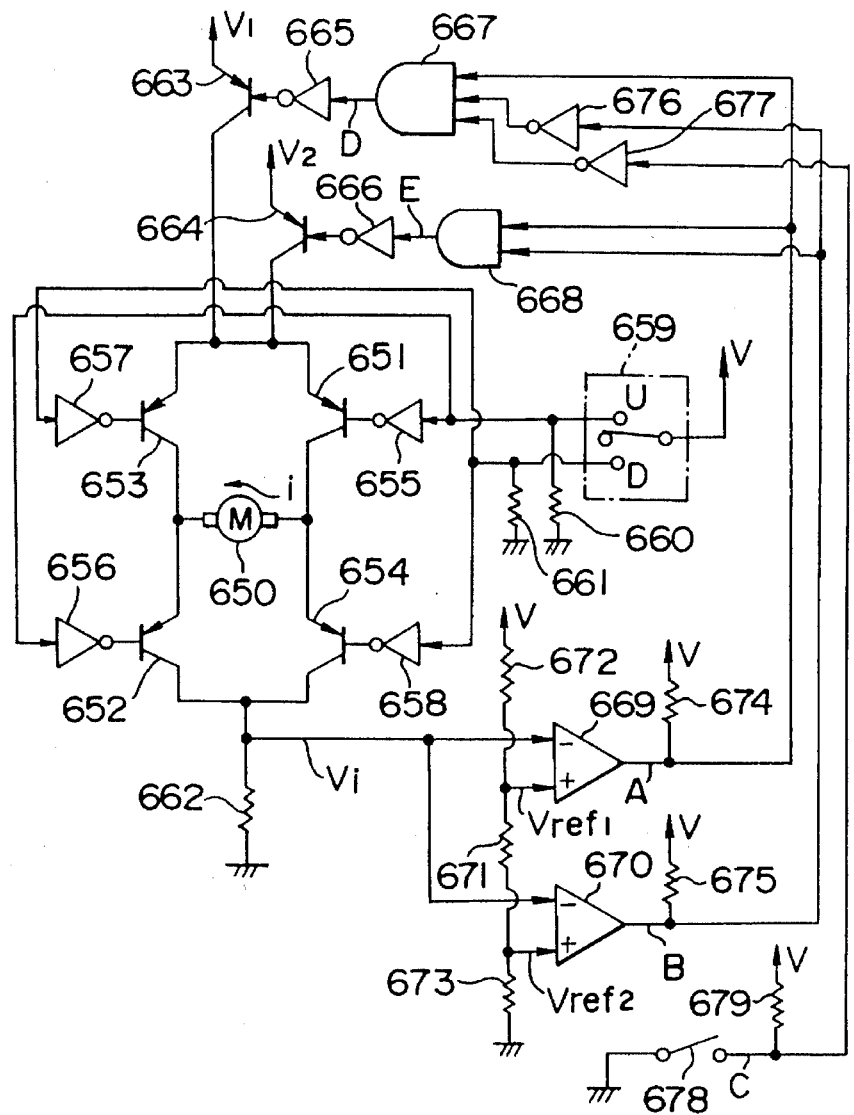
FIGS. 86 and 87 illustrate a nineteenth embodiment, where

FIGS. 86 and 87 illustrate a nineteenth embodiment of the present invention. FIG. 86 is a circuit diagram which illustrates the operation of controlling the warp-enabled portion. FIG. 87 is a truth value table of the circuit shown in FIG. 86.

This embodiment is arranged in such a manner that a selection switch for lowering the warping velocity or stopping the warping operation is provided for the structure according to any one of the third, or the ninth or the seventeenth embodiment in order to select a method of controlling the warping velocity. FIG. 86 illustrates only a schematic circuit structure for realizing the aforesaid effect.

In order to simplify the description, only the vertical directional warping operation will be described while omitting the lateral directional warping operation.

FIG. 86 illustrates a warping control circuit capable of lowering the warping velocity and stopping the warping operation.

PNP type transistors 651 to 654 serving as a so-called H-bridge circuit are connected to the two end portions of a warping DC motor 650. Outputs from open-collector output inverter 655 to 658 are connected to the bases of the transistors 651 to 654. The inputs of the inverters 655 to 658 are connected to an up/down operation SW 659. Specifically, the inverters 655 and 656 are connected to an upward terminal of the operation SW 659, while the inverters 657 and 658 are connected to a downward terminal of the operation SW 659. The common terminal of the up/down operation SW 659 is connected to a power source V. The upward and the downward terminals are grounded via resistors 660 and 661.

The collectors of the transistors 651 and 653 and the emitters of the transistors 652 and 654 are connected to the two terminals of the motor 650.

The collectors of the transistors 652 and 654 are grounded via a resistor 662. The emitters of the transistors 651 and 653 are connected to the collectors of the transistors 663 and 664.

The emitters of the transistors 663 and 664 are respectively connected to the power sources V1 and V2. Open-collector output inverters 665 and 665 are respectively connected to the bases of the transistors 663 and 664. Outputs D and E of a 3-input AND circuit 667 and a 2-input AND circuit 668 are respectively connected to the inverters 665 and 666.

The collectors of the transistors 652 and 658 are connected to the reverse inputs of comparators 669 and 670. An end portion and another end portion of a resistor 671 are interposed and connected between non-reverse inputs of the comparators 669 and 670. An end portion of the resistor 617 is connected to the power source V via a resistor 672 and another end portion of the resistor 671 is grounded via a resistor 673.

Outputs A and B of the comparators 669 and 670 are connected to the power source V via resistors 674 and 675.

The output A is connected to an input of each of the AND circuits 657 and 658. The output B is connected to another input of the AND circuit 668 and also connected to another input of the AND circuit 667 via an inverter 676.

An output C of a selection switch 678 is connected to the power source V via a resistor 679. An output Y is connected to another input of the AND circuit 667 via an inverter 677. According to this embodiment, a relationship V1<V2 is held.

In this structure, when the up/down operation SW 659 is not operated, no electric current passes through the motor 650. Therefore, the insertion portion cannot be warped.

When the SW 659 is operated in the upward direction, the transistors 651 and 652 are turned on, causing an electric current to pass through the motor in a direction i, as shown in FIG. 86. As a result, an upward directional warp is enabled.

If the operation SW 659 is operated in the downward direction, the transistors 653 and 654 are turned on. Therefore, an electric current passes through the motor 650 in a direction opposing to the direction i, causing the insertion portion to be warped downwardly.

Since the level of the output C is high when the selection SW 678 is switched off, the level of the input of the AND circuit 667 is lowered, while the output D necessarily is lowered. Therefore, the transistor 663 is turned off. When the SW 678 is switched on, the level of the output C is low and therefore the input of the AND circuit 667 is raised. Therefore, the transistor 663 is turned on/off according to the outputs A and B of the comparators 669 and 670.

First, an operation to be performed when the selection SW 678 is switched off will now be described.

When the operation SW 659 is operated in the upward direction, an electric current passes through the motor 650 in the direction i as described above. Therefore, voltage Vi is generated at an end portion of the resistor 662. The voltage Vi is subjected to comparisons with reference voltage levels Vref1 and Vref2 to be supplied to the non-reverse input terminals of the comparators 669 and 670, where Vref1>Vref2.

If Vi<Vref2, the outputs A and B from the comparators 669 and 670 becomes "H" and "H" respectively If Vref2<Vi<Vref1, the outputs A and B from the comparators 669 and 670 becomes "H" and "L" respectively If Vref1<Vi, the outputs A and B from the comparators 669 and 670 becomes "L" and "L" respectively Since Vi=0 immediately after the operation SW 659 has been switched on, the transistor 663 is in a state where it is turned on (the transistor 664 is turned off). When voltage Vi<Vref2, A, B and C becomes "H" "H" and "H" since the load acting on the warping motor 650 is small and the electric current i is small, causing the outputs D and E to become "L" and "H" respectively Therefore, the transistor 664 is turned on and application of voltage V2 to the emitters of the transistors 651 and 653 is continued.

If the electric current i becomes large and a relationship Vi>Vref2 is held, the outputs A, B and C becomes "H" "L" and "H". If a relationship Vi>Vref1 is held, the outputs A, B and C become "L", "L" and "H", respectively. Therefore, both of the outputs D and E become "L" and "L". Therefore, both of the transistors 663 and 664 are turned off and no voltage is applied to the emitters of the transistors 651 and 653.

Therefore, if the load becomes larger than a certain level, that is, if the voltage Vi becomes larger than a certain level, no voltage is applied to the transistors 651 and 653. Therefore, no electric current passes through the motor 650. As a result, when the selection SW 678 is switched off and the load acting on the warp-enabled portion or the like becomes larger than a certain level, the warping operation is stopped.

Also in the downward directional warping operation, the same operation is performed except for the fact that the direction in which the electric current passing through the motor is inverted. Therefore, its description is omitted here.

Then, the operation to be performed when the selection SW 678 is switched on will now be described.

First, the transistor 663 is in a state where it is turned on. At this time, the transistor 664 is turned off. When the operation SW 659 is operated in the upward or the downward direction, the load applied to the motor 650 is small and a relationship Vi<Vref2 is held, the levels of the outputs A, B and C become "H" "H" and "L" respectively Therefore, the levels of the outputs D and E become "L" and "H" respectively. As a result, the transistor 664 is turned on and the application of the voltage V2 to the emitters of the transistors 651 and 653 is maintained.

In a case where Vi>Vref2, the levels of the outputs A, B, C are "H" "L" and "L" respectively. Therefore, the levels of the outputs D and E become "H" and "L" respectively As a result, the transistors 663 and 664 are respectively turned on and off, causing V1 to be applied to the emitters of the transistors 651 and 653.

In a case where Vi>Vref1, the levels of the outputs A, B and C are "L", "L" and "L". Therefore, the levels of the outputs D and E become "L" and "L" respectively. As a result, both of the transistors 663 and 664 are turned off, causing no voltage to be applied to the emitters of the transistors 661 and 653.

That is, if the load becomes larger than a certain level, the voltage to be applied is reduced (from V2 to V1). Furthermore, if the lead is further enlarged over a certain level, the application of the voltage is inhibited.

This means a fact that, if the selection SW 678 is switched on and the load applied to the warp-enabled portion of the endoscope is enlarged over a certain level, the warping velocity is lowered. Furthermore, if a larger load is applied, the warping operation is stopped.

In the operation with the electromotive warping type endoscope apparatus which employs the warping operation control circuit according to this embodiment, the warping operation is stopped if an excessively large load is applied or the warping velocity is lowered. If a further large load is applied, the warping operation is stopped. Therefore, the operation can be switched according to the intention and the skill of the operator. As a result, the operability and the safety can be improved.

Another structure may be employed in which the switch 678 according to the nineteenth embodiment is provided for the structure according to the third embodiment and a selection can be made from the "case in which the warping velocity is decelerated" and the "case in which the warping operation is stopped".

That is, although illustration is omitted from FIG. 15, the SW 678 is connected to the I/O 51 and control circuit 48 switches the "case in which the warping velocity is decelerated" and the "case in which the warping operation is stopped" by the switching operation of the SW 678.

It can be applied to the second to the tenth embodiments and the seventeenth embodiment.

Figures 88, 89:
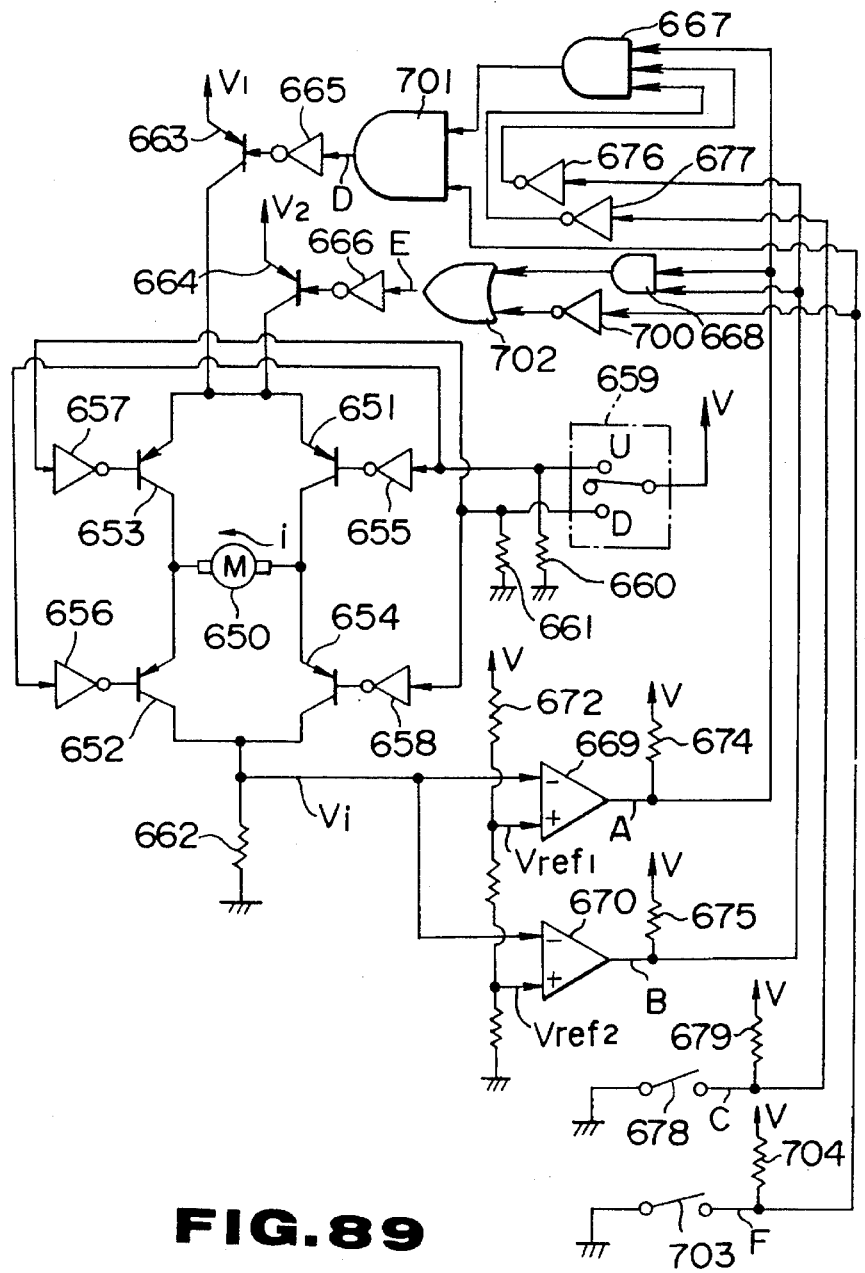
FIGS. 88 and 89 illustrate a twenties embodiment, where

FIGS. 88 and 89 illustrate a twenties embodiment of the present invention. FIG. 88 is a circuit diagram which illustrates an operation of controlling the warping operation of the warp-enabled portion. FIG. 89 is a truth value table of the circuit shown in FIG. 88.

According to this embodiment, a 2-input AND circuit 701 and an inverter 700 are provided in addition to the 3-input AND circuit 667 according to the nineteenth embodiment as shown in FIG. 89.

According to this embodiment, a 2-input OR circuit 702 is provided in addition to the 2-input AND circuit 668 according to the nineteenth embodiment.

According to this embodiment, a function switch 703 is provided in addition to the structure according to the nineteenth embodiment. An output F from the function switch 703 is connected to the power source V via a resistor 704. Furthermore, it is connected to one of the input terminals of the AND circuit 701 and the input terminal of the inverter 700. Another input terminal of the AND circuit 701 is connected to an input terminal of the AND circuit 667 and an output D of the AND circuit 701 is connected to an input terminal of the inverter 665.

An output terminal of the AND circuit 668 is connected to one of the input terminals of the OR circuit 702. Furthermore, the output terminal of the inverter 700 is connected to the other input terminal of the OR circuit 702. In addition, the output E of the OR circuit 702 is connected to the input terminal of the inverter 666.

The same structures and the operations as those according to the nineteenth embodiment are given the same reference numerals and their descriptions are omitted here.

As shown in FIG. 79, the operations are the same as those according to the nineteenth embodiment when the function switch 703 is switched off.

When the switch 703 is switched off, the level of the output F is "L". Therefore, the level of the output D of the AND circuit 701 is always "L" and the level of the output E of the OR circuit 702 is always "H". As a result, voltage V2 is always applied to the emitters of the transistors 651 and 653.

According to this embodiment, by switching on the function SW 703, the warping velocity can be always made constant. Furthermore, when the SW 703 is switched off, a similar effect to that obtainable according to the nineteenth embodiment can be obtained. Therefore, an operator is able to select the method of controlling the warping velocity and the operability can be improved. The other structures, operations and the effects are the same as those according to the nineteenth embodiment and their descriptions are omitted here.

This embodiment may be arranged in such a manner that the output from the SW 703 is supplied to the I/O 51 according to the third embodiment so as to select the functions of the "deceleration" and the "stop" similarly to the nineteenth embodiment. Furthermore, it may be applied to the second to the fifteenth embodiments.

In all of the embodiments except for the thirteenth and the tenth embodiments, an optical fiber endoscope may be employed in place of the electronic endoscope.

Although the power supply voltage can be altered by using the DC motor as an example of the driving means, a stepping motor can be used to change the frequency of the driving pulse.

The driving means is not limited to the DC motor or the stepping motor. In all of the aforesaid embodiments, the driving means may be compressed fluid or an SMA (Shape Memory Alloy) which acts to pull the wires in place of the motor. As an alternative to this, the actuator may be deformed by means of the SMA or the compressed fluid.

Although the invention has been described in its preferred form with a certain degree of particularity, it is understood that the present disclosure of the preferred form has been changed in the details of construction and the combination and arrangement of parts may be resorted to without departing from the spirit and the scope of the invention as hereinafter claimed.

What is claimed is:

1. An electromotive warping type endoscope apparatus comprising:

an insertion portion capable of being inserted into a subject to be inspected and including a warp-enabled portion;

a warping mechanism for warping said warp-enabled portion;

driving means connected to said warping mechanism for driving said warping mechanism;

quantity of warp instruction means for instructing said driving means to warp said warp-enabled portion wherein said instruction includes the direction of warp;

detecting means for detecting a state of said insertion portion; and warping velocity control means for supplying a control signal for automatically controlling the warping velocity, including at least one of warping speed and warping direction, of said warp-enabled portion to said driving means according to the state of said insertion portion detected by said detecting means, wherein said control signal consists of one of a deceleration control, a stoppage control, and a control of moving in a direction which is different from the warping direction instructed by said quantity of warp instruction means, wherein said control signal is formed according to the state of said insertion portion with priority given over said instruction output by said quantity of warp instruction means, wherein said detecting means includes electric quantity detecting means for detecting an electric quantity to be supplied to said driving means, and wherein said detecting means further includes time detecting means for detecting a time in which the electric quantity detected by said electric quantity detecting means is larger than a predetermined value; and said warping velocity control means controls the warping velocity whenever the time detected by said time detecting means is longer than a predetermined time.

2. An electromotive warping type endoscope apparatus comprising:

an insertion portion capable of being inserted into a subject to be inspected and including a warp-enabled portion;

a warping mechanism for warping said warp-enabled portion.;

driving means connected to said warping mechanism for driving said warping mechanism;

quantity of warp instruction means for instructing said driving means to warp said warp-enabled portion wherein said instruction includes the direction of warp;

detecting means for detecting a state of said insertion portion; and warping velocity control means for supplying a control signal for automatically controlling the warping velocity, including at least one of warping speed and warping direction, of said warp, enabled portion to said driving means according to the state of said insertion portion detected by said detecting means, wherein said control signal consists of one of a deceleration control, a stoppage control, and a control of moving in a direction which is different from the warping direction instructed by said quantity of warp instruction means, wherein said control signal is formed according to the state of said insertion portion with priority given over said instruction output by said quantity of warp instruction means, wherein said detecting means includes an electric quantity detecting means for detecting an electric quantity for driving said driving means for determining the state of said insertion portion, wherein said warping velocity control means determines that said insertion portion comes in contact with said subject to be inspected in accordance with a function of the level of the electric quantity detected by said detecting means and supplies said control signal for controlling the warping velocity of said warp-enabled portion to said driving means, wherein said detecting means further includes angle of warp detecting means for detecting the angle of warp of said warp-enabled portion and said warping velocity control means makes a comparison between the electric quantity detected by said electric quantity detecting means and a predetermined electric quantity determined in accordance with the angle of warp detected by said angle of warp detecting means to control the warping velocity of said warp-enabled portion, wherein said warping velocity control means includes storage means for storing a predetermined electric quantity determined in accordance with the angle of warp of said warp-enabled portion as data and controls the warping velocity of said warp-enabled portion if the ratio of data in said storage means and said angle of warp detected by the angle of warp detecting means is larger than a predetermined value.

* * * * *